(12) United States Patent
Hanna

(10) Patent No.: US 7,468,261 B2
(45) Date of Patent: *Dec. 23, 2008

(54) MOLECULAR DETECTION SYSTEMS UTILIZING REITERATIVE OLIGONUCLEOTIDE SYNTHESIS

(75) Inventor: Michelle M Hanna, Phoenix, AZ (US)

(73) Assignee: Ribomed Biotechnologies, Inc., Phoenix, AZ (US)

( * ) Notice: Subject to any disclaimer, the term of this patent is extended or adjusted under 35 U.S.C. 154(b) by 241 days.

This patent is subject to a terminal disclaimer.

(21) Appl. No.: 10/602,045

(22) Filed: Jun. 24, 2003

(65) Prior Publication Data

US 2004/0234996 A1  Nov. 25, 2004

Related U.S. Application Data

(62) Division of application No. 09/984,664, filed on Oct. 30, 2001, now Pat. No. 7,045,319.

(51) Int. Cl.
*C12P 19/34* (2006.01)
*C12Q 1/68* (2006.01)

(52) U.S. Cl. .......................................... 435/91.1; 435/6

(58) Field of Classification Search ........................ None
See application file for complete search history.

(56) References Cited

U.S. PATENT DOCUMENTS

| | | | |
|---|---|---|---|
| 3,996,345 A | 12/1976 | Ullman et al. |
| 4,351,760 A | 9/1982 | Khanna et al. |
| 4,582,788 A | 4/1986 | Erlich |
| 4,683,194 A | 7/1987 | Saiki et al. |
| 4,739,044 A | 4/1988 | Stabinsky |
| 4,757,141 A | 7/1988 | Fung et al. |
| 4,786,600 A | 11/1988 | Kramer et al. |
| 5,130,238 A | 7/1992 | Malek et al. |
| 5,169,766 A | 12/1992 | Schuster et al. |
| 5,194,370 A | 3/1993 | Berninger et al. |
| 5,246,866 A * | 9/1993 | Nasu et al. ................ 204/461 |
| 5,399,491 A | 3/1995 | Kacian et al. |
| 5,503,979 A | 4/1996 | Kramer et al. |
| 5,508,178 A | 4/1996 | Rose et al. |
| 5,554,516 A | 9/1996 | Kacian et al. |
| 5,571,669 A * | 11/1996 | Lu et al. .......................... 435/6 |
| 5,595,891 A | 1/1997 | Rose et al. |
| 5,597,694 A | 1/1997 | Munroe et al. |
| 5,648,211 A | 7/1997 | Fraiser et al. |
| 5,654,142 A | 8/1997 | Kievits et al. |
| 5,679,512 A | 10/1997 | Laney et al. |
| 5,683,879 A | 11/1997 | Laney et al. |
| 5,744,308 A | 4/1998 | Guillou-Bonnici et al. |
| 5,766,849 A | 6/1998 | McDonough et al. |
| 5,824,517 A | 10/1998 | Cleuziat et al. |
| 5,837,459 A * | 11/1998 | Berg et al. .......................... 435/6 |
| 5,846,723 A | 12/1998 | Kim et al. |
| 5,858,801 A | 1/1999 | Brizzolara |
| 5,888,729 A * | 3/1999 | Kacian et al. .................. 435/6 |
| 5,888,819 A | 3/1999 | Goelet et al. |
| 6,008,334 A | 12/1999 | Hanna |
| 6,107,037 A | 8/2000 | Sousa et al. |
| 6,107,039 A | 8/2000 | Hanna |
| 6,114,519 A | 9/2000 | Cole et al. |
| 6,251,594 B1 | 6/2001 | Gonzalgo et al. |
| 6,268,131 B1 | 7/2001 | Kang et al. |
| 7,045,319 B2 | 5/2006 | Hanna |
| 2002/0168641 A1 | 11/2002 | Mortensen et al. |
| 2003/0099950 A1 | 5/2003 | Hanna |
| 2004/0054162 A1 | 3/2004 | Hanna |
| 2004/0137461 A1 | 7/2004 | Hanna |
| 2004/0157257 A1 | 8/2004 | Hanna |
| 2004/0175724 A1 | 9/2004 | Hanna |
| 2005/0026150 A1 | 2/2005 | Hanna |
| 2005/0064414 A1 | 3/2005 | Hanna |
| 2005/0214796 A1 | 9/2005 | Hanna |

(Continued)

FOREIGN PATENT DOCUMENTS

EP   0 369 775 A   5/1990

(Continued)

OTHER PUBLICATIONS

Gohara et al., "Poliovirus RNA-dependent RNA Polymerase (3Dpol)," The Journal of Biological Chemistry, 2000, vol. 275, No. 33, pp. 25523-25532.*

(Continued)

*Primary Examiner*—Young J Kim
(74) *Attorney, Agent, or Firm*—Sterne, Kessler, Goldstein & Fox P.L.L.C.

(57) ABSTRACT

The present invention provides methods for detecting the presence of a target molecule by generating multiple detectable oligonucleotides through reiterative enzymatic oligonucleotide synthesis events on a defined polynucleotide sequence. The methods generally comprise using a nucleoside, a mononucleotide, an oligonucleotide, or a polynucleotide, or analog thereof, to initiate synthesis of an oligonucleotide product that is substantially complementary to a target site on the defined polynucleotide sequence; optionally using nucleotides or nucleotide analogs as oligonucleotide chain elongators; using a chain terminator to terminate the polymerization reaction; and detecting multiple oligonucleotide products that have been synthesized by the polymerase. In one aspect, the invention provides a method for detecting a target protein, DNA or RNA by generating multiple detectable RNA oligoribonucleotides by abortive transcription.

52 Claims, 31 Drawing Sheets

U.S. PATENT DOCUMENTS

2006/0204964 A1  9/2006  Hanna

FOREIGN PATENT DOCUMENTS

WO  WO 89/01050  2/1989
WO  WO 03/038042 A2  5/2003

OTHER PUBLICATIONS

Agrawal, S., and Tang, J.-Y., "Site-specific functionalization of oligodeoxynucleotides for non-radioactive labeling," *Tetrahedron Lett.* 31:1543-1546, Pergamon Press (1990).

Chamberlin, M.J., "Bacterial DNA-Dependent RNA Polymerases," in *The Enzymes*, Boyer, P.D., ed., Academic Press, New York, N.Y. pp. 61, 84-86 (1982).

Costas, C., et al., "RNA-protein crosslinking to AMP residues at internal positions in RNA with a new photocrosslinking ATP analog," *Nucleic Acids Res.* 28:1849-1858, Oxford University Press (May 2000).

Daube, S.S., and von Hippel, P.H., "Functional Transcription Elongation Complexes from Synthetic RNA-DNA Bubble Duplexes," *Science* 258:1320-1324, American Association for the Advancement of Science (1992).

Dunn, J.J., and Studier, F.W., "Complete Nucleotide Sequence of Bacteriophage T7 DNA and the Locations of T7 Genetic Elements," *J. Mol. Biol .* 166:477-535, Academic Press, Inc. (1983).

Gait, M.J., et al., "Oligoribonucleotide synthesis," in *Oligonucleotides and Analogues*, Eckstein, F., ed., Oxford University Press, Oxford, Grat Britian, pp. 25-31 (1992).

Gait, M.J., "An Introduction to Modern Methods of DNA Synthesis," in *Oligonucleotide synthesis: a practical approach*, Gait, M.J., ed., Oxford University Press, Oxford, Great Britain, pp. 1-22 (1984).

Geider, K., et al., "An RNA transcribed from DNA at the origin of phage fd single strand to replicative form conversion," *Proc. Natl. Acad. Sci. USA* 75:645-649, National Academy Press (1978).

Guatelli, J.C., et al., "Isothermal, in vitro amplification of nucleic acids by a multienzyme reaction modeled after retroviral replication," *Proc. Natl. Acad. Sci. USA* 87:1874-1878, National Academy Press (1990).

Gupta, K.C., et al., "A general method for the synthesis of 3'-sulfhydryl and phosphate group containing oligonucleotides," *Nucleic Acids Res.* 19:3019-3025, Oxford University Press (1991).

Gurevich, V.V., et al., "Preparative in Vitro mRNA Synthesis Using SP6 and T7 RNA Polymerases," *Anal. Biochem.* 195:207-213, Academic Press, Inc. (1991).

Hanna, M.M., "Photoaffinity Cross-Linking Methods for Studying RNA-Protein Interactions," *Methods Enzymol.* 180:383-409, Academic Press, Inc. (1989).

Hanna, M.M., et al., "Probing the environment of nascent RNA in *Escherichia coli* transcription elongation complexes utilizing a new fluorescent ribonucleotide analog," *Nucleic Acids Res.* 27:1369-1376, Oxford University Press (1999).

Hanna, M.M., et al., "Synthesis and characterization of a new photocrosslinking CTP analog and its use in photoaffinity labeling *E.coli* and T7 RNA polymerases," *Nucleic Acids Res.* 21:2073-2079, Oxford University Press (1993).

He, B., et al., "Preparation of probe-modified RNA with 5-mercapto-UTP for analysis of protein-RNA interactions," *Nucleic Acids Res.* 23:1231-1238, Oxford University Press (1995).

Kwoh, D.Y., et al., "Transcription-based amplification system and detection of amplified human immunodeficiency virus type 1 with a bead-based sandwich hybridization format," *Proc. Natl. Acad. Sci. USA* 86:1173-1177, National Academy Press (1989).

Lewis, M.K., and Burgess, R.R., "Transcription of Simian Virus 40 DNA by Wheat Germ RNA Polymerase II," *J. Biol. Chem.* 255:4928-4936, American Society for Biochemistry and Molecular Biology (1980).

Martin, C.T., et al., "Processivity in Early Stages of Transcription by T7 RNA Polymerase," *Biochemistry* 27:3966-3974, American Chemical Society (1988).

Meyer, K.L., and Hanna, M.M., "Synthesis and Characterization of a New 5-Thiol-Protected Deoxyuridine Phosphoramidite for Site-Specific Modification of DNA," *Bioconjugate Chem.* 7:401-412, American Chemical Society (1996).

Milligan, J.F., and Uhlenbeck, O.C., "Synthesis of Small RNAs Using T7 RNA Polymerase," *Methods Enzymol.* 180:51-62, Academic Press, Inc. (1989).

Montemagno, C., and Bachand, G., "Constructing nanomechanical devices powered by biomolecular motors," *Nanotechnology* 10:225-231, IOP Publishing, Ltd. (1999).

Mullis, K., et al., "Specific Enzymatic Amplification of DNA In Vitro: The Polymerase Chain Reaction," *Cold Spring Harb. Symp. Quant. Biol.* 51:263-273, Cold Spring Harbor Labortory (1986).

Mullis, K.B., et al., "The Polymerase Chain Reaction: Why It Works," in *Polymerase Chain Reaction*, Erlich, H.A., et al., eds., Cold Spring Harbor Laboratory Press, Woodbury, N.Y., pp. 237-243 (1989).

Nelson, P.S., et al., "Bifunctional oligonucleotide probes synthesized using a novel CPG support are able to detect single base pair mutations," *Nucleic Acids Res.* 17:7187-7194, Oxford University Press (1989).

Pringsheim, P., "Fluorescence of organic compounds,"in *Fluorescence and phosphorescence*, Pringsham, P., ed., Interscience Publishers, Inc. New York, N.Y., pp. 392-397, 420-423 (1949).

Saiki, R.K., et al., "Primer-Directed Enzymatic Amplification of DNA with a Thermostable DNA Polymerase," *Science* 239:487-491, American Association for the Advancement of Science (1988).

Sinha, N.D., and Striepeke, S., "Oligonucleotides with reporter groups attached to the 5'-terminus," in *Oligonucleotides and Analogues: A Practical Approach*, Eckstein, F., ed., Oxford University Press pp. 185-189, 200-201 (1992).

Smithies, O., et al., "Detection of Targeted Gene Modificatons by Polymerase Chain Reaction," in *Polymerase Chain Reaction*, Erlich, H.A., et al., eds., Cold Spring Harbor Laboratory Press, Woodbury, N.Y., pp. 199-203 (1989).

Sproat, B.S., et al., "The synthesis of protected 5'-mercapto-2',5'-dideoxyribonucleoside-3'-O-phosphoramidites; uses of 5'-mercapto-oligodeoxyribonucleotides," *Nucleic Acids Res.* 15:4837-4848, Oxford University Press (1987).

Walker, G.T., et al., "Isothermal in vitro amplification of DNA by a restriction enzyme/DNA polymerase system," *Proc. Natl. Acad. Sci. USA* 89:392-396, National Academy Press (1992).

Zuckermann, R., et al., "Efficient methods for attachment of thiol specific probes to the 3'-ends of synthetic oligodeoxyribonucleotides," *Nucleic Acids Res.* 15:5305-5321, Oxford University Press (1987).

Daube et al., "Functional Transcription Elongation Complexes from Synthetic RNA-DNA Bubble Complexes," Science, 1992, vol. 258, pp. 1320-1324.

Mancini et al.., Constitutively Methylated CpG Dinucleotides as Mutation Hot Spots in the Retinoblastoma Gene (RB1), American Journal of Human Genetics, 1997, vol. 61, pp. 80-87.

International Search Report for International Application No. PCT/US02/34419, mailed Jul. 24, 2003, International Searching Authority/USA, Washington, D.C.

Antequerra, F., and Bird, A., "Number of CpG islands and genes in human and mouse," *Proc. Natl. Acad. Sci. USA* 90:11995-11999, National Academy of Sciences (1993).

Callahan, R., et al., "Frequent Mutations in Breast Cancer," *Ann. N.Y. Acad. Sci.* 698:21-30, New York Academy of Sciences (1993).

Cifone, M.A., and Fidler, I.J., "Increasing metastatic potential is associated with increasing genetic instability of clones isolated from murine neoplasms," *Proc. Natl. Acad. Sci. USA* 78:6949-6952, National Academy of Sciences (1981).

Esteller, M., et al., "Promoter Hypermethylation and BRCA1 Inactivation in Sporadic Breast and Ovarian Tumors," *J. Natl. Cancer Inst.* 92:564-569, Oxford University Press (Apr. 2000). (Retrieved from LexisNexis Academic database).

Frommer, M., et al., "A genomic sequencing protocol that yields a positive display of 5-methylcytosine residues in individual DNA strands," *Proc. Natl. Acad. Sci. USA* 89:1827-1831, National Academy of Sciences (1992).

Giusti, W.G., and Adriano, T., "Synthesis and Characterization of 5'-Fluorescent-dye-labeled Oligonucleotides," *PCR Methods Appl.* 2:223-227, Cold Spring Harbor Laboratory Press (1993).

Herman, J.G., et al., "Inactivation of the CDKN2/p16/MTS1 Gene Is Frequently Associated with Aberrant DNA Methylation in All Common Human Cancers," *Cancer Res.* 55:4525-4530, American Association for Cancer Research (1995).

Herman, J.G., et al., "Incidence and functional consequences of *hMLH1* promoter hypermethylation in colorectal carcinoma," *Proc. Natl. Acad. Sci. USA* 95:6870-6875, National Academy of Sciences (1998).

Horii, A., et al., "Frequent Replication Errors at Microsatellite Loci in Tumors of Patients with Multiple Primary Cancers," *Cancer Res.* 54:3373-3375, American Association for Cancer Research (1994).

Issa, J.-P.J., et al., "Methylation of the oestrogen receptor CpG island links ageing and neoplasia in human colon," *Nat. Genet.* 7:536-540, Nature Publishing Co. (1994).

Jin, D.J., "An *Escherichia coli* RNA Polymerase Defective in Transcription due to its Overproduction of Abortive Initiation Products," *J. Mol. Biol.* 236:72-80, Academic Press Limited (1994).

Langer, P.R., et al., "Enzymatic synthesis of biotin-labeled polynucleotides: Novel nucleic acid affinity probes," *Proc. Natl. Acad. Sci. USA* 78:6633-6637, National Academy of Sciences (1981).

Loeb, L.A., "Mutator Phenotype May Be Required for Multistage Carcinogenesis," *Cancer Res.* 51:3075-3079, American Association for Cancer Research (1991).

Meinkoth, J., and Wahl, G., "Hybridization of Nucleic Acids Immobilized on Solid Supports," *Anal. Biochem.* 138:267-284, Academic Press, Inc. (1984).

Nowell, P.C., "The Clonal Evolution of Tumor Cell Populations," *Science* 194:23-28, American Association for the Advancemt of Science (1976).

Palmisano, W.A., et al., "Predicting Lung Cancer by Detecting Aberrant Promoter Methylation in Sputum," *Cancer Res.* 60:5954-5958, American Association for Cancer Research (Nov. 2000).

Radlowski, M., and Job, D., "Effect of disulfide and sulfhydryl reagents on abortive and productive elongation catalyzed by *Escherichia coli* RNA polymerase," *Acta Biochim. Pol.* 41:415-419. Panstwowe Wydawnictwo Naukowe (1994).

Rice, J.C., et al., "Aberrant methylation of the *BRCA1* CpG island promoter is associated with decreased BRCA1 mRNA in sporadic breast cancer cells," *Oncogene* 17:1807-1812, Stockton Press (1998).

Robertson, K.D., "DNA methylation, methyltransferases, and cancer," *Oncogene* 20:3139-3155, Nature Publishing Group (May 2001).

Tlsty, T.D., et al., "Differences in the rates of gene amplification in nontumorigenic and tumorigenic cell lines as measured by Luria-Delbrück fluctuation analysis," *Proc. Natl. Acad. Sci. USA* 86:9441-9445, National Academy of Sciences (1989).

Toyota, M., and Issa, J.-P.J., "CpG island methylator phenotypes in aginig and cancer," *Semin. Cancer Biol.* 9:349-357, Academic Press (1999).

Toyota, M., and Issa, J.-P.J., "The role of DNA hypermathylation in human neoplasia," *Electrophoresis* 21:329-333, Wiley-VCH Verlag GmbH (Jan. 2000).

Vogelstein, B., and Kinzler, K.W., "The multistep nature of cancer," *Trends Genet.* 9:138-141, Elsevier Science Publishers Ltd. (1993).

Wang, J.-Y., et al., "Monovalent cations differ in their effects on transcription initiation from a σ-70 promoter of *Escherichia coli*," *Gene* 196:95-98, Elsevier Science B.V. (1997).

Wu, D.Y., and Wallace, R.B., "The Ligation Amplification Reaction (LAR)—Amplification of Specific DNA Sequneces Using Sequential Rounds of Template-Dependent Ligation," *Genomics* 4:560-569, Academic Press, Inc. (1989).

Aiyar et al., "A Mismatch Bubble in Double-stranded DNA Suffices to Direct Precise Transcription Initiation by *Escherichia coli* RNA Polymerase," *The Journal of Biological Chemistry* 269:13179-13184, American Society for Biochemistry and Molecular Biology, Inc. (1994).

Daube et al., "Coupling of RNA displacement and intrinsic termination in transcription from synthetic RNA DNA bubble duplex constructs," *Proceedings of the National Academy of Sciences of the United States of America* 9:9539-9543, National Academy of Sciences (1994).

Griep et al., "Fluorescence Energy Transfer Between the Primer and the Beta Subunit of the DNA Polymerase III Holoenzyme," *Journal of Biological Chemistry* 267:3052-3059, The American Society for Biochemistry and Molecular Biology, Inc. (1992).

Hanna et al., "Topography of transcription: Path of the leading end of nascent RNA through the *Escherichia coli* transcription complex," *Proceedings of the National Academy of Sciences of the United States of America* 80:4238-4242, National Academy of Sciences (1983).

Kinsella et al., "RNA Polymerase: Correlation Between Transcript Length, Abortive Product Synthesis, and Formation of a Stable Ternary Complex," *Biochemistry* 21:2719-2723, American Chemical Sociey (1982).

Mancini et al., "Constitutively methylated CpG dinucleotides as mutation hot spots in the retinoblastoma gene (RBI)," *American Journal of Human Genetics* 61:80-87, The American Society of Human Genetics (1997).

Picketts et al., "Differential termination of primer extension: a novel, quantifiable method for detection of point mutations," *Human Genetics* 89:155-157, Springer-Verlag (1992).

Supplementary European Search Report for European Patent Application No. EP 02 79 5555, mailed Aug. 10, 2006, European Patent Office.

Cheung et al., "A Resource of Mapped Human Bacterial Artificial Chromosome Clones," *Genome Research* 9:983-993, Cold Spring Laboratory Press (1999).

Sasaki et al., "Transcriptional sequencing: A method for DNA sequencing using RNA polymerase" *Proc. Nat'l Acad. Sci. USA* 95:3455-3460 (1998).

\* cited by examiner n     $R_1N_1pN_2R_2-OH$

+ n     $pppN_3R_3$

WHERE $N_3$ IS A TERMINATOR n     $R_1N_1pN_2R_2pN_3R_3$

Lane 1 CMPS
Lane 2 CTPS
Lane 3 IAEDANS
Lane 4 AEDANS-SpppC
Lane 5 AEDANS-S-pC
Lane 6 AMPS
Lane 7 AEDANS-SpA
Lane 8 IAEDANS
Lane 9 CTPS
Lane 10 CMPS ATATACTGGGTCTACAAGGTTTAAGTCAACCAGGGATTGAAATATAACTTTTAAACAGAGCTGGATTATCCAGT
AGGCAGATTAAGCATGTGCTTTAAGGCATCAGCAAAGTCTGAGCAATCCATTTTTTAAAACGTAGTACATGTTTT
TGATAAGCTTAAAAAGTAGTAGTCACAGGAAAAATTAGAACTTTTACCTCCTTGCGCTTGTTATACTCTTTAGT
GCTGTTTAACTTTTCTTTGTAAGTGAGGGTGGTGGAGGGTGCCCATAATCTTTTCAGGGAGTAAGTTCTTCTT
GGTCTTTCTTTCTTTCTTTCTTTCTTTTTTTCTTGAGACCAAGTTTCGCTCTTGTCTCCCAGGCTGGAGTGCAA
TGGCGCGATCTCGGCTCACTGCAACCTCCGCCTTCTCCTGGGTTCAAGCGATTCTCCTACATCAGCCTCCGA
GTAGCTGGGATTACAGGCATGCGCCACCAAGCCCCGCTAATTTTGTATTTTTTAGTAGAGACAGGGTTTCGC
CATGTTGGTCAGGCTTGTCTCGAACTCCTGGCCTCAGGTGATCCGCCTGTCTCGGCCTCCCAGAATGCTGG
GATTATAGACGTGAGCCACCGCATCCGGACTTTCCTTTTATGTAATAGTGATAATTCTATCCAAAGCATTTTTT
TTTTTTTTTGAGTCGGAGTCTCATTCTGTCACCCAGGCTGGAGGGTGGTGGCGCGATCTCGGCTTACTGCAA
CCTCTGCCTCCCGGGTTCAAGCGATTCTCCTGCCTCAGCCTCCTGAGTAGCTGGAATTACACACGTGCGCCA
CCATGGCCAGCTAATTTTTGTATTTTTAGTAGAGACGGGGTGTCACCATTTTGGCCAAGCTGGCCTCGAACTC
CTGACCTCAGGTGATCTGCCCGCCTCGGCTTCCCAAAGTGCTGGGATTACAGGTGTGAGCCACCGCGTCCT
GCTCCAAAGCATTTTCTTTCTATGCCTCAAAACAAGATTGCAAGCCAGTCCTCAAAGCGGATAATTCAAGAGC
TAACAGGTATTAGCTTAGGATGTGTGGCACTGTTCTTAAGGCTTATATGTATTAATACATCATTTAAACTCACA
ACAACCCCTATAAAGCAGGGGGCACTCATATTCCCTTCCCCCTTTATAATTACGAAAAATGCAAGGTATTTTC
AGTAGGAAAGAGAAATGTGAGAAGTGTGAAGGAGACAGGACAGTATTTGAAGCTGGTCTTTGGATCACTGTG
CAACTCTGCTTCTAGAACACTGAGCACTTTTTCTGGTCTAGGAATTATGACTTTGAGAATGGAGTCCGTCCTT
CCAATGACTCCCTCCCCATTTTCCTATCTGCCTACAGGCAGAATTCTCCCCCGTCCGTATTAAATAAACCTCA
TCTTTTCAGAGTCTGCTCTTATACCAGGCAATGTACACGTCTGAGAAACCCTTGCCCCAGACAGCCGTTTTAC
ACGCAGGAGGGGAAGGGGAGGGGAAGGAGAGAGCAGTCCGACTCTCCAAAAGGAATCCTTTGAACTAGGG
TTTCTGACTTAGTGAACCCCGCGCTCCTGAAAATCAAGGGTTGAGGGGGTAGGGGGACACTTTCTAGTCGTA
CAGGTGATTTCGATTCTCGGTGGGGCTCTCACAACTAGGAAAGAATAGTTTTGCTTTTTTCTTATGATTAAAAGA
AGAAGCCATACTTTCCCTATGACACCAAACACCCCGATTCAATTTGGCAGTTAGGAAGGTTGTATCGCGGAG
GAAGGAAACGGGGCGGGGGCGGATTTCTTTTTAACAGAGTGAACGCACTCAAACACGCCTTTGCTGGCAGG
CGGGGGAGCGCGGCTGGGAGCAGGGAGGCCGGAGGGCGGTGTGGGGGCAGGTGGGGAGGAGCCCAGT
CCTCCTTCCTTGCCAACGCTGGCTCTGGCGAGGGCTGCTTCCGGCTGGTGCCCCGGGGGAGACCCAACC
TGGGGCGACTTCAGGGGTGCCACATTCGCTAAGTGCTCGGAGTTAATAGCACCTCCTCCGAGCACTCGCTC
ACGGCGTCCCCTTGCCTGGAAAGATACCGCGGTCCCTCCAGAGGATTTGAGGGACAGGGTCGGAGGGGGC
TCTTCCGCCAGCACCGGAGGAAGAAAGAGGAGGGGCTGGCTGGTCACCAGAGGGTGGGGCGGACCGCGT
GCGCTCGGCGGCTGCGGAGAGGGGGAGAGCAGGCAGCGGGCGGCGGGGAGCAGCATGGAGCCGGCGGC
GGGGAGCAGCATGGAGCCTTCGGCTGACTGGCTGGCCACGGCCGCGGCCCGGGGTCGGGTAGAGGAGGT
GCGGGCGCTGCTGGAGGCGGGGCGCTGCCCAACGCACCGAATAGTTACGGTCGGAGGCCGATCCAGGT
GGGTAGAGGGTCTGCAGCGGGAGCAGGGGATGGCGGGCGACTCTGGAGGACGAAGTTTGCAGGGGAATT
GGAATCAGGTAGCGCTTCGATTCTCCGGAAAAAGGGGAGGCTTCCTGGGGAGTTTTCAGAAGGGGTTTGTA
ATCACAGACCTCCTCCTGGCGACGCCCTGGGGGCTTGGGAAGCCAAGGAAGAGGAATGAGGAGCCACGCG
CGTACAGATCTCTCGAATGCTGAGAAGATCTGAAGGGGGGAACATATTTGTATTAGATGGAAGTATGCTCTTT
ATCAGATACAAAATTTACGAACGTTTGGGATAAAAAGGGAGTCTTAAAGAAATGTAAGATGTGCTGGGACTAC
TTAGCCTCCAATTCACAGATACCTGGATGGAGCTTATCTTTCTTACTAGGAGGGATTATCAGTGGAAATCTGT

FIG. 29A

```
GGTGTATGTTGGAATAAATATCGAATATAAATTTTGATCGAAATTATTCAGAAGCGGCCGGGCGCGGTGCCTC
ACGCCTTGTAATCCCTTCACTTTGGGAGATCAAGGCGGGGGGAATCACCTGAGGTCGGGAGTTCGAGACCA
GCCTGGCCAACAGGTGAAACCTCGCCTCTACTAAAAATACAAAAAGTAGCCGGGGGTGGTGGCAGGCGCCT
GTAATCCCAGCTACTCGGGAGGTTGAGGCAGGAGAATCGCTTGAACCCGGGAGGCTGAGGTTGTAGTGAAC
AGCGAGATGGAGCCACTTCACTCCAGCCTGGGTGACAGAGTGAGACTTTGTCGAAAGAAAGAAAGAGAGAA
AGAGAGAGAGAAAAATTATTCAGAAGCAACTACATATTGTGTTTATTTTTAACTGAGTAGGGCAAATAAATATA
TGTTTGCTGTAGGAACTTAGGAAATAATGAGCCACATTCATGTGATCATTCCAGAGGTAATATGTAGTTACCAT
TTTGGGAATATCTGCTAACATTTTTGCTCTTTTACTATCTTTAGCTTACTTGATATAGTTTATTTGTGATAAGAG
TTTTCAATTCCTCATTTTTGAACAGAGGTGTTTCTCCTCTCCCTACTCCTGTTTTGTGAGGGAGTTAGGGGAG
GATTTAAAAGTAATTAATACATGGGTAACTTAGCATCTCTAAAATTTTGCCAACAGCTTGAACCCGGGAGTTTG
GCTTTGTAGTCCTACAATATCTTAGAAGAGACCTTATTTGTTTAAAAACAAAAAGGAAAAAGAAAAGTGGATAG
TTTTGACAATTTTTTAATGGAG
```

FIG. 29B

SEQUENCE LISTING

```
<160> NUMBER OF SEQ ID NOS: 17

<210> SEQ ID NO 1
<211> LENGTH: 30
<212> TYPE: DNA
<213> ORGANISM: Artificial Sequence
<220> FEATURE:
<223> OTHER INFORMATION: methylated DNA template
<220> FEATURE:
<221> NAME/KEY: misc_feature
<222> LOCATION: (2)..(2)
<223> OTHER INFORMATION: methylation
<220> FEATURE:
<221> NAME/KEY: misc_feature
<222> LOCATION: (10)..(10)
<223> OTHER INFORMATION: methylation
<220> FEATURE:
<221> NAME/KEY: misc_feature
<222> LOCATION: (26)..(26)
<223> OTHER INFORMATION: methylation

<400> SEQUENCE: 1
ccgcccaaac gggtccggag cgactcgtca                                       30

<210> SEQ ID NO 2
<211> LENGTH: 30
<212> TYPE: DNA
<213> ORGANISM: Artificial Sequence
<220> FEATURE:
<223> OTHER INFORMATION: deaminated methylated DNA
<220> FEATURE:
<221> NAME/KEY: misc_feature
<222> LOCATION: (1)..(1)
<223> OTHER INFORMATION: n is uracil
<220> FEATURE:
<221> NAME/KEY: misc_feature
<222> LOCATION: (4)..(6)
<223> OTHER INFORMATION: n is uracil
<220> FEATURE:
<221> NAME/KEY: misc_feature
<222> LOCATION: (15)..(16)
<223> OTHER INFORMATION: n is uracil
<220> FEATURE:
<221> NAME/KEY: misc_feature
<222> LOCATION: (21)..(21)
<223> OTHER INFORMATION: n is uracil
<220> FEATURE:
<221> NAME/KEY: misc_feature
<222> LOCATION: (24)..(24)
<223> OTHER INFORMATION: n is uracil
<220> FEATURE:
<221> NAME/KEY: misc_feature
<222> LOCATION: (29)..(29)
<223> OTHER INFORMATION: n is uracil

<400> SEQUENCE: 2
```
ncgnnnaaac gggtnnggaa ngantcgtna                               30

<210> SEQ ID NO 3
<211> LENGTH: 30
<212> TYPE: DNA
<213> ORGANISM: Artificial Sequence
<220> FEATURE:
<223> OTHER INFORMATION: deaminated unmethylated DNA
<220> FEATURE:
<221> NAME/KEY: misc_feature
<222> LOCATION: (1)..(2)
<223> OTHER INFORMATION: n is uracil
<220> FEATURE:
<221> NAME/KEY: misc_feature
<222> LOCATION: (4)..(6)
<223> OTHER INFORMATION: n is uracil
<220> FEATURE:
<221> NAME/KEY: misc_feature
<222> LOCATION: (10)..(10)
<223> OTHER INFORMATION: n is uracil
<220> FEATURE:
<221> NAME/KEY: misc_feature
<222> LOCATION: (15)..(16)
<223> OTHER INFORMATION: n is uracil
<220> FEATURE:
<221> NAME/KEY: misc_feature
<222> LOCATION: (21)..(21)
<223> OTHER INFORMATION: n is uracil
<220> FEATURE:
<221> NAME/KEY: misc_feature
<222> LOCATION: (24)..(24)
<223> OTHER INFORMATION: n is uracil
<220> FEATURE:
<221> NAME/KEY: misc_feature
<222> LOCATION: (26)..(26)
<223> OTHER INFORMATION: n is uracil
<220> FEATURE:
<221> NAME/KEY: misc_feature
<222> LOCATION: (29)..(29)
<223> OTHER INFORMATION: n is uracil

<400> SEQUENCE: 3
nngnnnaaan gggtnnggag ngantngtna                               30

<210> SEQ ID NO 4
<211> LENGTH: 30
<212> TYPE: DNA
<213> ORGANISM: Artificial Sequence
<220> FEATURE:
<223> OTHER INFORMATION: deaminated methylated DNA
<220> FEATURE:
<221> NAME/KEY: misc_feature
<222> LOCATION: (1)..(1)
<223> OTHER INFORMATION: n is uracil
<220> FEATURE:
<221> NAME/KEY: misc_feature
<222> LOCATION: (2)..(2)
<223> OTHER INFORMATION: methylation
<220> FEATURE:
<221> NAME/KEY: misc_feature
<222> LOCATION: (4)..(6)
<223> OTHER INFORMATION: n is uracil
<220> FEATURE:
<221> NAME/KEY: misc_feature
<222> LOCATION: (10)..(10)
<223> OTHER INFORMATION: methylation
<220> FEATURE:
<221> NAME/KEY: misc_feature
<222> LOCATION: (15)..(16)
<223> OTHER INFORMATION: n is uracil
<220> FEATURE:
<221> NAME/KEY: misc_feature
<222> LOCATION: (24)..(24)
<223> OTHER INFORMATION: n is uracil
<220> FEATURE:
<221> NAME/KEY: misc_feature -continued

```
<222> LOCATION: (26)..(26)
<223> OTHER INFORMATION: n is uracil
<220> FEATURE:
<221> NAME/KEY: misc_feature
<222> LOCATION: (26)..(26)
<223> OTHER INFORMATION: methylation
<220> FEATURE:
<221> NAME/KEY: misc_feature
<222> LOCATION: (29)..(29)
<223> OTHER INFORMATION: n is uracil

<400> SEQUENCE: 4
ncgnnnaaac gggtnnggaa cgantngtna                                              30

<210> SEQ ID NO 5
<211> LENGTH: 30
<212> TYPE: DNA
<213> ORGANISM: Artificial Sequence
<220> FEATURE:
<223> OTHER INFORMATION: deaminated unmethylated DNA
<220> FEATURE:
<221> NAME/KEY: misc_feature
<222> LOCATION: (1)..(2)
<223> OTHER INFORMATION: n is uracil
<220> FEATURE:
<221> NAME/KEY: misc_feature
<222> LOCATION: (4)..(6)
<223> OTHER INFORMATION: n is uracil
<220> FEATURE:
<221> NAME/KEY: misc_feature
<222> LOCATION: (10)..(10)
<223> OTHER INFORMATION: n is uracil
<220> FEATURE:
<221> NAME/KEY: misc_feature
<222> LOCATION: (15)..(16)
<223> OTHER INFORMATION: n is uracil
<220> FEATURE:
<221> NAME/KEY: misc_feature
<222> LOCATION: (21)..(21)
<223> OTHER INFORMATION: n is uracil
<220> FEATURE:
<221> NAME/KEY: misc_feature
<222> LOCATION: (24)..(24)
<223> OTHER INFORMATION: n is uracil
<220> FEATURE:
<221> NAME/KEY: misc_feature
<222> LOCATION: (26)..(26)
<223> OTHER INFORMATION: n is uracil
<220> FEATURE:
<221> NAME/KEY: misc_feature
<222> LOCATION: (29)..(29)
<223> OTHER INFORMATION: n is uracil

<400> SEQUENCE: 5
nngnnnaagn gggtnnggaa ngantngtna                                              30

<210> SEQ ID NO 6
<211> LENGTH: 30
<212> TYPE: DNA
<213> ORGANISM: Artificial Sequence
<220> FEATURE:
<223> OTHER INFORMATION: deaminated target DNA
<220> FEATURE:
<221> NAME/KEY: misc_feature
<222> LOCATION: (1)..(1)
<223> OTHER INFORMATION: n is uracil
<220> FEATURE:
<221> NAME/KEY: misc_feature
<222> LOCATION: (1)..(1)
<223> OTHER INFORMATION: methylation
<220> FEATURE:
<221> NAME/KEY: misc_feature
<222> LOCATION: (4)..(6)
<223> OTHER INFORMATION: n is uracil
<220> FEATURE:
```

```
<221> NAME/KEY: misc_feature
<222> LOCATION: (9)..(9)
<223> OTHER INFORMATION: methylation
<220> FEATURE:
<221> NAME/KEY: misc_feature
<222> LOCATION: (15)..(16)
<223> OTHER INFORMATION: n is uracil
<220> FEATURE:
<221> NAME/KEY: misc_feature
<222> LOCATION: (21)..(21)
<223> OTHER INFORMATION: n is uracil
<220> FEATURE:
<221> NAME/KEY: misc_feature
<222> LOCATION: (24)..(24)
<223> OTHER INFORMATION: n is uracil
<220> FEATURE:
<221> NAME/KEY: misc_feature
<222> LOCATION: (25)..(25)
<223> OTHER INFORMATION: methylation
<220> FEATURE:
<221> NAME/KEY: misc_feature
<222> LOCATION: (29)..(29)
<223> OTHER INFORMATION: n is uracil

<400> SEQUENCE: 6
ncgnnnaaac gggtnnggag ngantcgtna                                30

<210> SEQ ID NO 7
<211> LENGTH: 23
<212> TYPE: DNA
<213> ORGANISM: Artificial Sequence
<220> FEATURE:
<223> OTHER INFORMATION: target site probe
<220> FEATURE:
<221> NAME/KEY: misc_feature
<222> LOCATION: (10)..(23)
<223> OTHER INFORMATION: n is any nucleotide of a, g, t or c
<220> FEATURE:
<221> NAME/KEY: misc_feature
<222> LOCATION: (10)..(23)
<223> OTHER INFORMATION: nucleotide residues may be between 8 and 14
      n's in length

<400> SEQUENCE: 7
taacgaatcn nnnnnnnnnn nnn                                       23

<210> SEQ ID NO 8
<211> LENGTH: 10
<212> TYPE: DNA
<213> ORGANISM: Artificial Sequence
<220> FEATURE:
<223> OTHER INFORMATION: target site probe

<400> SEQUENCE: 8
gtttaaacga                                                      10

<210> SEQ ID NO 9
<211> LENGTH: 21
<212> TYPE: DNA
<213> ORGANISM: Artificial Sequence
<220> FEATURE:
<223> OTHER INFORMATION: template strand

<400> SEQUENCE: 9
cttctatagt gtcacctaaa t                                         21

<210> SEQ ID NO 10
<211> LENGTH: 21
<212> TYPE: DNA
<213> ORGANISM: Artificial Sequence
<220> FEATURE:
```

```
<223> OTHER INFORMATION: nontemplate strand

<400> SEQUENCE: 10
atttaggtga cactatagaa g                                              21

<210> SEQ ID NO 11
<211> LENGTH: 12
<212> TYPE: DNA
<213> ORGANISM: Artificial Sequence
<220> FEATURE:
<223> OTHER INFORMATION: telomerase capture probe

<400> SEQUENCE: 11
gggttagggt ta                                                        12

<210> SEQ ID NO 12
<211> LENGTH: 30
<212> TYPE: DNA
<213> ORGANISM: Artificial Sequence
<220> FEATURE:
<223> OTHER INFORMATION: telomerase capture probe

<400> SEQUENCE: 12
gggttagggt tagggttagg gttagggtta                                     30

<210> SEQ ID NO 13
<211> LENGTH: 24
<212> TYPE: DNA
<213> ORGANISM: Artificial Sequence
<220> FEATURE:
<223> OTHER INFORMATION: telomerase capture probe

<400> SEQUENCE: 13
gggttagggt tagggttagg gtta                                           24

<210> SEQ ID NO 14
<211> LENGTH: 24
<212> TYPE: DNA
<213> ORGANISM: Artificial Sequence
<220> FEATURE:
<223> OTHER INFORMATION: complementary probe
<220> FEATURE:
<221> NAME/KEY: misc_feature
<222> LOCATION: (1)..(1)
<223> OTHER INFORMATION: n is uracil
<220> FEATURE:
<221> NAME/KEY: misc_feature
<222> LOCATION: (7)..(7)
<223> OTHER INFORMATION: n is uracil
<220> FEATURE:
<221> NAME/KEY: misc_feature
<222> LOCATION: (13)..(13)
<223> OTHER INFORMATION: n is uracil
<220> FEATURE:
<221> NAME/KEY: misc_feature
<222> LOCATION: (19)..(19)
<223> OTHER INFORMATION: n is uracil

<400> SEQUENCE: 14
naacccnaac ccnaacccna accc                                           24

<210> SEQ ID NO 15
<211> LENGTH: 3621
<212> TYPE: DNA
<213> ORGANISM: Homo sapiens

<400> SEQUENCE: 15
atatactggg tctacaaggt ttaagtcaac cagggattga aatataactt ttaaacagag    60
```

```
ctggattatc cagtaggcag attaagcatg tgcttaaggc atcagcaaag tctgagcaat    120 ccattttta aaacgtagta catgttttg ataagcttaa aaagtagtag tcacaggaaa      180
aattagaact tttacctcct tgcgcttgtt atactcttta gtgctgttta acttttcttt    240
gtaagtgagg gtggtggagg gtgcccataa tcttttcagg gagtaagttc ttcttggtct    300
ttctttcttt ctttctttct ttttttcttg agaccaagtt tcgctcttgt ctcccaggct    360
ggagtgcaat ggcgcgatct cggctcactg caacctccgc cttctcctgg gttcaagcga    420
ttctcctaca tcagcctccg agtagctggg attacaggca tgcgccacca gccccgcta    480 attttgtatt ttttagtaga cagggttt cgccatgttg gtcaggcttg tctcgaactc      540
ctggcctcag gtgatccgcc tgtctcggcc tcccagaatg ctgggattat agacgtgagc    600
caccgcatcc ggacttcct tttatgtaat agtgataatt ctatccaaag cattttttt     660 tttttttgag tcggagtctc attctgtcac ccaggctgga gggtggtggc gcgatctcgg    720
cttactgcaa cctctgcctc ccgggttcaa gcgattctcc tgcctcagcc tcctgagtag    780
ctggaattac acacgtgcgc caccatggcc agctaatttt tgtatttta gtagagacgg     840 ggtgtcacca ttttggccaa gctggcctcg aactcctgac ctcaggtgat ctgcccgcct    900
cggcttccca agtgctggg attacaggtg tgagccaccg cgtcctgctc caaagcattt     960
tctttctatg cctcaaaaca agattgcaag ccagtcctca aagcggataa ttcaagagct   1020
aacaggtatt agcttaggat gtgtggcact gttcttaagg cttatatgta ttaatacatc   1080
atttaaactc acaacaaccc ctataaagca ggggcactc atattccctt cccctttat    1140 aattacgaaa aatgcaaggt attttcagta ggaaagagaa atgtgagaag tgtgaaggag   1200
acaggacagt atttgaagct ggtctttgga tcactgtgca actctgcttc tagaacactg   1260 agcactttt ctggtctagg aattatgact ttgagaatgg agtccgtcct tccaatgact    1320
ccctccccat tttcctatct gcctacaggc agaattctcc cccgtccgta ttaaataaac   1380
ctcatctttt cagagtctgc tcttatacca ggcaatgtac acgtctgaga aacccttgcc   1440
ccagacagcc gttttacacg caggagggga agggagggg aaggagagag cagtccgact    1500
ctccaaaagg aatccttga actagggttt ctgacttagt gaaccccgcg ctcctgaaaa    1560
tcaagggttg agggggtagg gggacacttt ctagtcgtac aggtgatttc gattctcggt   1620
ggggctctca caactaggaa agaatagttt tgcttttct tatgattaaa agaagaagcc    1680
atactttccc tatgacacca aacaccccga ttcaatttgg cagttaggaa ggttgtatcg   1740
cggaggaagg aaacggggcg ggggcggatt tctttttaac agagtgaacg cactcaaaca   1800
cgcctttgct ggcaggcggg ggagcgcggc tgggagcagg gaggccggag ggcggtgtgg   1860
ggggcaggtg gggaggagcc cagtcctcct tccttgccaa cgctggctct ggcgagggct   1920
gcttccggct ggtgccccg ggggagaccc aacctgggc gacttcaggg gtgccacatt     1980
cgctaagtgc tcggagttaa tagcacctcc tccgagcact cgctcacggc gtcccttgc    2040 ctggaaagat accgcggtcc ctccagagga tttgagggac agggtcggag ggggctcttc   2100
cgccagcacc ggaggaagaa agaggagggg ctggctggtc accagagggt ggggcggacc   2160
gcgtgcgctc ggcggctgcg gagaggggga gagcaggcag cgggcggcgg ggagcagcat   2220
ggagccggcg gcggggagca gcatggagcc ttcggctgac tggctggcca cggccgcggc   2280
ccggggtcgg gtagaggagg tgcggcggct gctggaggcg ggggcgctgc ccaacgcacc   2340
gaatagttac ggtcggaggc cgatccaggt gggtagaggg tctgcagcgg gagcagggga   2400
```

```
                                                  -continued tggcgggcga ctctggagga cgaagtttgc aggggaattg gaatcaggta gcgcttcgat    2460
tctccggaaa aaggggaggc ttcctgggga gttttcagaa ggggtttgta atcacagacc    2520
tcctcctggc gacgccctgg gggcttggga agccaaggaa gaggaatgag gagccacgcg    2580
cgtacagatc tctcgaatgc tgagaagatc tgaagggggg aacatatttg tattagatgg    2640
aagtatgctc tttatcagat acaaaattta cgaacgtttg ggataaaaag ggagtcttaa    2700
agaaatgtaa gatgtgctgg gactacttag cctccaattc acagatacct ggatggagct    2760
tatctttctt actaggaggg attatcagtg gaaatctgtg gtgtatgttg gaataaatat    2820
cgaatataaa ttttgatcga aattattcag aagcggccgg gcgcggtgcc tcacgccttg    2880
taatcccttc actttgggag atcaaggcgg ggggaatcac ctgaggtcgg gagttcgaga    2940
ccagcctggc caacaggtga aacctcgcct ctactaaaaa tacaaaaagt agccgggggt    3000
ggtggcaggc gcctgtaatc ccagctactc gggaggttga ggcaggagaa tcgcttgaac    3060
ccgggaggct gaggttgtag tgaacagcga gatggagcca cttcactcca gcctgggtga    3120
cagagtgaga ctttgtcgaa agaaagaaag agagaaagag agagagaaaa attattcaga    3180
agcaactaca tattgtgttt atttttaact gagtagggca aataaatata tgtttgctgt    3240
aggaacttag gaaataatga gccacattca tgtgatcatt ccagaggtaa tatgtagtta    3300
ccattttggg aatatctgct aacatttttg ctctttact atctttagct tacttgatat    3360
agtttatttg tgataagagt tttcaattcc tcattttga acagaggtgt ttctcctctc    3420
cctactcctg ttttgtgagg gagttagggg aggatttaaa agtaattaat acatgggtaa    3480
cttagcatct ctaaaatttt gccaacagct tgaacccggg agtttggctt tgtagtccta    3540
caatatctta gaagagacct tatttgttta aaaacaaaaa ggaaaagaa aagtggatag    3600 ttttgacaat ttttaatgga g                                              3621

<210> SEQ ID NO 16
<211> LENGTH: 64
<212> TYPE: DNA
<213> ORGANISM: Artificial Sequence
<220> FEATURE:
<223> OTHER INFORMATION: capture probe

<400> SEQUENCE: 16
atatactggg tctacaaggt ttaagtcaac cagggattga aatataactt ttaaacagag      60
ctgg                                                                  64

<210> SEQ ID NO 17
<211> LENGTH: 30
<212> TYPE: DNA
<213> ORGANISM: Artificial Sequence
<220> FEATURE:
<223> OTHER INFORMATION: unmethylated DNA template

<400> SEQUENCE: 17
ccgcccaaac gggtccggag cgactcgtca                                      30
```

MOLECULAR DETECTION SYSTEMS UTILIZING REITERATIVE OLIGONUCLEOTIDE SYNTHESIS

CROSS REFERENCE TO RELATED APPLICATIONS

The present application is a divisional of U.S. application Ser. No. 09/984,664, filed Oct. 30, 2001, now U.S. Pat. No. 7,045,319 B2, issued May 16, 2006 and incorporated by reference herein in its entirety.

BACKGROUND OF THE INVENTION

1. Field of the Invention

The present invention relates generally to the detection and kits for the detection of target molecules and, more particularly, to nucleic acid-based detection assays that produce multiple signals from a target molecule by generating multiple copies of detectable oligonucleotides through reiterative synthesis events on a defined nucleic acid template, particularly via abortive transcription initiation. The method and kits of the invention may be used to detect mutations, RNA molecules, pathogens, proteins, or pre-cancerous conditions.

2. Related Art

The development of various methods for nucleic acid detection and the detection of nucleic acid amplification products has led to advances in the detection, identification, and quantification of nucleic acid sequences in recent years. Nucleic acid detection is potentially useful for both qualitative analyses, such as the detection of the presence of defined nucleic acid sequences, and quantitative analyses, such as the quantification of defined nucleic acid sequences. For example, nucleic acid detection may be used to detect and identify pathogens; detect genetic and epigenetic alterations that are linked to defined phenotypes; diagnose genetic diseases or the genetic susceptibility to a particular disease; assess gene expression during development, disease, and/or in response to defined stimuli, including drugs; as well as generally foster advancements in the art by providing research scientists with additional means to study the molecular and biochemical mechanisms that underpin cellular activity.

Nucleic acid detection technology generally permits the detection of defined nucleic acid sequences through probe hybridization, that is, the base-pairing of one nucleic acid strand with a second strand of a complementary, or nearly complementary, nucleic acid sequence to form a stable, double-stranded hybrid. Such hybrids may be formed of a ribonucleic acid (RNA) segment and a deoxyribonucleic acid (DNA) segment, two RNA segments, or two DNA segments, provided that the two segments have complementary or nearly complementary nucleotide sequences. Under sufficiently stringent conditions, nucleic acid hybridization may be highly specific, requiring exact complementarity between the hybridized strands. Typically, nucleic acid hybrids comprise a hybridized region of about eight or more base pairs to ensure the binding stability of the base-paired nucleic acid strands. Hybridization technology permits the use of one nucleic acid segment, which is appropriately modified to enable detection, to "probe" for and detect a second, complementary nucleic acid segment with both sensitivity and specificity. In the basic nucleic acid hybridization assay, a single-stranded target nucleic acid (either DNA or RNA) is hybridized, directly or indirectly, to a labeled nucleic acid probe, and the duplexes containing the label are quantified. Both radioactive and non-radioactive labels have been used.

However, a recognized disadvantage associated with nucleic acid probe technology is the lack of sensitivity of such assays when the target sequence is present in low copy number or dilute concentration in a test sample. In many cases, the presence of only a minute quantity of a target nucleic acid must be accurately detected from among myriad other nucleic acids that may be present in the sample. The sensitivity of a detection assay depends upon several factors: the ability of a probe to bind to a target molecule; the magnitude of the signal that is generated by each hybridized probe; and the time period available for detection.

Several methods have been advanced as suitable means for detecting the presence of low levels of a target nucleic acid in a test sample. One category of such methods is generally referred to as target amplification, which generates multiple copies of the target sequence, and these copies are then subject to further analysis, such as by gel electrophoresis, for example. Other methods generate multiple products from a hybridized probe, or probes, by, for example, cleaving the hybridized probe to form multiple products or ligating adjacent probes to form a unique, hybridization-dependent product. Still other methods amplify signals generated by the hybridization event, such as a method based upon the hybridization of branched DNA probes that have a target sequence binding domain and a labeled reporting sequence binding domain.

There are many variations of target nucleic acid amplification, including, for example, exponential amplification, ligation-based amplification, and transcription-based amplification. An example of an exponential nucleic acid amplification method is the polymerase chain reaction (PCR), which has been disclosed in numerous publications. See, for example, Mullis et al., Cold Spring Harbor Symp. Quant. Biol. 51:263-273 (1986); Mullis et al. U.S. Pat. No. 4,582,788; and Saiki R. et al. U.S. Pat. No. 4,683,194. An example of ligation-based amplification is the ligation amplification reaction (LAR) which is disclosed by Wu et al. in Genomics 4:560 (1989). Various methods for transcription-based amplification are disclosed in U.S. Pat. Nos. 5,766,849 and 5,654,142; and also in Kwoh et al., Proc. Natl. Acad. Sci. U.S.A. 86:1173 (1989).

The most commonly used target amplification method is the polymerase chain reaction (PCR), which consists of repeated cycles of DNA polymerase-generated primer extension reactions. Each reaction cycle includes heat denaturation of the target nucleic acid; hybridization to the target nucleic acid of two oligonucleotide primers, which bracket the target sequence on opposite strands of the target that is to be amplified; and extension of the oligonucleotide primers by a nucleotide polymerase to produce multiple, double-stranded copies of the target sequence. Many variations of PCR have been described, and the method is being used for the amplification of DNA or RNA sequences, sequencing, mutation analysis, and others. Thermocycling-based methods that employ a single primer have also been described. See, for example, U.S. Pat. Nos. 5,508,178; 5,595,891; 5,683,879; 5,130,238; and 5,679,512. The primer can be a DNA/RNA chimeric primer, as disclosed in U.S. Pat. No. 5,744,308. Other methods that are dependent on thermal cycling are the ligase chain reaction (LCR) and the related repair chain reaction (RCR).

Target nucleic acid amplification may be carried out through multiple cycles of incubation at various temperatures (i.e., thermal cycling) or at a constant temperature (i.e., an isothermal process). The discovery of thermostable nucleic acid modifying enzymes has contributed to rapid advances in nucleic acid amplification technology. See, Saiki et al., Science 239:487 (1988). Thermostable nucleic acid modifying enzymes, such as DNA and RNA polymerases, ligases, nucleases, and the like, are used in methods that are dependent on thermal cycling as well as in isothermal amplification-methods.

Isothermal methods, such as strand displacement amplification (SDA) for example, are disclosed by Fraiser et al. in U.S. Pat. No. 5,648,211; Cleuziat et al. in U.S. Pat. No. 5,824,517; and Walker et al., Proc. Natl. Acad. Sci. U.S.A. 89:392-396 (1992). Other isothermal target amplification methods include transcription-based amplification methods in which an RNA polymerase promoter sequence is incorporated into primer extension products at an early stage of the amplification (WO 89/01050), and a further, complementary, target sequence is amplified through reverse transcription followed by physical separation or digestion of an RNA strand in a DNA/RNA hybrid intermediate product. See, for example, U.S. Pat. Nos. 5,169,766 and 4,786,600. Further examples of transcription-based amplification methods include Transcription Mediated Amplification (TMA), Self-Sustained Sequence Replication (3SR), Nucleic Acid Sequence Based Amplification (NASBA), and variations there of. See, for example, Guatelli et al. Proc. Natl. Acad. Sci. U.S.A. 87:1874-1878 (1990) (3SR); U.S. Pat. No. 5,766,849 (TMA); and U.S. Pat. No. 5,654,142 (NASBA).

These and other techniques have been developed recently to meet the demands for rapid and accurate detection of pathogens, such as bacteria, viruses, and fungi, for example, as well as the detection of normal and abnormal genes. While all of these techniques offer powerful tools for the detection and identification of minute amounts of a target nucleic acid in a sample, they all suffer from various problems.

One problem, especially for PCR, is that conditions for amplifying the target nucleic acid for subsequent detection and optional quantitation vary with each test, that is, there are no constant conditions favoring test standardization. Further, amplification methods that use a thermocycling process have the added disadvantage of extended lag times which are required for the thermocycling block to reach the "target" temperature for each cycle. Consequently, amplification reactions performed using thermocycling processes require a significant amount of time to reach completion. The various isothermal target amplification methods do not require a thermocycler and are therefore easier to adapt to common instrumentation platforms. However, the previously described isothermal target amplification methods also have several drawbacks. Amplification according to the SDA methods requires the presence of defined sites for restriction enzymes, which limits its applicability. The transcription-based amplification methods, such as the NASBA and TMA methods, are limited by the need to incorporate a polymerase promoter sequence into the amplification product by a primer.

Accordingly, there is a need for rapid, sensitive, and standardized nucleic acid signal detection methods that can detect low levels of a target nucleic acid in a test sample. These needs, as well as others, are met by the inventions of this application.

All patents, patent publications, and scientific articles cited or identified in this application are hereby incorporated by reference in their entirety to the same extent as if each individual document was specifically and individually indicated to be incorporated by reference in its entirety.

SUMMARY OF THE INVENTION

The invention provides methods and compositions for producing multiple detectable signals through reiterative oligonucleotide synthesis reactions on a defined polynucleotide for the detection of target molecules. The invention also provides applications for the reiterative synthesis and detection methods. Important applications of the methods and kits of the invention, include but are not limited to detection of mutations and single nucleotide polymorphisms, RNA molecules, pathogens, and detection of pre-cancerous or cancerous mutations and conditions.

Accordingly, in one aspect, the invention provides a method for synthesizing multiple complementary oligonucleotides from a target DNA or RNA polynucleotide. The method comprises the steps of: (a) hybridizing an initiator (nucleoside, mononucleotide, oligonucleotide or polynucleotide) with a single-stranded target polynucleotide (RNA or DNA); (b) incubating said target polynucleotide and initiator with an RNA-polymerase, a terminator, and optionally additional ribonucleotides; (c) synthesizing multiple oligonucleotides from said target polynucleotide, wherein said initiator is extended until said terminator is incorporated into said oligonucleotides, thereby synthesizing multiple reiterative oligonucleotides.

In another aspect, the invention provides a method for detecting multiple reiterated oligonucleotides from a target DNA or RNA polynucleotide. The method comprises the steps of (a) hybridizing an initiator with a single stranded target polynucleotide; (b) incubating said target polynucleotide and initiator with an RNA-polymerase, a terminator and optionally additional ribonucleotides; (c) synthesizing multiple oligonucleotides from said target polynucleotide, wherein said initiator is extended until said terminator is incorporated into said oligonucleotides thereby synthesizing multiple reiterative oligonucleotides; and (d) detecting or quantifying said reiteratively synthesized oligonucleotide transcripts of a polynucleotide of interest.

In a further aspect, the invention provides a method of detecting multiple reiterated oligonucleotides from a target DNA or RNA polynucleotide. The method comprises the steps of: (a) hybridizing an initiator to a single-stranded target polynucleotide; (b) incubating said target polynucleotide and initiator with a target site probe, an RNA-polymerase, a terminator and optionally additional ribonucleotides, wherein said target site probe hybridizes with said target polynucleotide; (c) synthesizing an oligonucleotide transcript that is complementary to said target site from said target polynucleotide, wherein said initiator is extended until said terminator is incorporated into said oligonucleotide transcript, thereby synthesizing multiple reiterative oligonucleotide transcripts; and (d) detecting or quantifying said reiteratively synthesized oligonucleotide transcripts, wherein said oligonucleotides being synthesized are one of the lengths selected from the group consisting of: about 2 to about 26 nucleotides, about 26 to about 50 nucleotides and about 50 nucleotides to about 100 nucleotides, and greater than 100 nucleotides.

In a further aspect, the invention provides a method for detecting methylated cytosine residues at CpG sites in a target polynucleotide. The method comprises the steps of: (a) deaminating a single-stranded target DNA sequence under conditions which convert unmethylated cytosine residues to uracil residues while not converting methylated cytosine residues to uracil; (b) hybridizing an initiator with a single stranded target polynucleotide; (c) incubating said deaminated target polynucleotide and said initiator with a terminator, an RNA-polymerase and optionally additional ribonucleotides, wherein at least one of said initiator, terminator, or optional ribonucleotides is modified to enable detection of hybridization to the CG sites; (d) synthesizing an oligonucleotide transcript that is complementary to said CG sites from said target polynucleotide, wherein said initiator is extended until said terminator is incorporated into said oligonucleotide transcript thereby synthesizing multiple reiterative oligonucleotide transcripts; and (e) detecting or quantifying said reiteratively synthesized oligonucleotide transcripts.

In still a further aspect, the invention provides a method for detecting methylated cytosine residues at a CpG site in a target gene. The method comprises the steps of: (a) deaminating a single-stranded target DNA polynucleotide under conditions which convert unmethylated cytosine residues to uracil residues while not converting methylated cytosine residues to uracil; (b) hybridizing a target site probe with said single stranded target polynucleotide; (c) incubating said target polynucleotide and target site probe with, an initiator, a terminator, an RNA-polymerase, and optionally additional ribonucleotides, wherein said at least one of said initiator, said terminator or said nucleotides are complementary to the CpG site; (d) synthesizing an oligonucleotide transcript that is complementary to said target site from said target polynucleotide, wherein said initiator is extended until said terminator is incorporated into said oligonucleotides, thereby synthesizing multiple: reiterative oligonucleotide transcripts; and (e) detecting or quantifying said reiteratively synthesized oligonucleotide transcripts.

In still a further aspect, the invention provides a method for detecting the presence or absence of mutations in a target DNA sequence. The method comprises the steps of: (a) hybridizing a target site probe to a single-stranded DNA polynucleotide, wherein said DNA polynucleotide may contain a mutation relative to a normal or wild type gene; (b) incubating said target polynucleotide and target-site probe with an RNA-polymerase, a initiator, a terminator and optionally additional ribonucleotides; (c) synthesizing an oligonucleotide transcript from said target polynucleotide that is complementary to a target mutation site, wherein said initiator is extended until said terminator is incorporated into said oligonucleotides thereby synthesizing multiple abortive reiterative oligonucleotides; and (d) determining the presence or absence of a mutation by detecting or quantifying said reiteratively synthesized oligonucleotides transcribed from said target DNA polynucleotide.

In another aspect, the invention provides a method for detecting mutations in a target DNA polynucleotide using a capture probe. The method comprises the steps of: (a) immobilizing a capture probe designed to hybridize with said target DNA polynucleotide; (b hybridizing said capture probe to said target DNA polynucleotide, wherein said DNA polynucleotide may contain a mutation relative to a normal or wild type gene; (c) incubating said target polynucleotide and with an RNA-polymerase, initiator, a terminator and optionally additional ribonucleotides; (d) synthesizing an oligonucleotide transcript that is complementary to a target site from said target polynucleotide, wherein said initiator is extended until said terminator is incorporated into said oligonucleotide transcript, thereby synthesizing multiple abortive reiterative oligonucleotide transcripts; and (e) determining the presence or absence of a mutation by detecting or quantifying said reiteratively synthesized oligonucleotide transcripts from said target DNA polynucleotide.

In another aspect, the invention provides a method for detecting DNA or RNA in a test sample. The method comprises the steps of: (a) hybridizing a single stranded target polynucleotide with an abortive promoter cassette comprising a sequence that hybridizes to the single stranded target polynucleotide, and a region that can be detected by transcription by a polymerase; (b) incubating said target polynucleotide with an RNA-polymerase, an initiator, a terminator and optionally additional ribonucleotides; (c) synthesizing an oligonucleotide transcript that is complementary to the initiation start site of the APC, wherein said initiator is extended until said terminator is incorporated into said oligonucleotides, thereby synthesizing multiple reiterative oligonucleotide transcripts; and (d) detecting or quantifying said reiteratively synthesized oligonucleotide transcripts.

In another aspect, the invention provides a method for detecting the presence of pathogens in a test sample. The method comprises the steps of: (a) hybridizing a single stranded target pathogen polynucleotide in said test sample with an abortive promoter cassette comprising a region that can be detected by transcription by a polymerase; (b) incubating said target polynucleotide and initiator with an RNA-polymerase, a terminator and optionally additional ribonucleotides; (c) synthesizing an oligonucleotide transcript that is complementary to initiation start site of the APC, wherein said initiator is extended until said terminator is incorporated into said oligonucleotides thereby synthesizing multiple abortive reiterative oligonucleotide transcripts; and (d) determining the presence of a pathogen by detecting or quantifying said reiteratively synthesized oligonucleotide transcripts synthesized from said test sample.

In still a further aspect, the invention provides a method for detecting pathogens in a test sample using a capture probe. The method comprises the steps of: (a) immobilizing a capture probe designed to hybridize with a target DNA polynucleotide in said test sample; (b) hybridizing said capture probe with a test sample that potentially contains said target DNA polynucleotide; (c) hybridizing a single stranded target DNA polynucleotide in said test sample with an abortive promoter cassette comprising a region that hybridizes to the single stranded target pathogen polynucleotide, and a region that can be detected by transcription by a polymerase; (d) incubating said target polynucleotide with an RNA-polymerase, initiator, a terminator and optionally additional ribonucleotides; (e) synthesizing an oligonucleotide transcript that is complementary to said initiation transcription start site of APC, wherein said initiator is extended until said terminator is incorporated into said oligonucleotides thereby synthesizing multiple reiterative oligonucleotide transcripts; and (f) determining the presence or absence of a pathogen by detecting or quantifying said reiteratively synthesized oligonucleotide transcripts.

In still a further aspect, the invention provides a method for detecting mRNA expression in a test sample. The method comprises the steps of: (a) hybridizing a target mRNA sequence with an abortive promoter cassette comprising a region that can be detected by transcription by a polymerase; (b) incubating said target mRNA sequence with an RNA-polymerase, an initiator, a terminator and optionally additional ribonucleotides; (c) synthesizing an oligonucleotide transcript that is complementary to transcription initiation start site, wherein said initiator is extended until said terminator is incorporated into said oligonucleotide transcript, thereby synthesizing multiple reiterative oligonucleotides; and (d) determining the presence or absence of the mRNA by detecting or quantifying said reiteratively synthesized oligonucleotide transcripts synthesized from said test sample.

In still a further aspect, the invention provides a method for detecting an oligonucleotide synthesized from a target DNA sequence. The method comprises the steps of: (a) hybridizing a DNA primer with a single-stranded target DNA sequence; (b) extending said DNA primer with a DNA polymerase and nucleotides, such that said DNA polymerase reiteratively synthesizes a nucleotide sequence; and (c) detecting oligonucleotide comprised of repeat sequences synthesized by said DNA polymerase.

In still a further aspect, the invention provides a method for producing a microarray. The method comprises the steps of: (a) synthesizing multiple abortive oligonucleotide replicates from a target DNA sequence by the method of claim 1; and (b) attaching said multiple abortive oligonucleotide replicates to a solid substrate to produce a microarray of said multiple abortive oligonucleotide replicates.

In still a further aspect, the invention provides a method for detecting multiple reiterated oligonucleotides from a target DNA or RNA polynucleotide. The method comprises the steps of: (a) incubating a single-stranded target polynucleotide in a mixture comprising an initiator, an RNA-polymerase and optionally additional ribonucleotides; (b) synthesizing multiple oligonucleotide transcripts from said target polynucleotide, wherein said initiator is extended until terminated due to nucleotide deprivation, thereby synthesizing multiple abortive reiterative oligonucleotide transcripts; and (c) detecting or quantifying said reiteratively synthesized oligonucleotides.

In still a further aspect, the invention provides a method of detecting multiple reiterated oligonucleotides from a target DNA or RNA polynucleotide with a target site probe. The method comprises the steps of: (a) incubating a single-stranded target polynucleotide in a mixture comprising an initiator, an RNA-polymerase, a target site probe and optionally additional ribonucleotides, wherein said target site probe and said target polynucleotide hybridize to form a bubble complex comprising a first double-stranded region upstream of a target site, a single-stranded region comprising said target site, and a second double-stranded region downstream of said target site; (b) synthesizing multiple oligonucleotide transcripts from said target polynucleotide, wherein said initiator is extended until terminated due to nucleotide deprivation, thereby synthesizing multiple abortive reiterative oligonucleotides; and (c) detecting or quantifying said reiteratively synthesized oligonucleotide transcripts.

In still a further aspect, the invention provides a method for detecting methylated cytosine residues at a CG site near a target gene. The method comprises the steps of:

(a) deaminating a single-stranded target DNA sequence under conditions which convert unmethylated cytosine residues to uracil residues while not converting methylated cytosine residues to uracil; (b) incubating a single-stranded target polynucleotide in a mixture comprising an initiator, a terminator, an RNA-polymerase, a target site probe and optionally additional ribonucleotides; (c) synthesizing multiple oligonucleotide transcripts from said target polynucleotide, wherein said initiator is extended until terminated due to nucleotide deprivation, thereby synthesizing multiple abortive reiterative oligonucleotide transcripts; and (d) detecting or quantifying said reiteratively synthesized oligonucleotides.

In still a further aspect, the invention provides a method for detecting a target protein in a test sample. The method comprises the steps of: (a) covalently attaching the target protein to an abortive promoter cassette (APC) by a reactive APC linker, wherein said APC comprises a region that can be detected by transcription by a polymerase; (b) incubating said target protein with an RNA-polymerase, an initiator, a terminator and optionally additional ribonucleotides; (c) synthesizing an oligonucleotide transcript that is complementary to transcription initiation start site of APC, wherein said initiator is extended until said terminator is incorporated into said oligonucleotide transcript, thereby synthesizing multiple reiterative oligonucleotide transcripts; and (d) determining the presence or absence of the target protein by detecting or quantifying said reiteratively synthesized oligonucleotide transcripts synthesized from said test sample.

In still a further aspect, the invention provides a method for detecting cancer. The method comprises the steps of: (a) obtaining a tissue sample from a patient in need of detection of a cancer; (b) deaminating the DNA under conditions which convert unmethylated cytosine residues to uracil residues while leaving the methylated cytosine residues unaltered; (c) hybridizing an initiator to a target polynucleotide wherein said initiator is a mononucleoside, mononucleotide, binucleotide, oligonucleotide, polynucleotide, or an analog thereof; (d) incubating said deaminated target polynucleotide and said initiator with a terminator, an RNA-polymerase and optionally additional ribonucleotides, wherein at least one of said initiator, terminator, or optional ribonucleotides is modified to enable detection of hybridization to the CG sites; (e) synthesizing an oligonucleotide transcript that is complementary to said CG sites from said target polynucleotide, wherein said initiator is extended until said terminator is incorporated into said oligonucleotide transcript thereby synthesizing multiple reiterative oligonucleotide transcripts; (f) detecting or quantifying said reiteratively synthesized oligonucleotide transcripts; and (g) comparing the results with those obtained similarly from a control sample.

In still a further aspect, the invention provides a method for detecting pathogens. The method comprises the steps of: (a) obtaining a sample in need of detection of a pathogen; (b) hybridizing a single stranded target pathogen polynucleotide in said sample with an abortive promoter cassette comprising a nucleotide sequence that hybridizes to single stranded target pathogen polynucleotide, and a region that can be detected by transcription by a polymerase; (c) incubating said target polynucleotide and initiator with an RNA-polymerase, a terminator and optionally additional ribonucleotides; (d) synthesizing an oligonucleotide transcript that is complementary to initiation start site of the APC, wherein said initiator is extended until said terminator is incorporated into said oligonucleotides thereby synthesizing multiple abortive reiterative oligonucleotide transcripts; and (e) determining the presence of a pathogen by detecting or quantifying said reiteratively synthesized oligonucleotide transcripts synthesized from said test sample.

The present invention also provides kits for conducting the oligonucleotide synthesis and detection methods described herein. In one aspect, for example, the invention provides reagent containers, which contain various combinations of the components described herein. These kits, in suitable packaging and generally (but not necessarily) containing suitable instructions, contain one or more components used in the oligonucleotide synthesis and detection methods. The kit may also contain one or more of the following items: polymerization enzymes, initiators, primers, buffers, nucleotides, control DNA, antibodies, streptavidin, and biotin. The kit may also contain reagents mixed in appropriate amounts for performing the methods of the invention. The reagent containers preferably contain reagents in unit quantities that obviate measuring steps when performing the subject methods.

BRIEF DESCRIPTION OF THE DRAWINGS

FIG: 1. Abortive Promoter Cassettes. Abortive Promoter Cassettes (APC) are regions of nucleic acid that form a polymerase binding site and can be attached to other macromolecules through interaction with a specific nucleic acid sequence, which is termed the APC linker. APC linkers can be attached to target nucleic acids (DNA or RNA) by hybridization to complementary sequences on either the template or non-template strands of the target nucleic acid. An APC Linker can also hybridize to a complementary sequence placed on any target molecule, such as a protein, for detection of molecules that bind to said protein. Multiple detectable oligonucleotides are generated by polymerase bound to the Abortive Promoter Cassette. In this figure, the APC depicted contains two regions of essential complementarity (A, A' and C, C'), which are separated by a "bubble region." In this schematic, the "bubble region" is generated because regions of the two strands are non-complementary (B, and E). Alternatively, the APC may have two completely complementary strands. Upon binding of the RNA polymerase, the DNA strands separate, which leads to the formation of the "bubble region."

Regions A, B, and C are on one strand. Regions C', E, and A' are on the complementary strand. The APC may be made from two separate strands (ABC and C'EA') or all 6 regions may be on a single polynucleotide, in which regions C and C' are separated by a linker region D, which can modified to be as long as needed. Linker region D may serve only to join C and C' or the sequence of region D may serve as a binding site for other factors that may enhance abortive transcription, such as transcription roadblock proteins, including but not limited to EcoRI QIII mutant, the lac repressor and other RNA polymerases. The linker region D may be designed for a single road block protein, or multiple roadblock proteins. The length of linker region D will depend on the function of the linker region.

Example 1: $R_1$ tag=biotin, $R_2$ tag=fluorescein: detection of fluorescein emission Example 2: $R_1$ tag=DNP, $R_2$ tag=reactive thiol

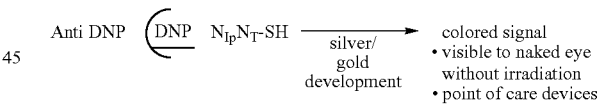

Figure 9:
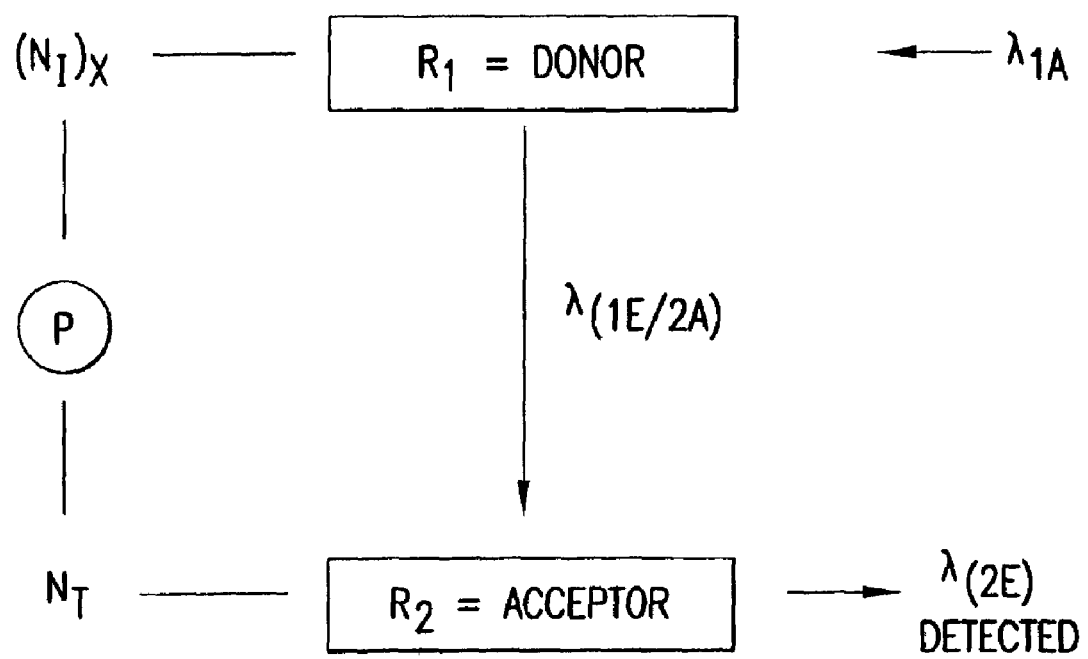

FIG. 9: Signal generation for FRET detection by abortive initiation. Oligonucleotides can be reiteratively synthesized that contain 2 to 25 nucleotides and have two different R groups, one at or near each end of the oligonucleotide product made during transcription. Energy transfer between the two R groups on the substrates can only occur after they are brought into proximity during template-directed oligonucleotide synthesis by enzymatic phosphodiester bond formation between the labeled initiator and the labeled terminator nucleotides. The $R_1$ donor group on $N_1$ can be excited by irradiating the sample with light of wavelength of $\lambda_{1A}$, where $\lambda_{1A}$ is the absorption maximum of group $R_1$. The excited $R_1$ donor group emits light of wavelength $\lambda_{1E}$, where $\lambda_{1E}$ is the emission maximum for group $R_1$ and also a wavelength for absorption by group $R_2$ ($\lambda_{2A}$). The acceptor $R_2$ group on $N_T$ absorbs light of wavelength $\lambda_{1E}/\lambda_{2A}$ that was emitted by the excited $R_1$ donor group on $N_T$. The excited acceptor $R_2$ group on NT emits light of wavelength $\lambda_{2E}$, which is detected and quantified. Similarly, $R_2$ may be an energy donor to $R_1$, with emission from $R_1$ detected. In the absence of target-associated template, no oligonucleotide is synthesized.

Figure 10:
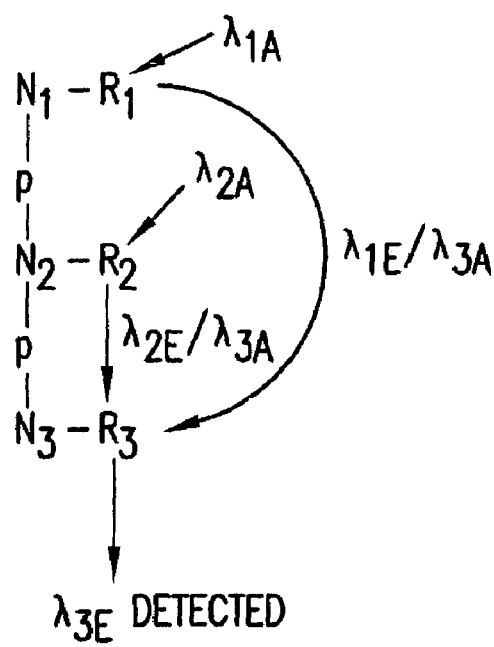

FIG. 10: Trinucleotide energy transfer. Labeled oligonucleotide synthesis is initiated with a labeled dinucleotide initiator. The label may be on either the 5' nucleotide ($R_1$) or the 3' nucleotide ($R_2$) of the dinucleotide initiator. The initiator is elongated with a labeled ($R_3$) 5'-nucleosidetriphosphate terminator nucleotide analog. Detection via energy transfer can be adjusted to utilize $R_1$ or $R_2$ with $R_3$, as shown. In the absence of nucleic acid template-directed phosphodiester bond formation between the initiator and terminator, the R groups remain sufficiently separated that no energy transfer is detected. In this example, the amount of energy emitted as $\lambda_{3E}$ is directly proportional to the amount of template-associated target present. Similarly, the R groups may be varied for other applications, as demonstrated in FIG. 8.

Figure 11:
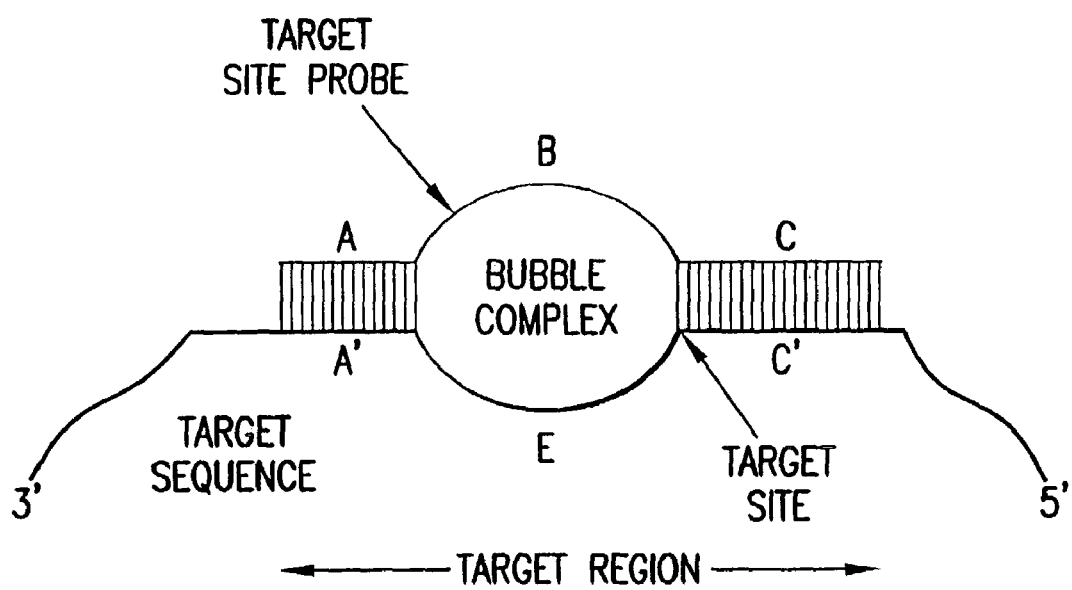

FIG. 11: Target Site Probe. An RNA polymerase can be directed to specific nucleotide positions (sites) in target nucleic acids by the hybridization of a gene-specific or region-specific Target Site Probe (TSP). The target site is a nucleotide position in the DNA to be analyzed for sequence (as in detection of single nucleotide polymorphisms) or structure (as in assessing the methylation status of a specific nucleotide), and it is located on the template strand of the target sequence at the junction of regions E and C' in the target sequence. The TSP contains a region of homology to the target nucleic acid (Region A) which begins approximately 8-14 nucleotides and ends approximately 15-35 nucleotides upstream of the target site nucleotide. A second region of the TSP is designed to be non-complementary to the 8-14 nucleotides immediately upstream of the target site (Region B), so that a melted "bubble" region forms when the TSP hybridizes to the target nucleic acid. The TSP contains a third region (Region C) which is essentially complementary to the 5-25 nucleotides immediately downstream of the target site nucleotide. RNA polymerase will bind to the bubble complex such that transcription will start at the E/C' junction and will move downstream into the C/C' hybrid.

Figure 12:
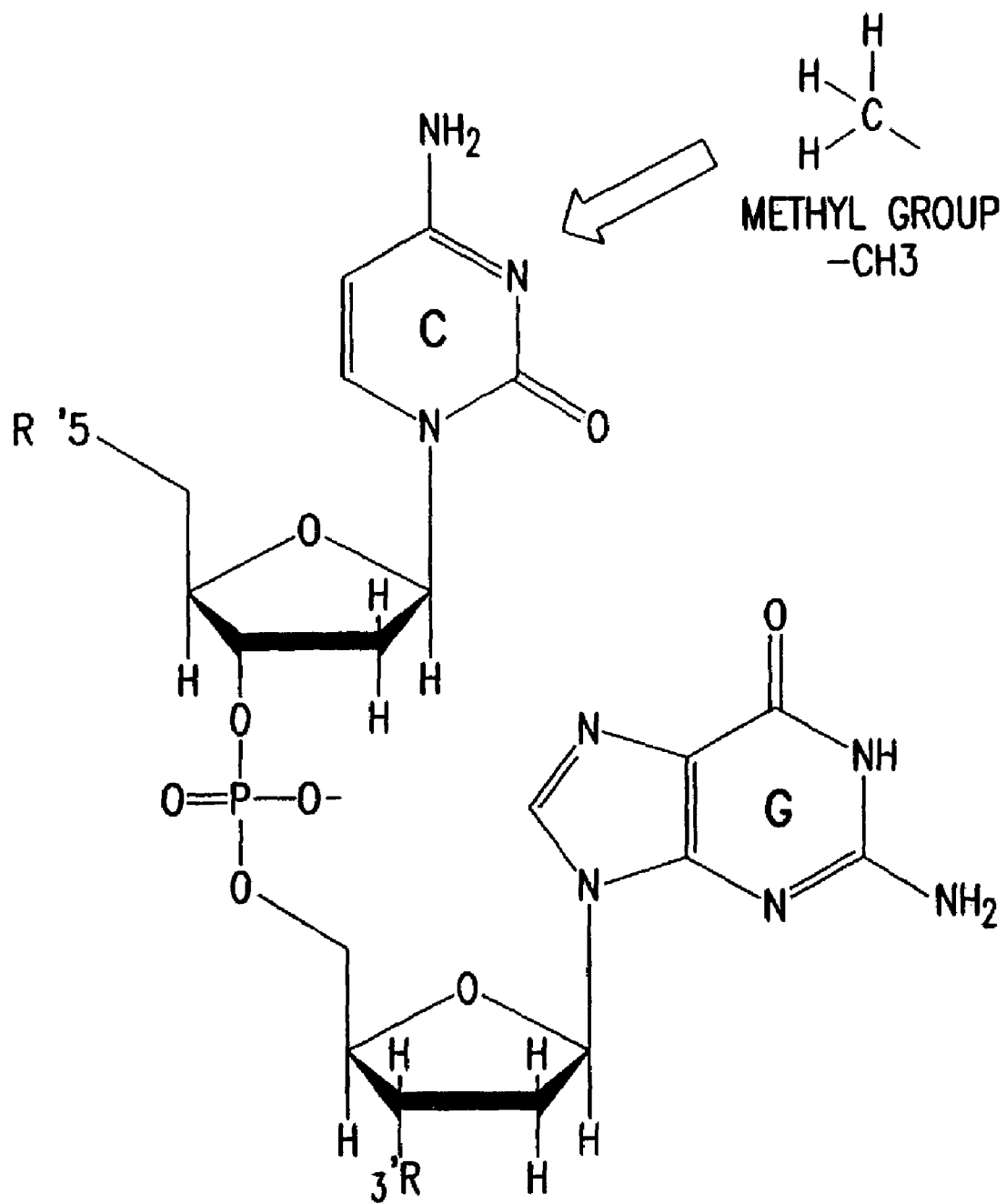

FIG. 12: Methylation of CpG Islands in DNA. The human genome has a 4-5 fold lower frequency of CpG dinucleotides than expected given the overall frequency of C and G in human DNA. A large fraction of CpG sequence is distributed into clusters known as CpG islands. These sequence patterns are between 300-3000 nucleotides long and overlap with about 60% of all human promoters. The remaining CpG dinucleotides outside of CpG islands contain methylated C. CpG methylation outside of CpG islands stabilize the genome by inactivating the expression of parasitic DNA, and independently play an essential role in development. Changes in the methylation status of cytosine in CpG islands are early events in many cancers and permanent changes found in many tumors. These CpG islands are found in the regions next to genes that determine whether the gene is "ON" or "OFF". Many genes that are important for preventing cancer, such as tumor suppressor genes, need to be "ON" for cells to grow normally. Cellular enzymes can add methyl groups (methylation) to the C residues in these CpG islands. This methylation results in the shutting "OFF" of these genes. When tumor suppressor genes are shut "OFF", the cell no longer makes the proteins that they encode, and the cell begins to grow without control checkpoints. This is one of the early events that can lead to cell "transformation" and the progression of cancer.

Figure 13:
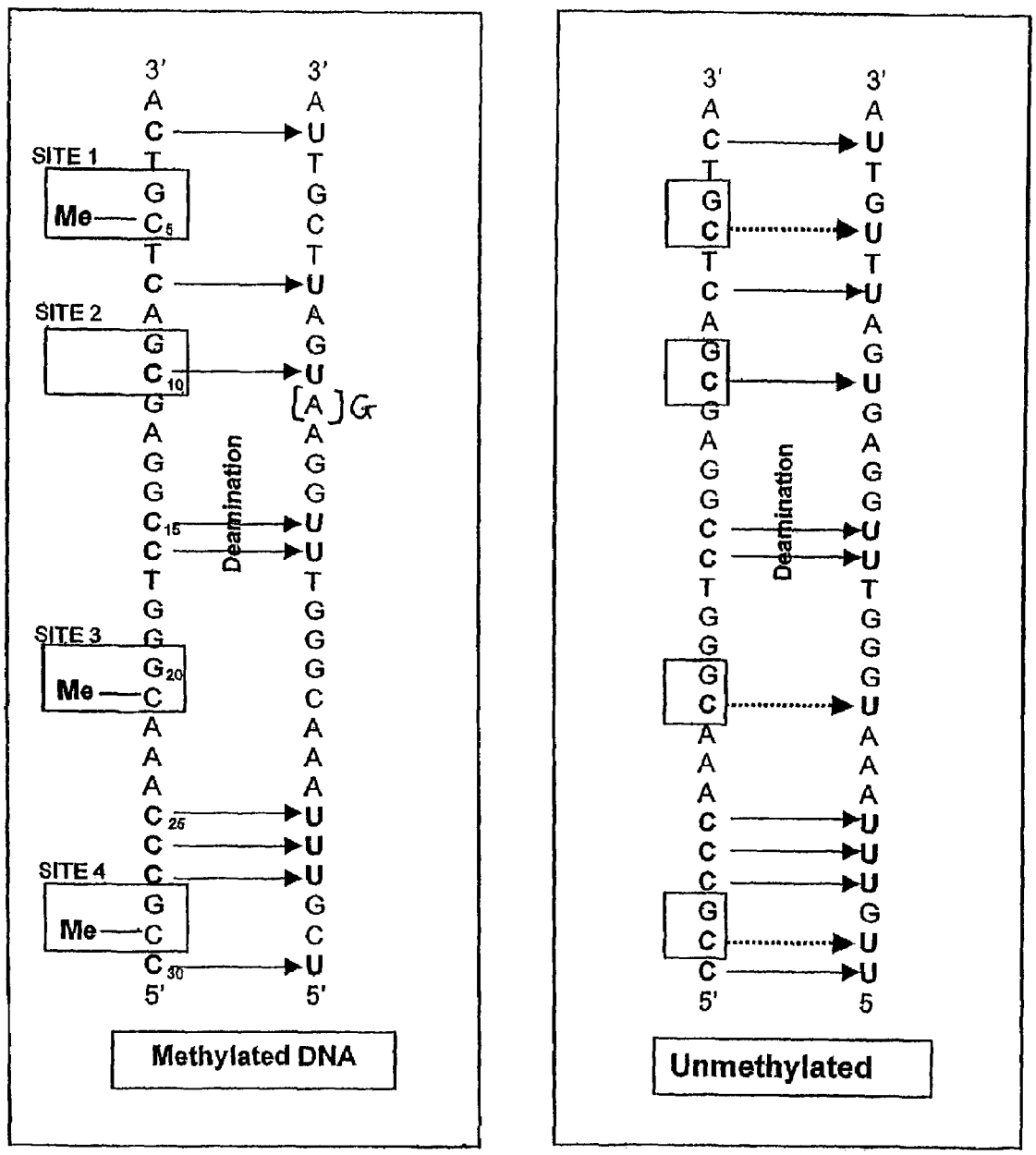

FIG. 13: Deamination conversion of ummethylated cytosine groups in DNA. Deamination converts unmethylated C to U. Methylated C groups, such as those in CpG islands that regulate eukaryotic genes, are resistant to deamination and remain as C in the product DNA. If 100% deamination occurs, methylated DNA will still contain CpG doublets, whereas unmethylated DNA will contain no cytosine and will now contain UpG where CpG doublets were before deamination. This difference in DNA sequence can be used to distinguish between methylated and ummethylated DNA by abortive transcription because the two DNAs encode different dinucleotides. (SEQ ID NOS: 1, 2, 3 and 17).

Figure 14:
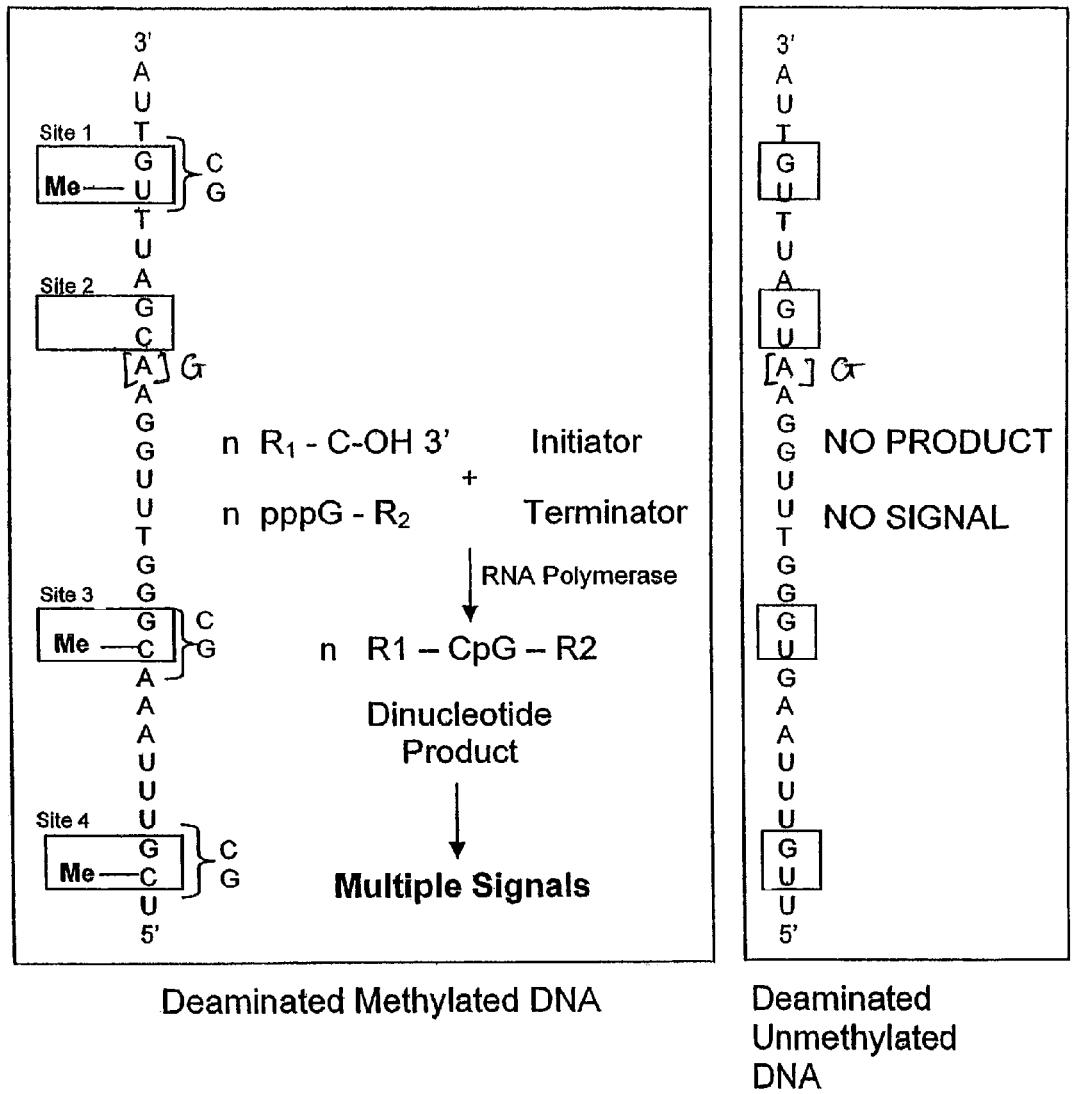

FIG. 14: Detection of methylation using dinucleotide synthesis. Dinucleotide synthesis can be used to assess the overall methylation state of DNA. In the presence of RNA polymerase, CTP or a CTP analog (R1-C-OH), and GTP or a GTP analog (R1-CpG-R2), the deaminated methylated DNA template will produce n copies of a labeled dinucleotide product, where n is proportional to the number of methylated CpG dinucleotides in the starting DNA. The deaminated unmethylated DNA template can produce no dinucleotide with these substrates because the template no longer encodes "C" at any position. SEQ ID NOS: 4 and 5).

If $R_1$ and $R_2$ are appropriately labeled, the dinucleotide will produce a signal that is proportional to the number of methylated CpG sites. For example, if $R_1$ is a fluorescent energy donor or acceptor that is compatible with a second donor or acceptor, $R_2$, a signal will be detected by fluorescent resonance energy transfer (FRET) between $R_1$ and $R_2$ only when the two groups are brought into proximity after incorporation into the dinucleotide in an enzymatic, template-dependent reaction. The reiterative synthesis of these dinucleotides during abortive transcription results in multiple signals from each CpG target and can be used to assess the methylation level of the DNA.

Similarly, abortive synthesis of trinucleotides by transcription initiation with labeled dinucleotides that end in C (ApC, CpC, GpC, UpC) and termination with labeled GTP can be used to produce signal from the deaminated methylated template, but not the deaminated unmethylated template. This trinucleotide synthesis approach may be expanded by the addition of a site-specific oligonucleotide to allow assessment of the methylation status of a specific CpG site, rather than the entire island, as illustrated in FIG. 15.

Figure 15:
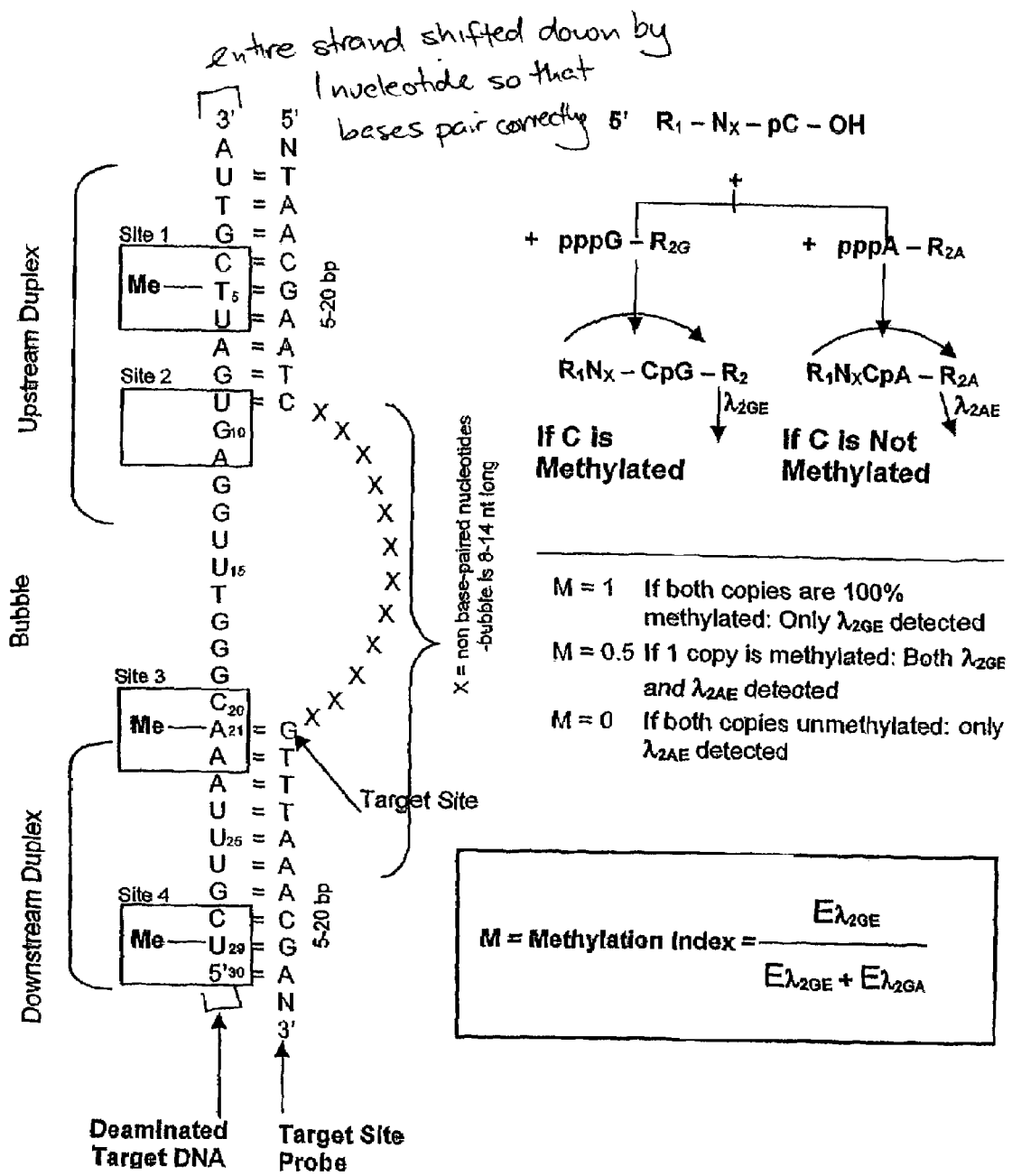

FIG. 15: Assessing methylation status of specific CpG sites in CpG islands by abortive initiation. Target site probes can be used to examine the methylation status of specific CpG islands in specific genes. In the deaminated methylated DNA, the dinucleotide CpG is encoded by the template at the 3 methylated sites 1, 3 and 4, but not by the unmethylated site 2. To specifically determine if Site 3 is methylated and if so, to what extent, position (C21) can be targeted with a Target Site Probe, as described in FIG. 11. The template C in question is positioned at the junction of the bubble region and the downstream duplex so that it encodes the next incorporated nucleotide for appropriately primed RNA polymerase that binds to the bubble region. If a labeled initiator $R_1$-$N_x$pC-OH is used, where $N_x$ may be C for a dinucleotide CpC initiator or $N_x$ may be CpC for a trinucleotide initiator, etc., the initiator can be elongated with a labeled GTP analog pppG-$R_{2G}$ to form a trinucleotide $R_1N_x$CpG-$R_2$. Similarly, if the C in question was not methylated, the position will now be a U and will encode nucleotide A. If an ATP analog pppA-$R_{2A}$ is present, it will be incorporated opposite positions where the C was not methylated. If the GTP analog is labeled with group $R_{2G}$, which is an energy acceptor from the R group on the initiator, $R_1$, then the amount of $R_1N_x$CpG$R_{2G}$, which will be proportional to the amount of methylated C present at that position, can be quantified by measuring the emission from $R_{2G}$ at wavelength $\lambda_{2GE}$. The similar situation exists for incorporation of the ATP analog and measurement of the emission from its R group, also an energy acceptor from the initiator $R_1$. By determining the ratio of the magnitude of emission from the GTP analog to the total emission from both the ATP and GTP analogs, the site can be assigned a methylation index M. If all of the Cs at that position are methylated, M=1. If none of the site is methylated, M=0. (SEQ ID NOS: 6, 7 and 8).

Figure 16:
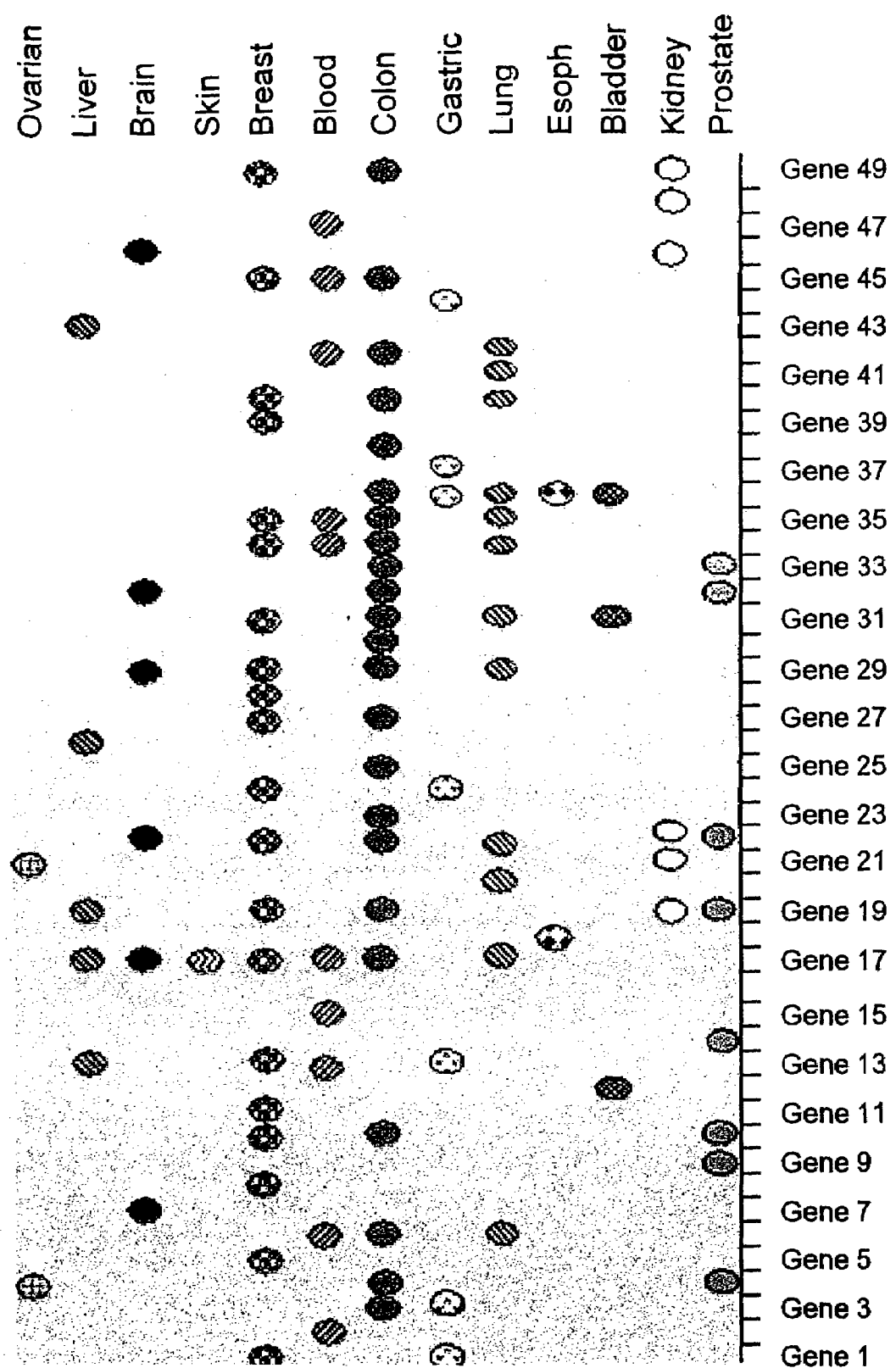

FIG. 16: Genes with altered methylation in cancer. Forty-nine genes with methylation changes associated with cancer initiation and progression are plotted versus 13 cancers. An oval indicates an abnormal methylation status for a gene, coded by cancer type. Cancer is actively prevented through the expression of close to 100 tumor-suppressor genes that regulate the cell-division cycle. CpG methylation potentially is a powerful biomarker for cancer detection. Examination of the promoters of tumor suppressor genes from tumor biopsies suggests that CpG methylation is common enough to equal the impact of mutagenesis in tumor promotion. At least 60 tumor suppressor and repair genes are associated with abnormally high levels of CpG methylation across virtually all of the common tumor types. In virtually all cases, defective expression of tumor suppressor genes begins at an early stage in tumor progression. Detection of these early methylation events before advanced symptoms appear should improve the chances that a cancer will be treated while it is highly curable. CpG methylation patterns are frequently biased to particular genes in particular types of cancers. Therefore, it should be possible to develop methylation signatures for common cancers, indicating both cancer type and stage. Data on the methylation status of multiple promoters could give clues as to the location of a tumor in cases where several organs can contribute to a sample. For example, shed bladder, kidney or prostate cells can populate a urine sample. Tumors from each of these tissues are frequently associated with distinct combinations of CpG island methylation.

Figure 17:
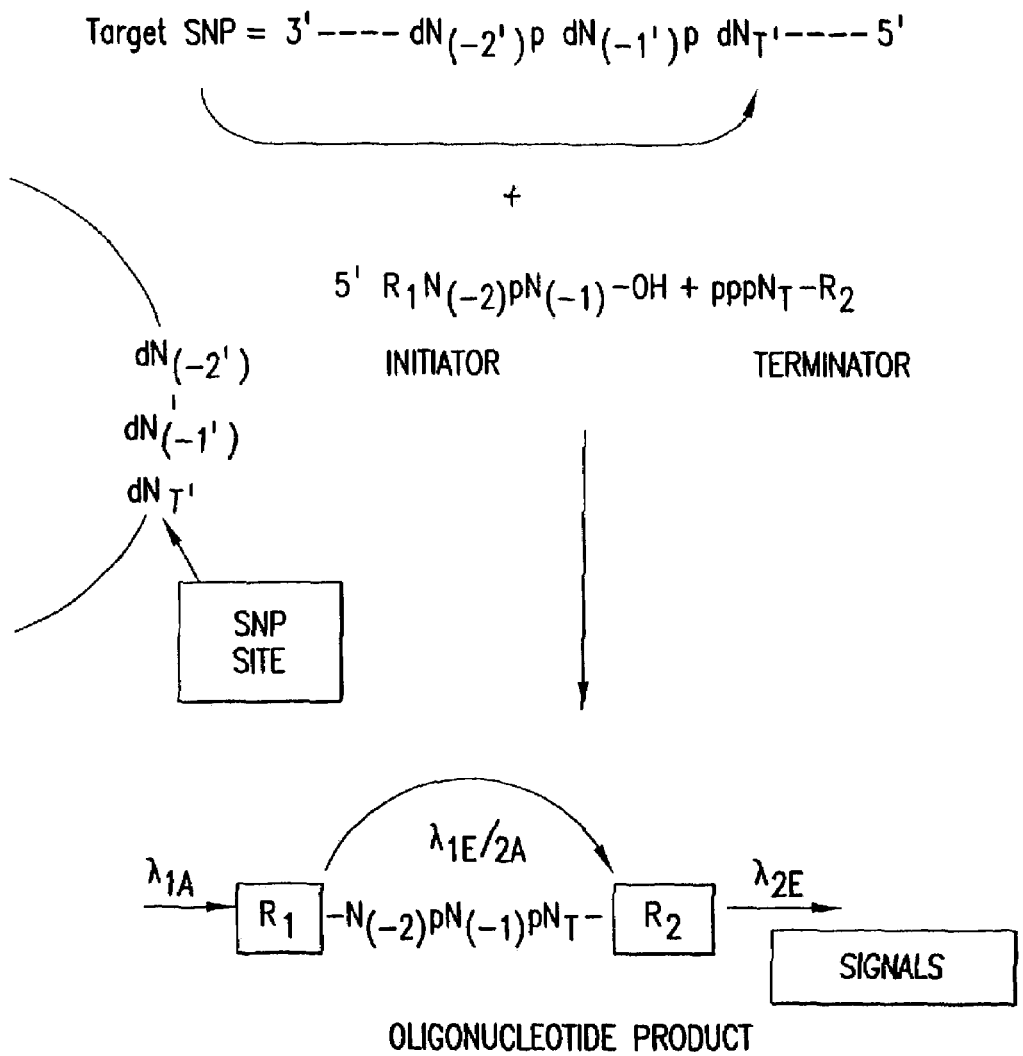

FIG. 17: Single nucleotide polymorphism detection by abortive oligonucleotide synthesis. The identity of a nucleotide at a specific position can also be determined by abortive initiation in the presence of target nucleic acid and a position-specific Target Site Probe. This can be applied to SNP identification by initiating transcription with an oligonucleotide complementary to the DNA upstream from the SNP site. For example for synthesis of a trinucleotide, the dinucleotide initiator would be complementary to the know nucleotides at positions −1 and −2, relative to the SNP site.

Figure 18:
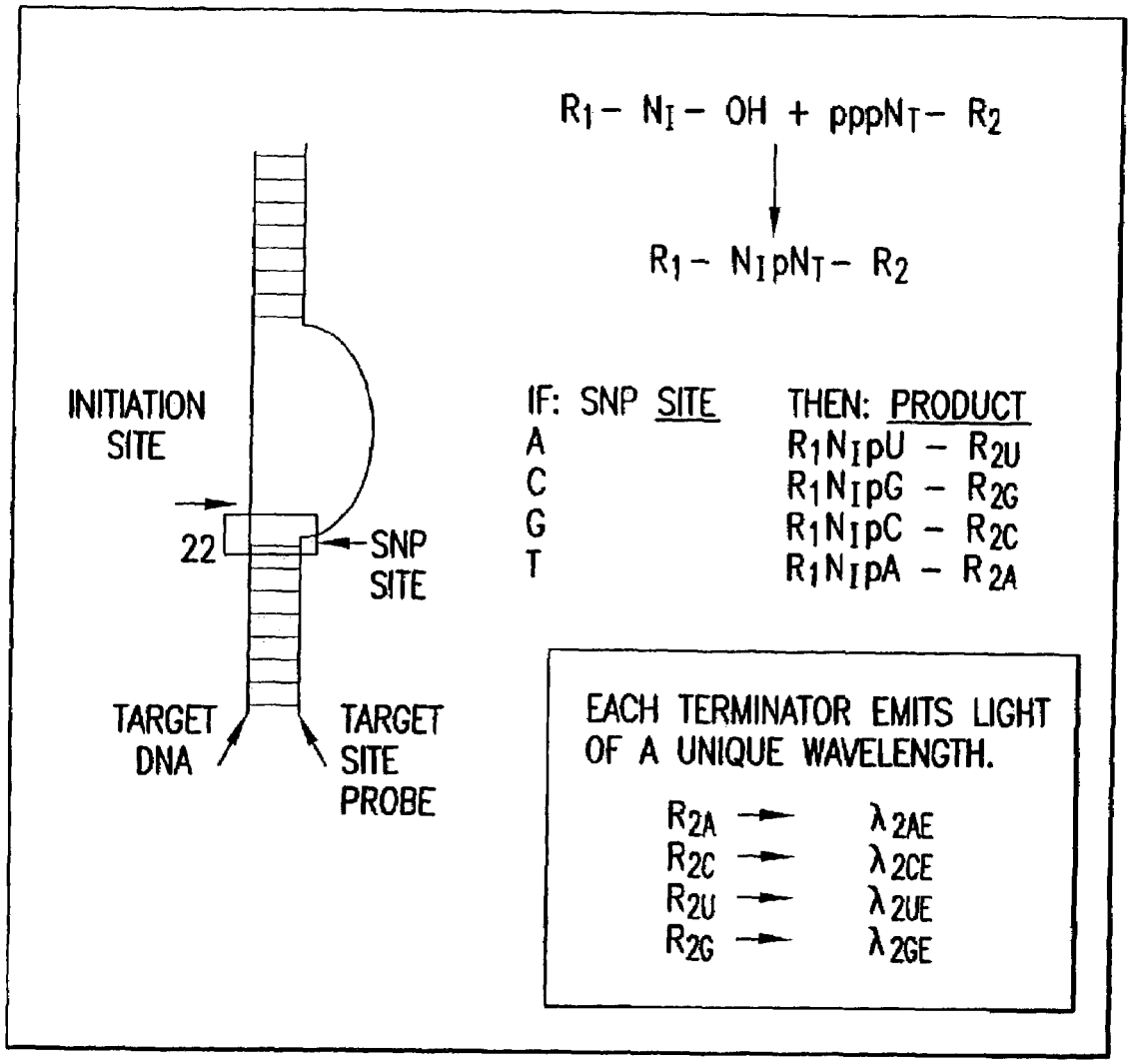

FIG. 18: Detection and identification of single nucleotide polymorphisms (SNPs) by abortive transcription. The identity of a specific DNA nucleotide (A,C,G,T/dU) can be identified by abortive transcription with the use of a Target Site Probe (TSP). For example, to determine whether a DNA contains a normal nucleotide (wild type) or a mutant nucleotide (point-mutation, single nucleotide polymorphism/SNP), a gene-specific TSP can be added to target DNA (or amplification/replication product) such that the SNP position corresponds to the last nucleotide in the C/C' hybrid at the junction of the downstream duplex and the bubble region. A labeled initiator oligonucleotide ($R_1NI$-OH) that is complementary to the region upstream of the SNP site can be elongated by an RNA polymerase to add the next encoded nucleotide, corresponding to the SNP. The labeled terminators (ppp$N_T$-$R_2$ or pppU-$R_{2U}$, pppA-$R_{2A}$, pppC-$R_{2C}$, pppG-$R_{2G}$) can each be labeled with different R groups, for example, $R_{2A}$, $R_{2C}$, $R_{2G}$ and $R_{2U}$ could each be resonance energy acceptors from $R_1$, with each emitting light with a different detectable wavelength.

Figure 19:
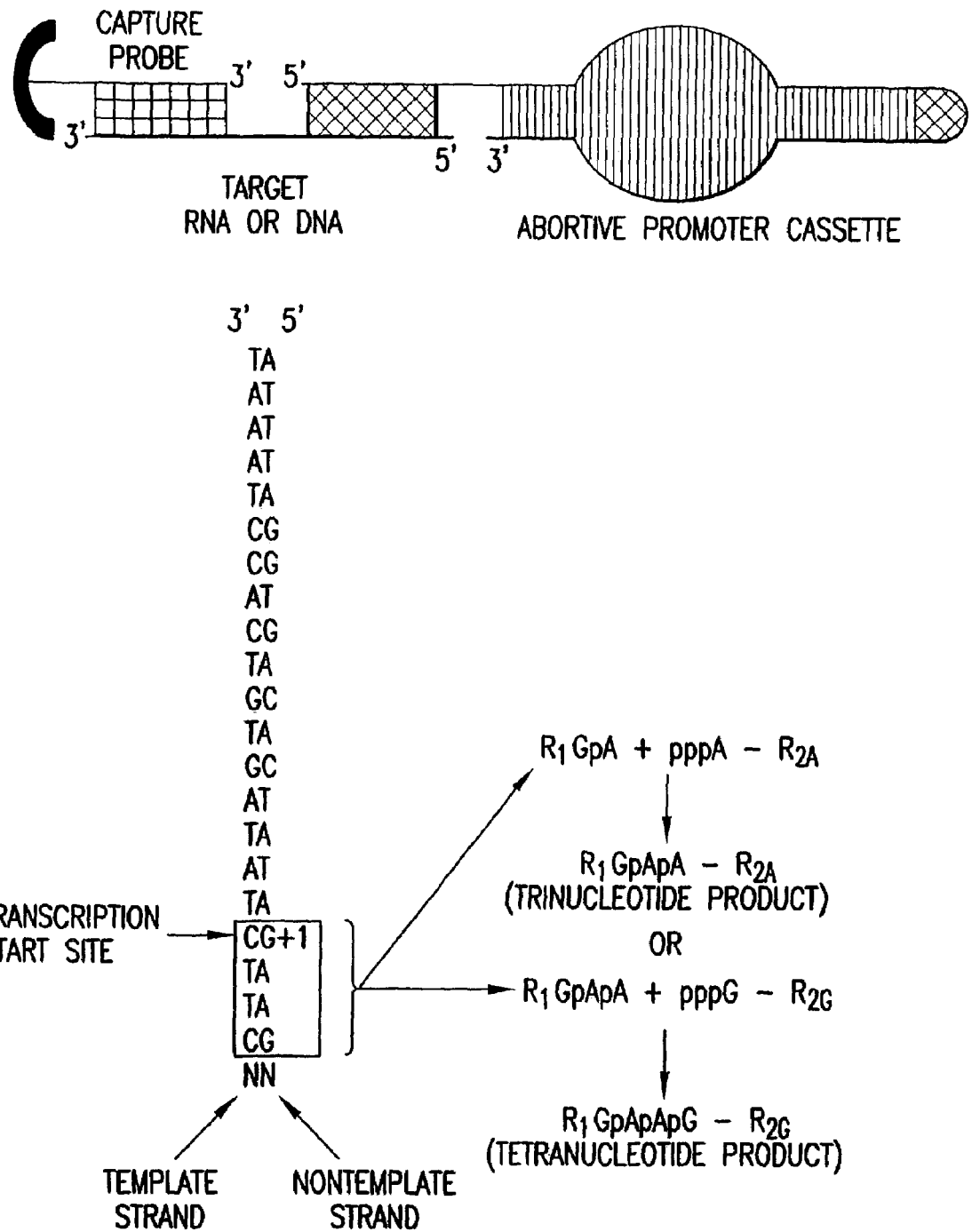

FIG. 19: Signal Generation from abortive promoter. An Abortive Promoter Cassette (APC) consists of one or more oligonucleotides or polynucleotides that together create a specific binding site for an RNA polymerase coupled to a linker region (APC linker) for attachment to target molecules (DNA, RNA, Protein). The APC may contain an artificial promoter, or it may contain the promoter for a specific RNA polymerase. For example, trinucleotide or tetranucleotide products that could be generated from with a common phage RNA polymerase can be made with a labeled GpA or GpApA initiator and a labeled pppG or pppA terminator. (SEQ ID NOS: 9 and 10).

Figure 20:
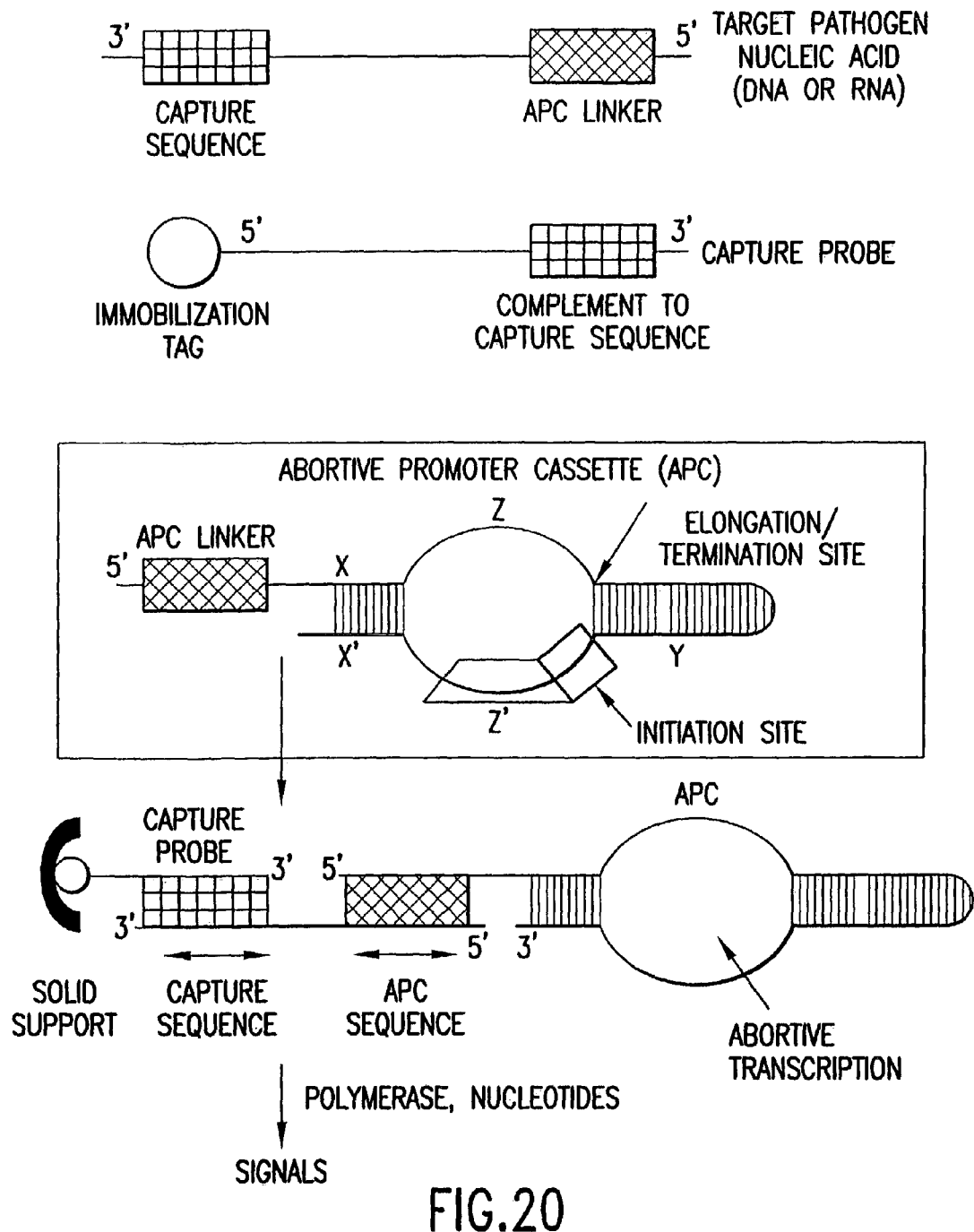

FIG. 20: Detection of nucleic acids by abortive transcription. For detection of nucleic acids, such as DNA or RNA associated with specific diseases or with viral and bacterial pathogens, one can either detect the nucleic acid directly or after replication or primer extension. In the first case, the APC linker in the Abortive Promoter Cassette would be designed to be complementary to a known DNA or RNA sequence of the target nucleic acid. Alternatively, one or more copies of the target DNA or cDNA copies of target RNA can be made by primer extension or reverse transcription initiated with primers containing a universal APC linker sequence at the 5' end. In either case, the target DNA or RNA can be retrieved from the sample by attachment to a solid support, for example, to which an oligonucleotide that contains a second target-specific sequence, which is termed a "capture sequence," has been attached via any number of immobilization tags, including but not limited to biotin, hexahistidine or any other hapten. Once attached, abortive transcription is initiated by addition of a polymerase and the appropriate labeled nucleotides, which results in signal generation, as previously described.

Figure 21:
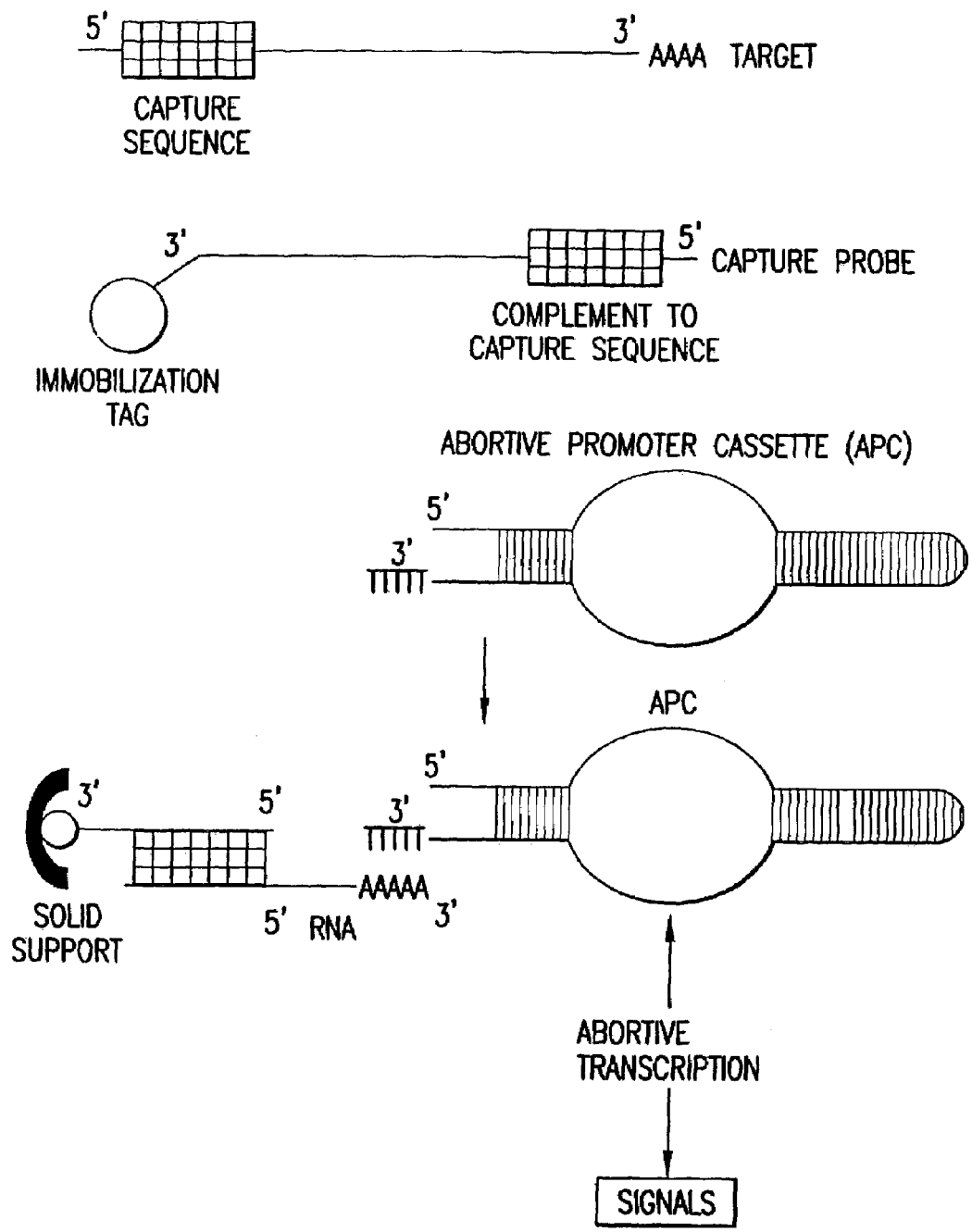

FIG. 21: Detection of mRNA by Abortive Transcription. An Abortive Promoter Cassette for detection of mRNA will contain as its APC linker an oligo T tail. This tail is complementary to the poly A tail found at the 3' end of eukaryotic mRNAs and will be used for attachment of the APC to the target mRNA. The target mRNA can be retrieved from a sample by attachment to an immobilized capture probe containing a capture sequence, which is complementary to some region of the target mRNA.

Figure 22:
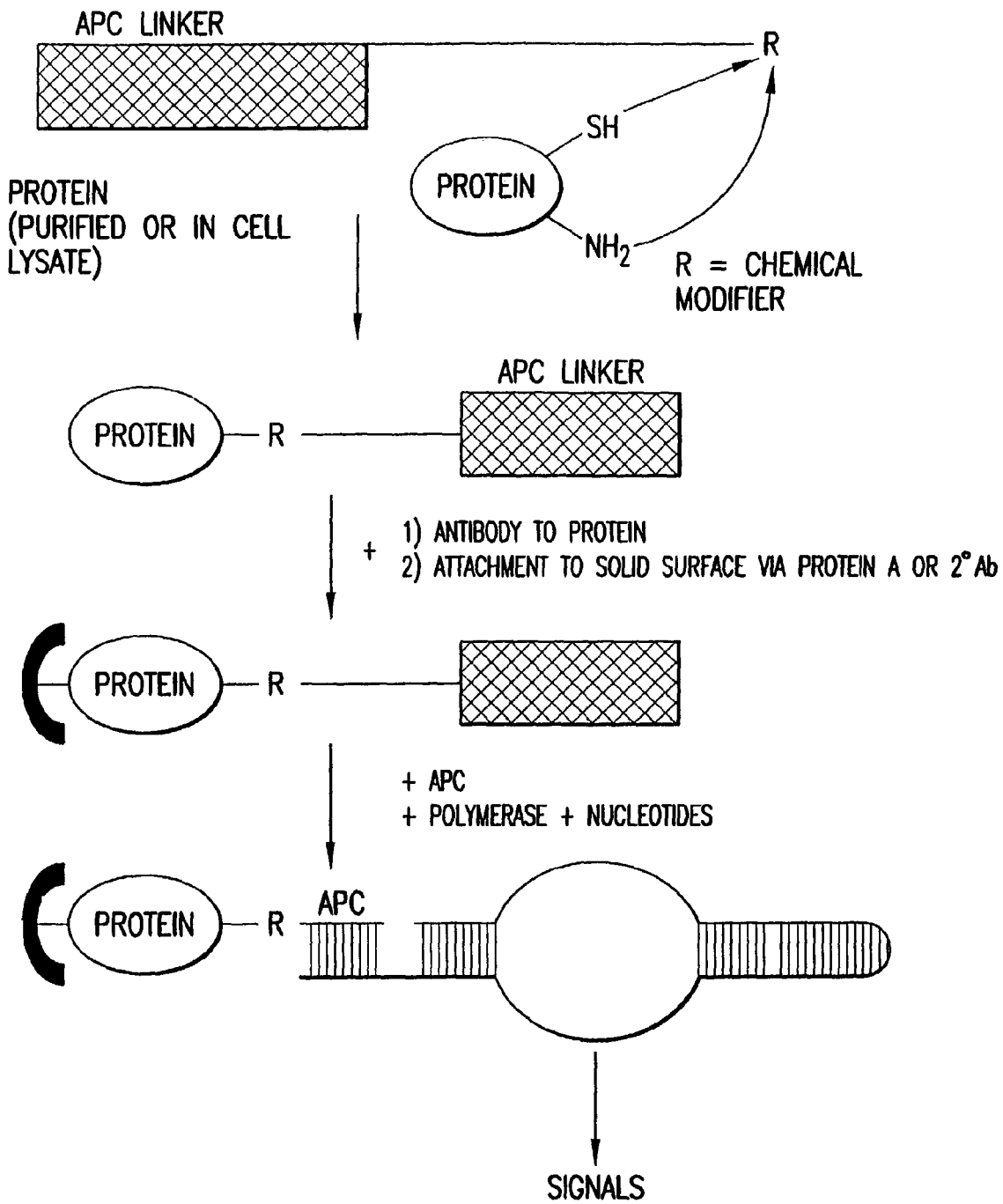

FIG. 22: Detection of proteins or other haptens/antigens with abortive transcription. Signal generation via abortive initiation from an Abortive Promoter Cassette can be used to detect other molecules, such as proteins. For example, an APC linker sequence can be prepared to which thiol-reactive or amine-reactive protein crosslinking agents R will be covalently attached. The reactive APC linker will be added to the target protein, which may be purified or in a complex mixture (such as a cell lysate), and the APC linker will be covalently attached to the target protein via modification of protein thiol and/or amine groups. The labeled protein can then be immobilized utilizing a target-specific probe (such as an antibody). The Abortive Promoter Cassette is then attached via the APC linker, and signal is generated, as previously described.

Figure 23:
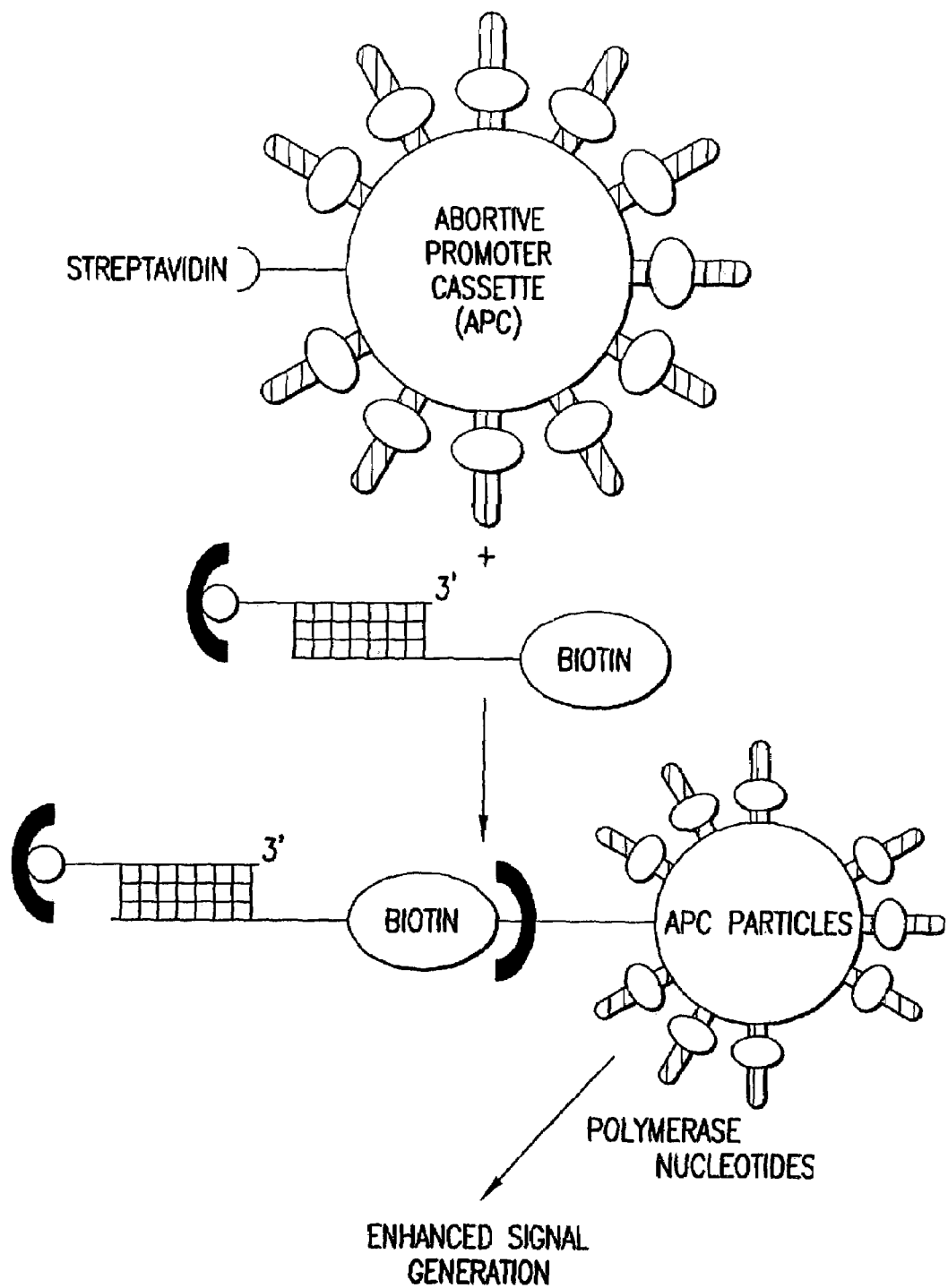

FIG. 23: Enhanced detection of molecular targets via abortive transcription on APC particles. Even greater detection sensitivity can be achieved with the use of particles to which multiple copies, including tens, hundreds, thousands, tens of thousands or even more of the Abortive Promoter Cassette (APC) have been attached. The sphere will also contain a linker that will be specific for binding to a group that can be attached to the target molecule. For example, streptavidin (SA) can be attached to the APC particles and biotin to the target molecule, which can then be immobilized via interaction with a target-specific capture probe. Once the APC particles interact with the target, for example via the SA-biotin interaction, polymerase and labeled nucleotides can be added for signal generation, as described.

Figure 24:
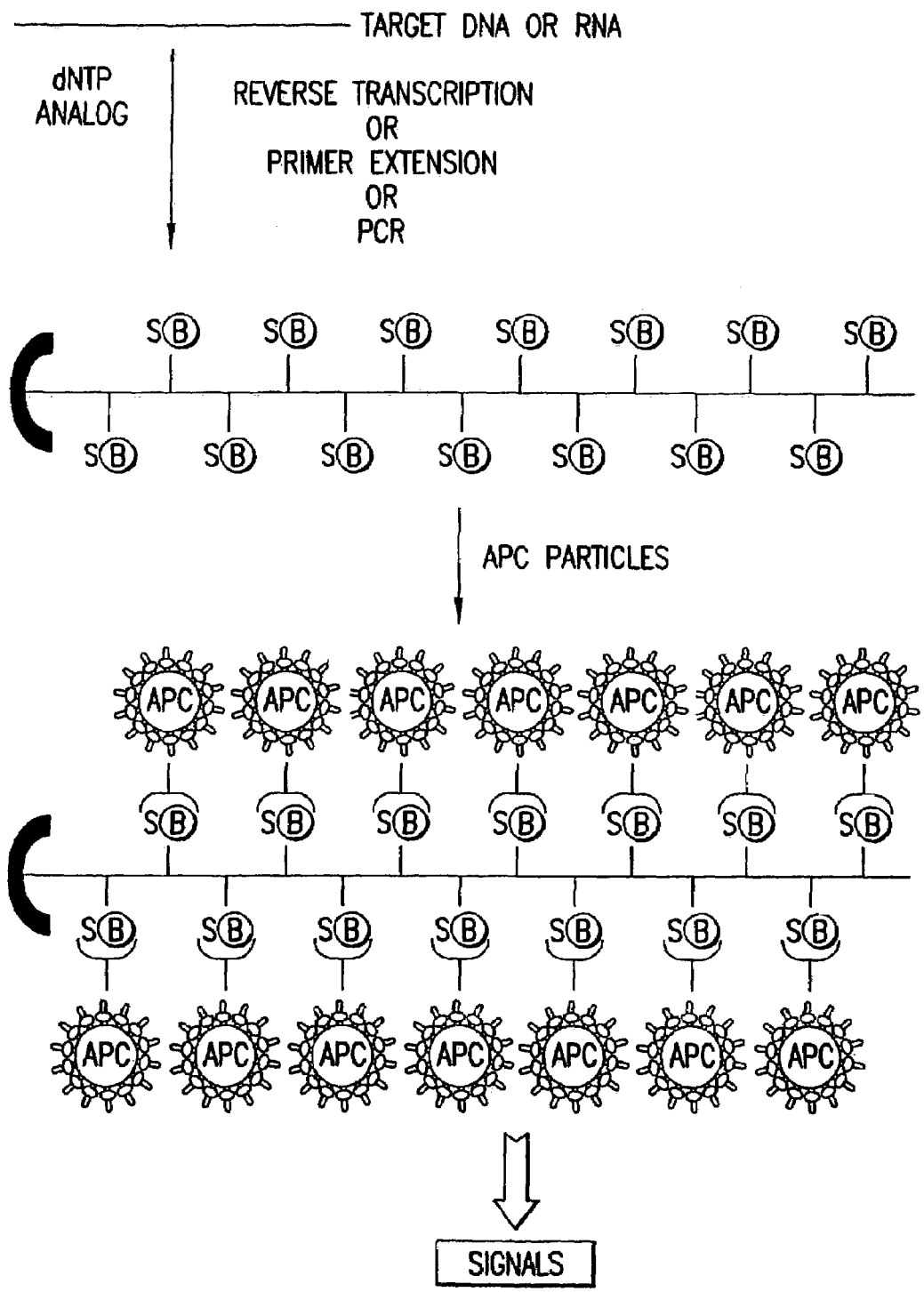

FIG. 24: Coating of DNA or RNA targets with APC particles for ultra-sensitive detection or molecular imaging. An alternative method for the ultra-sensitive detection or visualization of target DNA or RNA can be achieved by reverse transcription of target RNA or copying (single copy or amplification) of target DNA in the presence of probe labeled dNTP analogs. As an example. 5-SH-dUTP can be incorporated at very high frequency in DNA molecules, which can then be immobilized and further modified with other groups, such as biotin. To this, APC particles can be added, as described in FIG. 23, each of which will interact with a nucleotide analog on the target. This essentially coats the target DNA or RNA with APC particles capable of generating multiple oligonucleotide products for a variety of methods of molecular detection.

Figure 25:
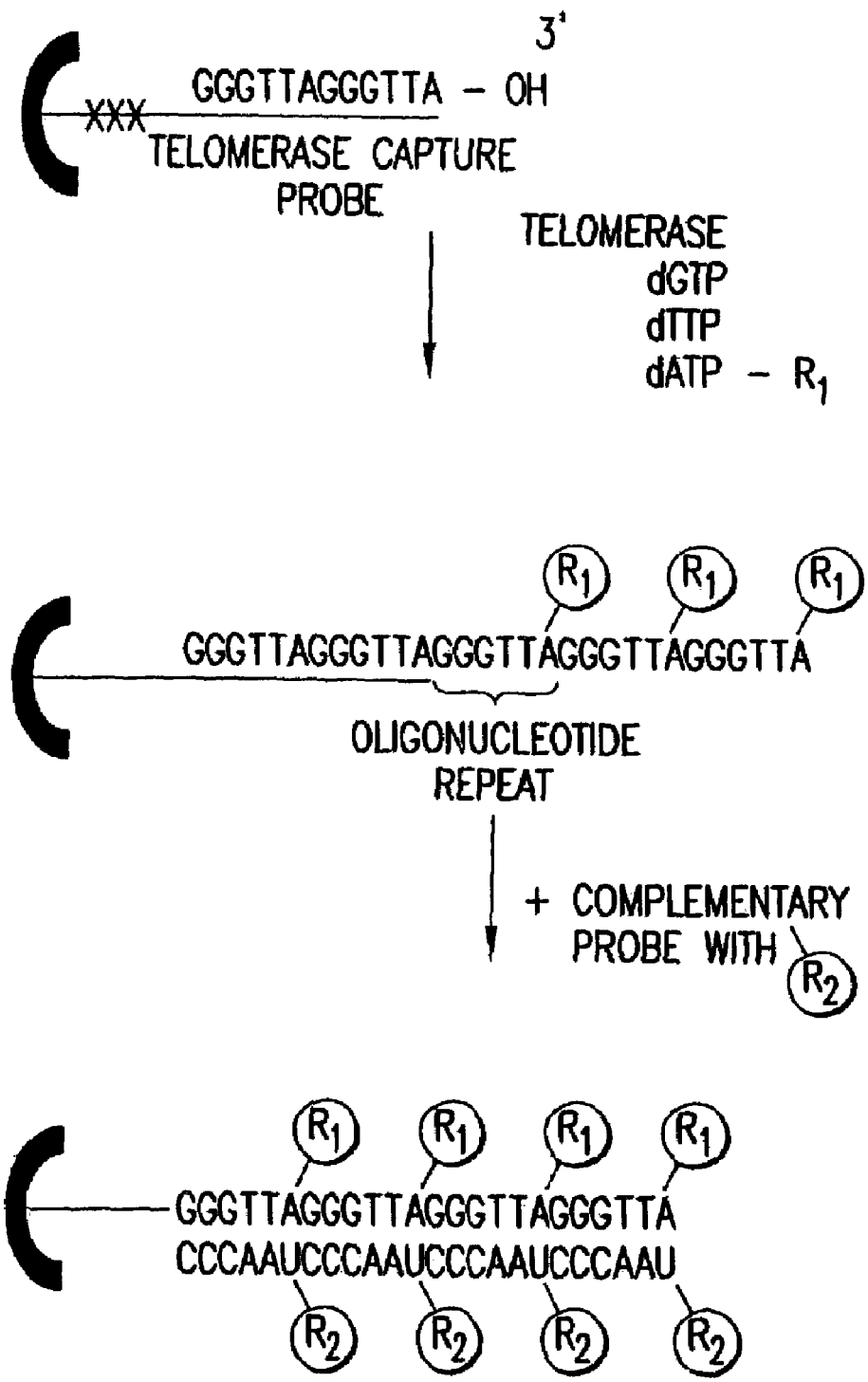

FIG. 25. Detection of telomerase activity with reiterative oligonucleotide synthesis. Reiterative oligonucleotide synthesis with DNA polymerases can also be used for signal generation, however, the product oligonucleotides need not be released, but may be joined tandemly in the product. As an example, telomerase activity can be detected by immobilizing a telomerase-specific probe to a solid matrix to capture cellular telomerase, which carries its own RNA template for DNA synthesis. For example, with human telomerase, the RNA template on the enzyme encodes the DNA sequence GGGTTA. The capture probe may contain the sequence GGGTTA, which will be added reiteratively to the end of the telomerase capture probe, if telomerase is present in the sample. Signal generation can be achieved in several ways, one of which involves including one or more reporter tagged dNTPs in the synthesis reaction to produce a product that has multiple $R_1$ groups attached along the backbone of the DNA product. For detection, this product can then be hybridized to a complementary probe containing nucleotides with a second R group ($R_2$) attached that will hybridize to the $R_1$ labeled product. This will bring the $R_1$ and $R_2$ groups together for signal generation via FRET from between $R_1$ and $R_2$, or via other methods. Alternatively, telomerase may incorporate 2 labeled nucleotides in the product DNA and look for energy transfer between the 2 labeled nucleotides in the single strand of DNA. (SEQ ID NOS: 11, 12, 13 and 14).

Figure 26:
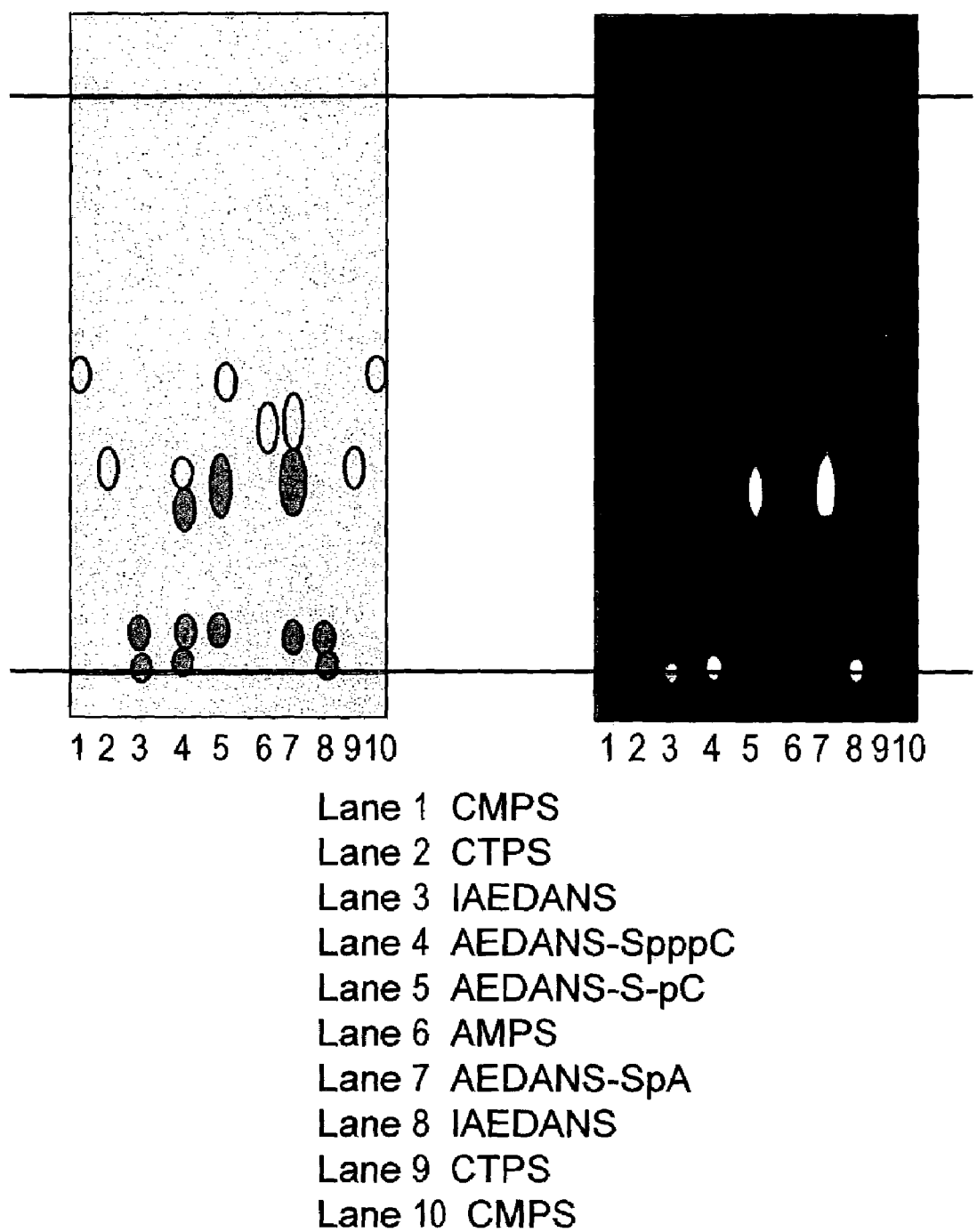

FIG. 26. Synthesis of a dye labeled initiator. 5'EADANS-S-CMP was synthesized from the conjugation of IAEDANS and α-S-CMP. The scanned image of the thin layer chromatography plate shows the control IAEDANS and the IAEDANS labeled product. Lane 1: Cytidine-5'-O-(1-Thiomonophosphate); Lane 2: Cytidine-5'-O-(1-Thiotriphosphate); Lane 3: 5-((((2-iodoacetyl)amino)ethyl)amino)naphthalene-1-sulfonic acid (1,5-IAEDANS); Lane 4: Cytidine-5'-O-(1-Thiotriphosphate) and (1,5-IAEDANS); Lane 5: Cytidine-5'-O-(1-Thiomonophosphate) and (1,5-IAEDANS); Lane 6: Adenosine-5'-O-(1-Thiomonophosphate); Lane 7: Adenosine-5'-O-(1-Thiomonophosphate) and (1,5-IAEDANS); Lane 8: (1,5-IAEDANS); Lane 9: Cytidine-5'-O-(1-Thiotriphosphate); Lane 10: Cytidine-5'-O-(1-Thiomonophosphate). Lanes 4, 5, and 7 also contain 1 U of *E. coli* RNA polymerase, Buffer T and 150 ng of denatured pBR322

Figure 27:
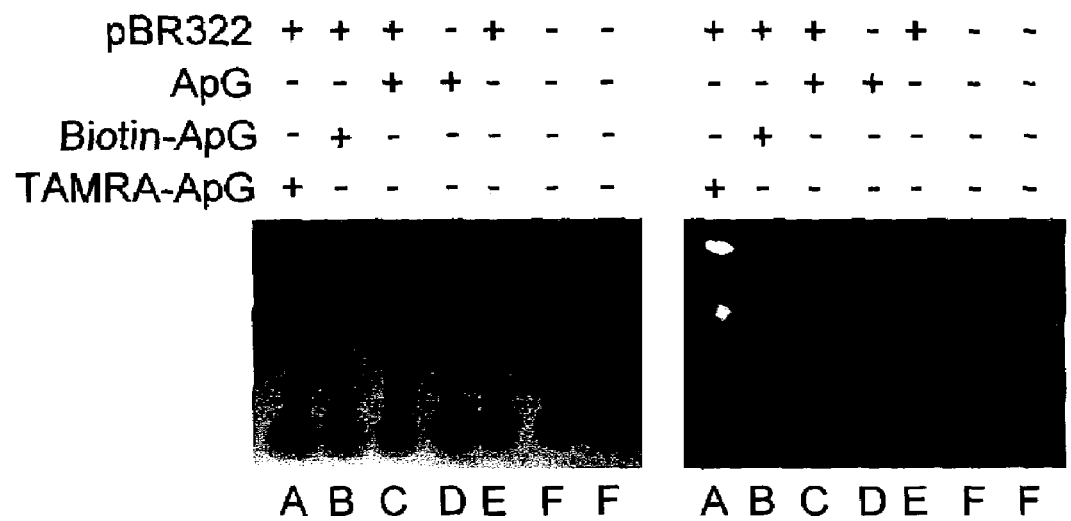

FIG. 27. Abortive Transcription Initiation with labeled initiators. The photograph of the gel shows the results of an abortive transcription initiation reaction using three different dinucleotide initiators, which were (1) ApG; (2) Biotin-ApG; and (3) 5' TAMRA-SpApG, and a terminating nucleotide, which was $\alpha^{32}$P-UTP. All three dinucleotides allowed for incorporation of UTP in the $3^{rd}$ position to generate 5' TAMARA-SpApGpU. The unlabeled ApG incorporates more efficiently than does the Biotin-ApG, which incorporates more efficiently than the TAMARA-ApG.

Figure 28:
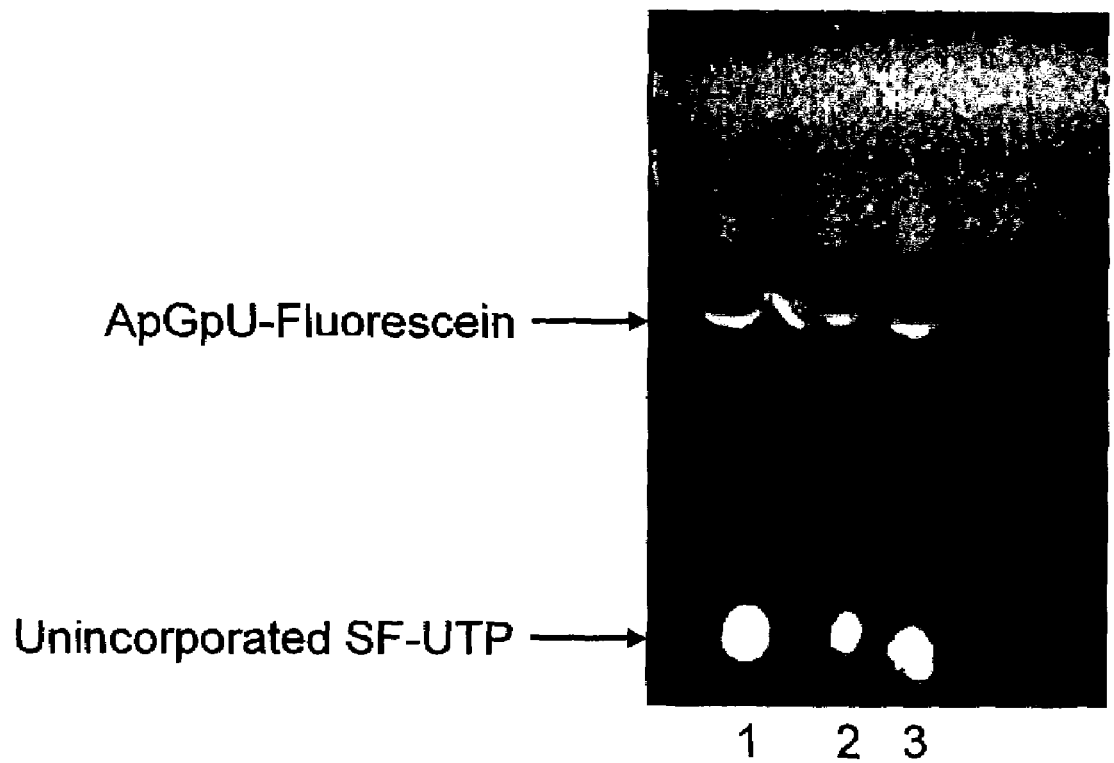
Figure 30:
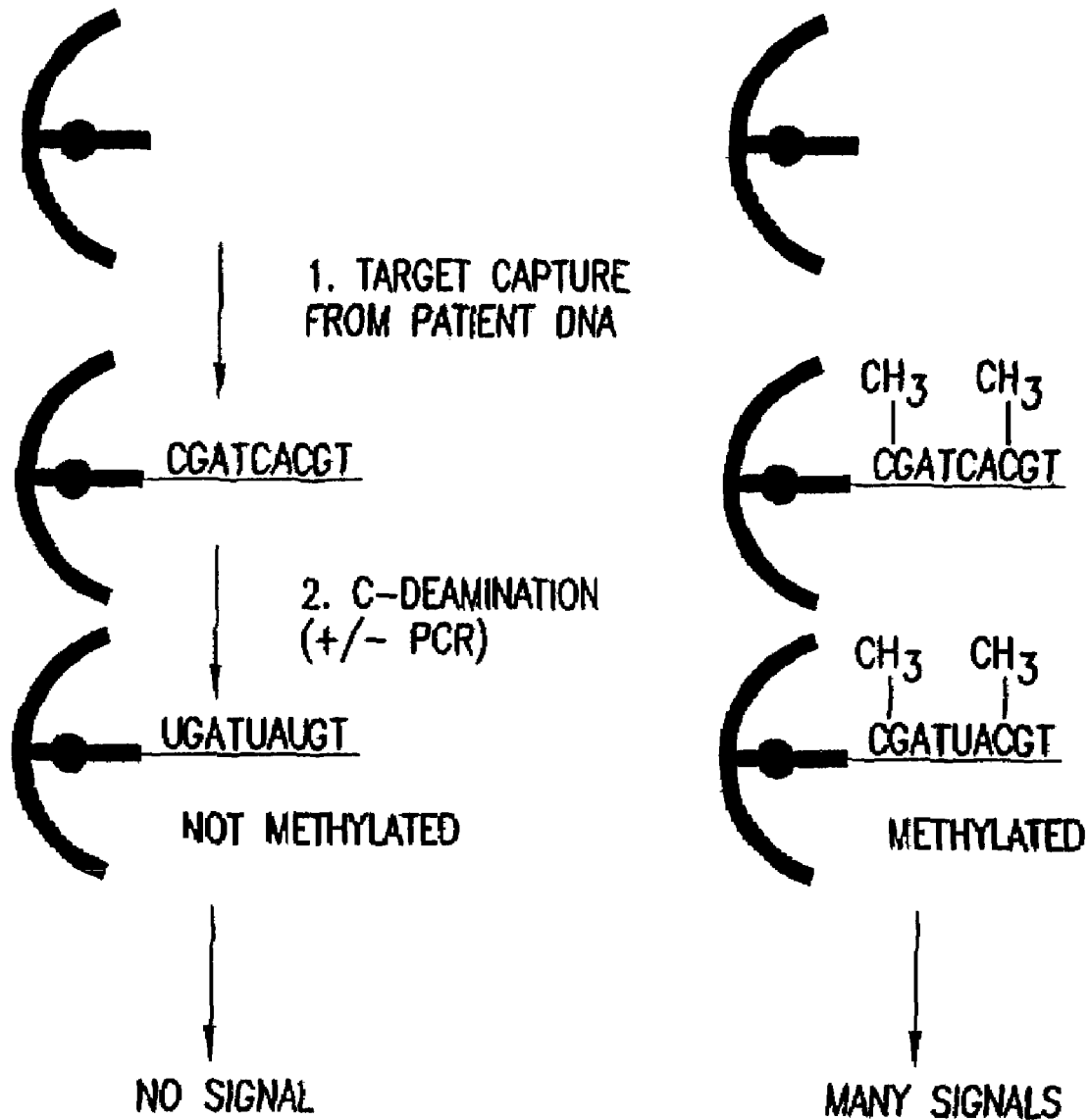

FIG. 28. Abortive Transcription Initiation with a labeled terminator. The scanned image of the thin layer chromatography plate shows the results of an abortive transcription initiation reaction using an unlabeled dinucleotide initiator, ApG, and a labeled terminator, which was 5'-SF-UTP (5-thioacetemidofluorescein-uridine 5'-triphosphate. The labeled terminator was efficiently incorporated to generate the oligonucleotide product ApGpU.

FIG. 29. Portion of the contig sequence of the CDKN2A gene. The sequence represents a small portion of the contig starting at 856630 nucleotides from the start of the contig sequence. The sequence represents a CpG island. Contig number: NT_008410.4. (SEQ ID NO: 15).

FIG: 30. Schematic representation of a "capture probe" to determine the methylation status of a specific gene. Oligonucleotide probes that are specific for a region near the CpG island of the target gene are immobilized onto a microtiter plate. The DNA of interest is added to the immobilized probe and bound to the capture probe. The DNA is then chemically modified to convert unmethylated C to T, and leave methyl-C unaffected. The converted DNA can then be amplified by an optional PCR step to further enhance the signal. A labeled CpG initiator is then added with an RNA polymerase and labeled nucleotide(s).

DETAILED DESCRIPTION OF THE INVENTION

The invention provides methods and kits for detecting the presence of a target molecule (such as nucleic acid sequence or protein) by generating multiple detectable oligonucleotides through reiterative synthesis events on a defined nucleic acid. The methods generally comprise using a labeled nucleotide or oligonucleotide transcription initiator to initiate synthesis of an abortive oligonucleotide product that is substantially complementary to a defined site on a target nucleic acid; using a chain terminator to terminate the polymerization reaction; and, optionally, using either (1) a target site probe to form a transcription bubble complex which comprises double-stranded segments on either side of a single-stranded target site or (2) an abortive promoter cassette comprising a transcription bubble region which includes a target site or (3) an abortive promoter cassette that is attached to any target molecule and then used to generate a signal.

In accordance with one aspect, the invention provides methods of synthesizing multiple abortive oligonucleotide transcripts from portions of a target DNA or RNA sequence, wherein the methods comprise combining and reacting the following: (a) a single-stranded target nucleic acid comprising at least one target site; (b) an RNA initiator that is complementary to a site on the target nucleic acid that is upstream of the target site; (c) an RNA polymerase; (d) optionally, nucleotides and/or nucleotide analogs; (e) a chain terminator; and (f) optionally, either (1) a target site probe that partially hybridizes to a target region on the target nucleic acid, forming a transcription bubble complex that includes first and second double-stranded regions on either side; of a single-stranded target site or (2) an abortive promoter cassette comprising a transcription bubble region that includes a transcription start site. The combination is subjected to suitable conditions, as described below, such that (a) a target site probe hybridizes with a target nucleic acid in a target region that includes the target site; (b) an RNA initiator hybridizes upstream of a target site; (c) an RNA polymerase utilizes the RNA initiator to initiate transcription at the target site, elongation occurs, and an oligonucleotide transcript is synthesized; (d) a chain terminator terminates transcription during elongation; (e) the RNA polymerase releases the short, abortive oligonucleotide transcript without substantially translocating from the polymerase binding site or dissociating from the template; and (f) steps (c) through (e) are repeated until sufficient signal is generated and the reaction is stopped. Alternatively, (a) an abortive promoter cassette hybridizes with an end of the target nucleic acid; (b) an RNA initiator hybridizes upstream of a transcription start site; (c) an RNA polymerase utilizes the RNA initiator to initiate transcription at the target site, elongation occurs, and an oligonucleotide transcript is synthesized; (d) a chain terminator terminates transcription during elongation; (e) the RNA polymerase releases the short, abortive oligonucleotide transcript without substantially translocating from the polymerase binding site or dissociating from the template; and (f) steps (c) through (e) are repeated until sufficient signal is generated and the reaction is stopped.

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, such as, "Molecular Biology Techniques Manual," third edition, (Coyne et al., 2001); "Short Protocols in Molecular Biology," fourth edition, (Ausubel et al., 1999) "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction" (Mullis et al., eds., 1994).

Primers, initiators, oligonucleotides, and polynucleotides employed as reactants in the present invention can be generated using standard techniques known in the art or may be obtained from commercial sources, including but not restricted to Sigma/Aldrich, Molecular Probes, Trilink Technologies.

Terms

To facilitate understanding of the invention, the following terms have the following meanings unless expressly stated otherwise:

"About" as used herein means that a number referred to as "about" comprises the recited number plus or minus 1-10% of that recited number. For example, "about" 50 nucleotides can mean 45-55 nucleotides or as few as 49-51 nucleotides depending on the situation.

"Transcription" is an enzyme-mediated process that synthesizes a complementary RNA transcript that corresponds to a nucleic acid template sequence. Transcription typically includes three phases, namely, initiation, elongation, and termination. The transcript of the template is processively synthesized by a polymerase through the formation of a phosphodiester bond between an initiator, which may be a mononucleoside, a mononucleotide, an oligonucleotide, or polynucleotide, and a subsequent NTP, et cetera., without the dissociation of either the nascent transcript or the polymerase from the template, until the polymerase reaches either a termination sequence on the template or the end of the template sequence or is stopped by other means, such as protein-DNA transcription roadblocks. As used in typical hybridization assays, the termination of transcription is generally achieved when the polymerase completes the elongation phase and reaches the end of the template sequence or a specific transcription termination signal after translocating from the initial enzyme binding site (promoter) on the template. In this context, "translocation" means that the polymerase moves along the template sequence from an initial enzyme binding site on the template to another point on the template which is at least 50 nucleotides downstream of the enzyme binding site.

"Abortive transcription" is an enzyme-mediated process that reiteratively initiates and terminates the synthesis of oligonucleotides that correspond to at least one portion, or target site, of a complementary nucleic acid template sequence. The abortive oligonucleotides synthesized vary in length of nucleotides, and may contain from about 2 to about 26 nucleotides, about 26 to about 50 nucleotides and about 50 nucleotides to about 100 nucleotides, and greater than 100 nucleotides.

"Abortive transcription" also includes three phases, namely, initiation, elongation, and termination. During the initiation phase, a polymerase forms a phosphodiester bond between an initiator and a second NTP, and then adds subsequent NTPs, et cetera., transcribing the template sequence to synthesize an oligonucleotide transcript of from about 2 to about 50 nucleotides in length and then terminating the transcription event by releasing the nascent oligonucleotide transcript, without the polymerase substantially translocating from the polymerase binding site or dissociating from the template. In other words, the RNA polymerase substantially remains at the initial binding site on the template, releases a first nascent oligonucleotide transcript, and then is capable of engaging in another transcription initiation event to produce a second oligonucleotide transcript, which is substantially complementary to substantially the same target site that was transcribed to produce the first oligonucleotide transcript. In this manner, the polymerase reiteratively-transcribes a single portion of the template (i.e., a target region) and releases multiple copies of substantially identical nascent oligonucleotide transcripts.

"Reverse transcription" refers to the transcription of an RNA template to synthesize complementary DNA (cDNA).

"Reiterative" refers to multiple identical or highly similar copies of a sequence of interest.

"Replication" is an enzyme-mediated process which synthesizes a complementary nucleic acid molecule from a single-stranded nucleic acid template sequence. The DNA replicate of the template is synthesized by a DNA polymerase through the formation of a phosphodiester bond between a primer and a first deoxyribonucleoside triphosphate (dNTP), followed by the formation of a second phosphodiester bond between the first dNTP and a subsequent dNTP, et cetera., without the dissociation of either the DNA replicate or the DNA polymerase from the template, until the DNA polymerase reaches either a termination sequence on the template or the end of the template sequence. In a typical DNA primer extension reaction, replication of the template terminates when the DNA polymerase synthesizes the entire template sequence after translocating from the initial enzyme binding site on the template. In this context, "translocation" means that the DNA polymerase moves along the template sequence from an initial enzyme binding site on the template to another point on the template which is downstream of the enzyme binding site.

"Oligonucleotide product" refers to the oligonucleotide that is synthesized by the reiterative synthesis reaction of the present invention. An oligonucleotide product may be an "oligonucleotide transcript," if the polymerization reaction is a transcription reaction catalyzed by an RNA polymerase, or an "oligonucleotide repeat," if the polymerization reaction is a DNA synthesis reaction catalyzed by telomerase or DNA polymerase.

"Termination" refers to the use of a chain terminator to conclude a chain elongation or primer extension reaction that is catalyzed by a polymerase. A "chain terminator" or "terminator" may comprise any compound, composition, complex, reactant, reaction condition, or process step (including withholding a compound, reactant, or reaction condition) which inhibits the continuation of transcription by the polymerase beyond the initiation and/or elongation phases. A "chain terminating nucleotide" is a chain terminator that comprises a nucleotide or nucleotide analog that inhibits further chain elongation once incorporated, due to either the structure of the nucleotide analog or the sequence of the nucleic acid being copied or transcribed.

A "target sequence" or "target polynucleotide" is a polynucleotide sequence of interest for which detection, characterization or quantification is desired. The actual nucleotide sequence of the target sequence may be known or not known.

A "target site" is that portion of the target sequence that is detected by transcription by a polymerase to form an oligonucleotide product. In accordance with the invention, there is at least one target site on a target nucleic acid. The sequence of a target site may or may not be known with particularity. That is, while the actual genetic sequence of the target nucleic acid may be known, the genetic sequence of a particular target site that is transcribed or replicated by a polymerase need not be known.

A "target region" is that portion of a target sequence to which a target site probe partially hybridizes to form a bubble complex, as described in detail below. In accordance with the invention, there is at least one target region on a target nucleic acid, and each target region comprises a target site. The sequence of a target region is known with sufficient particularity to permit sufficiently stringent hybridization of a complementary target site probe, such that the target site probe forms a bubble complex with the target region.

Generally, a "template" is a polynucleotide that contains the target nucleotide sequence. In some instances, the terms "target sequence" "template polynucleotide", "target nucleic acid", "target polynucleotide", "nucleic acid template", "template sequence", and variations thereof, are used interchangeably. Specifically, the term "template" refers to a strand of nucleic acid on which a complementary copy is synthesized from nucleotides or nucleotide analogs through the activity of a template-dependent nucleic acid polymerase. Within a duplex, the template strand is, by convention, depicted and described as the "bottom" strand. Similarly, the non-template strand is often depicted and described as the "top" strand. The "template" strand may also be referred to as the "sense" strand, and the non-template strand as the "antisense" strand.

"Synthesis" generally refers to the process of producing at least one complementary copy of a target site or other portion of a target sequence. "Multiple copies" means at least 2 copies. A "copy" does not necessarily mean perfect sequence complementarity or identity with the template sequence. For example, copies can include nucleotide analogs, intentional sequence alterations (such as sequence alterations introduced through a primer comprising a sequence that is hybridizable, but not complementary, to the template), and/or sequence errors that occur during synthesis. "Synthesis" encompasses both transcription of a target nucleic acid and replication of a target nucleic acid.

"Polynucleotide" or "nucleic acid strand", as used interchangeably herein, refers to nucleotide polymers of any length, such as two or more, and includes both DNA and RNA. The nucleotides can be deoxyribonucleotides, ribonucleotides, nucleotide analogs (including modified phosphate moieties, bases, or sugars), or any substrate that can be incorporated into a polymer by a suitable enzyme, such as a DNA polymerase or an RNA polymerase. Thus, a polynucleotide may comprise modified nucleotides, such as methylated nucleotides, and their analogs. If present, modification to the nucleotide structure may be imparted before or after synthesis of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., glutathione-s-transferase, methylases, demethylases, DNA repair enzymes, nucleases, toxins, antibodies, signal peptides, ply-L-lysine, etc.), those with intercalators (e.g., ethidium, acridine, psoralen, etc.), those with antibody-specific haptens (dinitrophenyl (DNP), biotin, etc.), those with affinity tags (hexahistadine, glutathione, etc.), those containing chelators (e.g., metals, radioactive metals, boron, oxidative metals, etc.), those containing alkylators, those with modified linkages (e.g., alpha anomeric nucleic acids, etc.), those with chemical or photochemical activities (DNA or RNA cleavage agents, crosslinkers, fluorescent compounds, etc.) as well as unmodified forms of the polynucleotide(s). Further, any of the hydroxyl groups ordinarily present on the pentose (i.e., ribose or deoxyribose) ring of a nucleotide may be, for example, replaced by phosphonate or phosphate groups, protected by standard protecting groups, activated to prepare additional linkages to additional nucleotides, or conjugated to a solid support. The 5' and 3' terminal OH groups on the pentose ring of a nucleotide can be phosphorylated or substituted with amines or organic capping group moieties of from about 1 to about 50 carbon atoms. Other hydroxyl groups on the ribose or deoxyribose ring may also be derivatized to standard protecting groups. Polynucleotides can also contain analogous forms of ribose or deoxyribose sugars that are generally known in the art, including, for example, 2'-O-methyl-2'-O-allyl, 2'-fluoro- or 2'-azido-ribose, carbocyclic sugar analogs, anomeric sugars, epimeric sugars, such as arabinose, xylose, pyranose sugars, furanose sugars, sedoheptuloses, acyclic analogs, and abasic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), "(O)NR$_2$ ("amidate"), P(O) R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl, or araldyl. Not all linkages in a polynucleotide need be identical. The preceding description applies to all polynucleotides referred to herein, including RNA and DNA.

"Nucleotide" or "NTP" refers to a base-sugar-phosphate compound. "Base" refers to a nitrogen-containing ring molecule that, when combined with a pentose sugar and a phosphate group, form a nucleotide. Bases include single ring pyrimidines, such as cytosine (C), thymine (T), and uracil (U), and double ring purines, such as adenine (A) and guanine (G). "Sugar" or "pentose sugar" generally refers to a pentose ring, such as a ribose ring or deoxyribose ring. Nucleotides are the monomeric subunits of both types of nucleic acid polymers, that is, RNA and DNA. "Nucleotide" or "NTP" refers to any nucleoside 5' phosphate, that is, ribonucleoside 5' phosphates (i.e., mono-, di-, and triphosphates) and deoxyribonucleoside 5' phosphates (ie., mono-, di-, and triphosphates), and includes "nucleoside phosphate analogs", "nucleotide analogs", and "NTP analogs". "Nucleoside phosphate analog", "nucleotide analog", and "NTP analog" refer to any nucleoside 5' phosphate (ie., mono-, di-, or triphosphate) which is analogous to a native nucleotide but which contains one or more chemical modifications when compared to the corresponding native nucleotide. Nucleotide analogs include base-modified analogs (e.g. 5-mercapto pyrimidines, 8-mercapto purines), phosphate-modified analogs (e.g., α-thio-triphosphates), and sugar-modified analogs (3' OMe, 3'deoxy) and may comprise modified forms of deoxyribonucleotides as well as ribonucleotides.

"Nucleoside" refers to a base-sugar combination without a phosphate group. Nucleosides include, but are note limited to, adenosine (A), cytidine (C), guanosine (G), thymidine (T), and uridine (U).

The term "oligonucleotide" generally refers to short, typically single-stranded, synthetic polynucleotides that are generally, but not necessarily, less than about 200 nucleotides in length. More particularly, an oligonucleotide may be defined as a molecule comprised of two or more nucleotides, including deoxyribonucleotides and/or ribonucleotides. The exact size depends on many factors, which in turn depend on the ultimate function or use of the oligonucleotide. The oligonucleotide may be generated in any manner, including chemical synthesis, DNA replication, degradation of longer DNA or RNA, transcription, reverse transcription, abortive transcription or reiterative synthesis, as further described herein, and a combination thereof.

Because mononucleotides undergo a reaction which synthesizes oligonucleotides by covalently bonding the 3' oxygen of a first mononucleotide pentose ring to the 5' phosphate of a second mononucleotide through a phosphodiester linkage, a first end of an oligonucleotide is referred to as the "5' end" if the 5' phosphate of the terminal nucleotide is not linked to a 3' oxygen of a nucleotide pentose ring, and a second end of an oligonucleotide is referred to as the "3' end" if the 3' oxygen of the terminal nucleotide is not linked to a 5' phosphate of a subsequent nucleotide pentose ring. As used herein, a nucleic acid sequence, even if the sequence is internal to a larger oligonucleotide, also may be said to have 5' and 3' ends. For single-stranded DNA or RNA, a first region along a nucleic acid strand is said to be "upstream" of a second region, if the 3' end of the first region is before the 5' end of the second region when moving along a strand of nucleic acid in a 5'→3' direction. Conversely, a first region along a nucleic acid strand is said to be "downstream" of a second region, if the 5' end of the first region is after the 3' end of the second region when moving along a strand of nucleic acid in a 5'→3' direction.

The term "3'" generally refers to a region or position in a polynucleotide or oligonucleotide that is 3' (downstream) from another region or position in the same polynucleotide or oligonucleotide when moving along the polynucleotide or oligonucleotide in a 5'→3' direction.

The term "5'" generally refers to a region or position in a polynucleotide or oligonucleotide that is 5' (upstream) from another region or position in the same polynucleotide or oligonucleotide when moving along the polynucleotide or oligonucleotide in a 5'→3' direction.

"Nucleic acid sequence" refers to an oligonucleotide or polynucleotide, and fragments, segments, or portions thereof, and to DNA or RNA of genomic or synthetic origin, which may be single- or double-stranded, and represents either the sense or the antisense strand.

The term "substantially single-stranded", when used in reference to a nucleic acid substrate, means that the substrate molecule exists primarily as a single strand of nucleic acid in contrast to a double-stranded substrate which exists as two substantially complementary segments or regions of nucleic acid that are held together by inter-strand or intra-strand base pairing interactions.

As used herein, the terms "complementary" or "complementarity" are used in reference to a first polynucleotide (which may be an oligonucleotide) which is in "antiparallel association" with a second polynucleotide (which also may be an oligonucleotide). As used herein, the term "antiparallel association" refers to the alignment of two polynucleotides such that individual nucleotides or bases of the two associated polynucleotides are paired substantially in accordance with Watson-Crick base-pairing rules. For example, the sequence "A-G-T" is complementary to the sequence "T-C-A." Complementarity may be "partial," in which only some of the polynucleotides' bases are matched according to the base pairing rules. Or, there may be "complete" or "total" complementarity between the polynucleotides. The degree of complementarity between the polynucleotides has significant effects on the efficiency and strength of the hybridization between two polynucleotides. This is of particular importance in synthesis reactions, as well as detection methods which depend upon binding between polynucleotides. Those skilled in the art of nucleic acid technology can determine duplex stability empirically by considering a number of variables, including, for example, the length of the first polynucleotide, which may be an oligonucleotide, the base composition and sequence of the first polynucleotide, and the ionic strength and incidence of mismatched base pairs. A general formula that may be used to calcuate the melting temperature of an oligonucleotide is: $Tm=(2(UA)+4(GC))-0.5$ C for every 1% formamide. For DNA-DNA hybrids, the Tm is approximated by the following formula: $Tm=81.5+16.6 (\log M)+0.41 (\% G+C)-500/L$; M is the molarity of the monovalent cations; L is the length of the hybrid base pairs (Anal Biochem. 138:267-284, 1984).

The terms "self-complementary" and "self-complementarity", when used in reference to a polynucleotide (e.g., an oligonucleotide), mean that separate regions of the polynucleotide can base-pair with each other. Because this term refers only to intramolecular base-pairing, any strand said to have a region of self-complementarity must have at least two regions capable of base-pairing with one another. As defined above, complementarity may be either "complete" or "partial". As used in reference to the oligonucleotides of the present invention, regions of an oligonucleotide are considered to have significant self-complementarity when these regions are capable of forming a duplex of at least 3 contiguous base pairs (i.e., three base pairs of complete complementarity), or when they may form a longer duplex that is partially complementary.

The term "primer" generally refers to a short, single-stranded oligonucleotide which has a free 3'-OH group and which can bind to and hybridize with a target sequence that is potentially present in a sample of interest. After hybridizing to a target sequence, a primer is capable of promoting or initiating polymerization or synthesis of a polynucleotide or oligonucleotide extension product that is complementary to the target sequence or a portion of the target sequence. A primer is selected to be "substantially" complementary to a specific portion of a target nucleic acid sequence. A primer is sufficiently complementary to hybridize with a target sequence and facilitate either transcription or replication of a portion of the target nucleic acid. A primer sequence need not reflect the exact sequence of the template. For example, a non-complementary nucleotide fragment may be attached to the 5' end of the primer, with the remainder of the primer sequence being substantially complementary to the template strand. Non-complementary bases can be interspersed within the primer, provided that the primer sequence has sufficient complementarity with the template sequence to hybridize with the template and thereby form a template-primer complex for initiating synthesis of a polynucleotide or oligonucleotide product.

The term "initiator" refers to a mononucleoside, mononucleotide, oligonucleotide, polynucleotide or analog thereof, which is incorporated into the 5' end of a nascent RNA molecule and may be considered a "primer" for RNA synthesis ("initiator primer").

In one embodiment, an RNA initiator facilitates the initiation of transcription at a target site on a single-stranded target nucleic acid in the absence of a template promoter sequence, as is known in the art. (See, U.S. Pat. No. 5,571,669; Daube and von Hippel, Science, 258: 1320-1324 (1992)). In another embodiment, initiators are used to randomly start abortive transcription at a plurality of target sites on the nucleic acid template (FIG. 16). The initiators and/or the individual nucleotides or nucleotide analogs that are used to extend the initiators may be suitably modified to enable signal generation, detection of the oligonucleotide products, and a determination of the presence or absence of the target sequence.

For example, it may be desirable to modify the initiator to provide the initiator with a label moiety for a variety of purposes, including detection of the abortive oligonucleotide product(s). Examples of such modifications include, but are not limited to, fluorescent molecules and energy transfer dyes (such as, fluorescein, aedans, coumarine, bodipy dyes, and rhodamine based dyes), fluorescent quencher molecules (for example, Dabcyl), proteins, peptides, amino linkers, or amino acid based molecules (for example polyhistidine), modified bases and modified and unmodified base analogs, peptide nucleic acids (PNAs), methylphosphonates, radioactive labels, terminal phosphates, 3' glyceryl, other carbohydrate based molecules, fatty acid derived molecules, carbon spacer molecules, electrochemiluminescent labels, lanthanide labels, avidin and its derivatives (for example, streptavidin, Neutravidin, etc.), biotin, steroid molecules (such as Digoxygenin), thiol linkages, ferritin labels, and the like.

As used herein, the term "hybridization" is used in reference to the base-pairing of complementary nucleic acids, including polynucleotides and oligonucleotides. Hybridization and the strength of hybridization (i.e., the strength of the association between the nucleic acids) is impacted by such factors as the degree of complementary between the nucleic acids, the stringency of the reaction conditions involved, the melting temperature ($T_m$) of the formed hybrid, and the G:C ratio within the duplex nucleic acid. Generally, "hybridization" methods involve annealing a complementary polynucleotide to a target nucleic acid (i.e., the sequence to be detected either by direct or indirect means). The ability of two polynucleotides and/or oligonucleotides containing complementary sequences to locate each other and anneal to one another through base pairing interactions is a well-recognized phenomenon.

With regard to complementarity, it may be important for some diagnostic applications to determine whether the hybridization of two polynucleotides and/or oligonucleotides represents complete or partial complementarity. For example, where it is desired to detect simply the presence or absence of pathogen DNA (such as from a virus, bacterium, fungi, mycoplasma, or protozoan for example), the hybridization method need only ensure that hybridization occurs when the relevant sequence is present; conditions can be selected where both partially complementary probes and completely complementary probes will hybridize. Other diagnostic applications, however, may require that the hybridization method be capable of distinguishing between partial and complete complementarity, such as in cases where it may be of interest to detect a genetic polymorphism, that is, a difference in a single base pair between multiple alleles (variations) that may exist for a particular gene or genetic marker.

"Stringency" generally refers to the conditions under which nucleic acid hybridizations are conducted, including temperature, ionic strength, and the presence of other compounds. Conditions of "high stringency" generally refer to those conditions under which nucleic acid base pairing will occur only between polynucleotide and/or oligonucleotide regions that have a high frequency of complementary base sequences. Consequently, conditions of "weak" or "low" stringency may be preferred when it is desirable to hybridize or anneal two polynucleotides and/or oligonucleotides, which are not completely complementary to one another.

The term "reactant" is used in its broadest sense. A reactant can comprise an enzymatic reactant, a chemical reactant, or ultraviolet light (ultraviolet light, particularly short wavelength ultraviolet light, is known to break polynucleotide polymers). Any agent capable of reacting with an oligonucleotide or polynucleotide to modify the oligonucleotide or polynucleotide is encompassed by the term "reactant," including a "reactant nucleotide" that is added to a reaction mixture for incorporation into an oligonucleotide product by a polymerase.

A "complex" is an assembly of components. A complex may or may not be stable and may be directly or indirectly detected. For example, as described herein, given certain components of a reaction and the type of product(s) of the reaction, the existence of a complex can be inferred. For the purposes of this invention, a complex is generally an intermediate with respect to a final reiterative synthesis product, such as a final abortive transcription or replication product for example.

A "reaction mixture" is an assemblage of components, which, under suitable conditions, react to form a complex (which may be an intermediate) and/or a product(s).

The term "enzyme binding site" refers to a polynucleotide region that is characterized by a sequence or structure that is capable of binding to a particular enzyme or class of enzymes, such as a polymerase.

"Polymerase" refers to any agent capable of facilitating or catalyzing the polymerization (joining) of nucleotides and/or nucleotide analogs. Suitable agents include naturally occurring enzymes, such as naturally occurring RNA polymerases (including RNA-dependent and DNA-dependent RNA polymerases), DNA polymerases (including DNA-dependent and RNA-dependent DNA polymerases), as well as modified or mutant enzymes that may currently exist (such as the mutant RNA polymerases disclosed in Sousa, et al., U.S. Pat. No. 6,107,037 for example) or may be hereafter created or designed, which modified or mutant enzymes may be designed to exhibit characteristics that are desirable for particular applications. Exemplary characteristics of a modified or mutant enzyme may include, but are not limited to, relaxed template specificity, relaxed substrate specificity, increased thermostability, and/or the like. It is intended that the term "polymerase" encompasses both thermostable and thermolabile enzymes.

The term "thermostable" when used in reference to an enzyme, such as an RNA or DNA polymerase for example, indicates that the enzyme is functional or active (i.e., can perform catalysis) at an elevated temperature, that is, at about 55° C. or higher. Thus, a thermostable polymerase can perform catalysis over a broad range of temperatures, including temperatures both above and below about 55° C.

The term "template-dependent polymerase" refers to a nucleic acid polymerase that synthesizes a polynucleotide or oligonucleotide product by copying or transcribing a template nucleic acid, as described above, and which does not synthesize a polynucleotide in the absence of a template. This is in contrast to the activity of a template-independent nucleic acid polymerase, such as terminal deoxynucleotidyl transferase or poly-A polymerase for example, that may synthesize or extend nucleic acids in the absence of a template.

A "DNA-dependent RNA polymerase" is an enzyme which facilitates or catalyzes the polymerization of RNA from a complementary DNA template.

A "DNA-dependent DNA polymerase" is an enzyme which facilitates or catalyzes DNA replication or synthesis, that is, the polymerization of DNA from a complementary DNA template.

An "RNA-dependent RNA polymerase" is an enzyme which facilitates or catalyzes the polymerization of RNA from a complementary RNA template.

An "RNA-dependent DNA polymerase" or "reverse transcriptase" is an enzyme that facilitates or catalyzes the polymerization of DNA from a complementary RNA template.

"Primer extension", "extension", "elongation", and "extension reaction" is the sequential addition of nucleotides to the 3' hydroxyl end of a mononucleotide, oligonucleotide, or polynucleotide initiator or primer which has been annealed or hybridized to a longer, template polynucleotide, wherein the addition is directed by the nucleic acid sequence of the template and/or the binding position of the polymerase. Extension generally is facilitated by an enzyme capable of synthesizing a polynucleotide or oligonucleotide product from a primer or initiator, nucleotides and a template. Suitable enzymes for these purposes include, but are not limited to, any of the polymerases described above.

"Incorporation" refers to becoming a part of a nucleic acid polymer. There is a known flexibility in the terminology regarding incorporation of nucleic acid precursors. For example, the nucleotide dGTP is a deoxyribonucleoside triphosphate. Upon incorporation into DNA, dGTP becomes dGMP, that is, a deoxyguanosine monophosphate moiety. Although DNA does not include dGTP molecules, one may say that one incorporates dGTP into DNA.

The terms "sample" and "test sample" are used in their broadest sense. For example, a "sample" or "test sample" is meant to include a specimen or culture (e.g., microbiological cultures) as well as both biological and environmental samples. Samples of nucleic acid used in the methods of the invention may be aqueous solutions of nucleic acid derived from a biological or environmental sample and separated, by methods known in the art, from other materials, such as proteins, lipids, and the like, that may be present in the sample and that may interfere with the methods of the invention or significantly increase the "background" signal in carrying out the methods.

A biological sample may comprise any substance which may include nucleic acid, such as animal (including human) tissue, animal fluids (such as blood, saliva, mucusal secretions, semen, urine, sera, cerebral or spinal fluid, pleural fluid, lymph, sputum, fluid from breast lavage, and the like), animal solids (e.g., stool), cultures of microorganisms, liquid and solid food and feedproducts, waste, cosmetics, or water that may be contaminated with a microorganism, or the like. An environmental sample may include environmental material, such as surface matter, soil, water, and industrial samples, as well as samples obtained from food and dairy processing instruments, apparatus, equipment, utensils, and disposable and non-disposable items. These examples are merely illustrative and are not intended to limit the sample types applicable to the present invention.

"Purified" or "substantially purified" refers to nucleic acids that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

The term "gene" refers to a DNA sequence that comprises control and coding sequences necessary for the production of a polypeptide or precursor. The polypeptide can be encoded by a full length coding sequence or by any portion of the coding sequence, so long as the desired functional activity is retained.

A "deletion" is defined as a change in a nucleic acid sequence in which one or more nucleotides are absent as compared to a standard nucleic acid sequence.

An "insertion" or "addition" is a change in a nucleic acid sequence which has resulted in the addition of one or more nucleotides as compared to a standard nucleic acid sequence.

A "substitution" results from the replacement of one or more nucleotides in a nucleic acid by different nucleotides.

An "alteration" in a nucleic acid sequence refers to any change in a nucleic acid sequence or structure, including, but not limited to a deletion, an addition, an addition-deletion, a substitution, an insertion, a reversion, a transversion, a point mutation, or a microsatellite alteration, or methylation.

"Methylation" refers to the addition of a methyl group ($—CH_3$) to a nucleotide base in DNA or RNA.

Sequence "mutation" refers to any sequence alteration in a sequence of interest in comparison to a reference sequence. A reference sequence can be a wild type sequence or a sequence to which one wishes to compare a sequence of interest. A sequence mutation includes single nucleotide changes, or alterations of more than one nucleotide in a sequence, due to mechanisms such as substitution, deletion, or insertion. A single nucleotide polymorphism (SNP) is also a sequence mutation as used herein.

"Microarray" and "array," as used interchangeably herein, refer to an arrangement of a collection of polynucleotide sequences in a centralized location. Arrays can be on a solid substrate, such as a glass slide, or on a semi-solid substrate, such as nitrocellulose membrane. The polynucleotide sequences can be DNA, RNA, or any combinations thereof.

The term "label" refers to any atom, molecule, or moiety which can be used to provide a detectable (preferably quantifiable) signal, either directly or indirectly, and which can be attached to a nucleotide, nucleotide analog, nucleoside mono-, di-, or triphosphate, nucleoside mono-, di-, or triphosphate analog, polynucleotide, or oligonucleotide. Labels may provide signals that are detectable by fluorescence, radioactivity, chemiluminescence, electrical, paramagnetism, colorimetry, gravimetry, X-ray diffraction or absorption, magnetism, enzymatic activity, and the like. A label may be a charged moiety (positive or negative charge) or, alternatively, may be charge neutral.

"Detection" includes any means of detecting, including direct and indirect detection. For example, "detectably fewer" products may be observed directly or indirectly, and the term indicates any reduction in the number of products (including no products). Similarly, "detectably more" products means any increase, whether observed directly or indirectly.

As used herein, the terms "comprises," "comprising", "includes", and "including", or any other variations thereof, are intended to cover a non-exclusive inclusion, such that a process, method, composition, reaction mixture, kit, or apparatus that comprises a list of elements does not include only those elements but may include other elements not expressly listed or inherent to such process, method, composition, reaction mixture, kit, or apparatus.

"A," "an," "the," and the like, unless otherwise indicated, include plural forms.

Components and Reaction Conditions

Target Nucleic Acid

The target nucleic acid can be either a naturally occurring or synthetic polynucleotide segment, and it can be obtained or synthesized by techniques that are well-known in the art. A target sequence to be detected in a test sample may be present initially as a discrete molecule, so that the sequence to be detected constitutes the entire nucleic acid, or may be present as only one component of a larger molecule. The target nucleic acid can be only a minor fraction of a complex mixture, such as a biological sample, and can be obtained from various biological materials by procedures that are well-known in the art. The target nucleic acid to be detected may include nucleic acids from any source, in purified, or unpurified form, which can be DNA (including double-stranded (ds) DNA and single-stranded (ss) DNA) or RNA. (including tRNA, mRNA, rRNA), mitochondrial DNA or RNA, chloroplast DNA or RNA, DNA-RNA hybrids, or mixtures thereof; genes, chromosomes, or plasmids; and the genomes of biological material, such as the genomes of microorganisms (including bacteria, yeast, viruses, viroids, molds, and fungi), plants, animals, humans, or fragments thereof. Standard techniques in the art are used to obtain and purify the nucleic acids from a test sample. Methods for the extraction and/or purification of such nucleic acids have been described, for example, by Sambrook, et al., Molecular Cloning: A Laboratory Manual (New York, Cold Spring Harbor Laboratory, third edition, 2000). Detection of an RNA target may or may not require initial complementary DNA (cDNA) synthesis, as known in the art. Detection of a DNA-RNA hybrid may require denaturation of the hybrid to obtain a ssDNA or denaturation followed by reverse transcription to obtain a cDNA.

Target Proteins

In another embodiment of the invention, the target may be another molecule, such as a protein, which is labeled by covalent or noncovalent attachment of a defined nucleic acid sequence which can be used for reiterative oligonucleotide synthesis (FIG. 23). The target protein can be either a naturally occurring or synthetic polypeptide segment, and it can be obtained or synthesized by techniques that are well-known in the art. A target protein to be detected in a test sample may be present initially as a discrete molecule, so that the protein to be detected constitutes the entire protein, or may be present as only one component of a larger complex. The target protein can be only a minor fraction of a complex mixture, such as a biological sample, and can be obtained from various biological materials by procedures that are well-known in the art. The target protein to be detected may include proteins from any source, in purified or unpurified form. Standard techniques in the art are used to obtain and purify the proteins from a test sample. Methods for the extraction and/or purification of such proteins have been described, for example, by Sambrook, et al., Molecular Cloning: A Laboratory Manual (New York, Cold Spring Harbor Laboratory, third edition, 2000).

Immobilization

In one embodiment of the invention, the target molecule may be immobilized. In another embodiment, the target molecule may be immobilized to form, for example, a microarray. A single molecule array in accordance with this embodiment includes a solid matrix, a bioreactive or bioadhesive layer, and a bioresistant layer. Solid phases that are useful as a matrix for the present invention include, but are not limited to, polystyrene, polyethylene, polypropylene, polycarbonate, or any solid plastic material in the shape of test tubes, beads microparticles, dip-sticks, or the like. Additionally, matrices include, but are not limited to, membranes, microtiter plates (e.g., 96-well and 384-well), test tubes, and Eppendorf tubes. Solid phases also include glass beads, glass test tubes, and any other appropriate shape that is made of glass. A functionalized solid phase, such as plastic or glass, which has been modified so that the surface carries carboxyl, amino, hydrazide, or aldehyde groups can also be used. In general, suitable solid matrices comprise any surface to which a bioadhesive layer, such as a ligand-binding agent, can be attached or any surface which itself provides a ligand attachment site.

The bioadhesive layer can be an ionic adsorbent material such as gold, nickel, or copper (Montemagno and Bachand, Constructing Nanomechanical Devices Powered by Biomolecular Motors, Nanotechnology, 10: 225-231 (1999)), protein-adsorbing plastics, such as polystyrene (U.S. Pat. No. 5,858,801), or a covalent reactant, such as a thiol group. To create a patterned array in the bioadhesive layer, an electron-sensitive polymer, such as polymethyl methacrylate (PMMA) for example, can be used to coat the solid support and can be etched in any desired pattern with an electron beam followed by development to remove the sensitized polymer. The etched portions of the polymer are then coated with a metal, such as nickel, and the polymer is removed with a solvent, leaving a pattern of metal posts on the substrate. This method of electron beam lithography provides the high spatial resolution and small feature size which facilitates the immobilization of a single molecule at each point in the patterned array. An alternate means for creating high-resolution patterned arrays is atomic force microscopy. A further means is X-ray lithography.

Antibody or oligonucleotide capture probes can be attached to the bioadhesive pattern by providing a polyhistidine tag on the capture probe that binds to the metal bioadhesive patterns. The capture probes may be, for example, from about 15 to about 500 nucleotides in length. Other conventional means for attachment employ homobifunctional and heterobifunctional crosslinking reagents. Homobifunctional reagents carry two identical functional groups, whereas heterobifunctional reagents contain two dissimilar functional groups to link the capture probes to the bioadhesive. The heterobifunctional cross-linking agents may contain a primary amine-reactive group and a thiol-reactive group. Covalent crosslinking agents are selected from reagents capable of forming disulfide (S—S), glycol (—CH(OH)—CH(OH)—), azo (—N=N—), sulfone (—S($=O_2$—), ester (—C(=O)—O—), or amide (—C(=O)—N—) bridges. Crosslinking agents include, but are not limited to, maleamides, iodoacetamides, and disulfies. Table 1 provides a list of representative classes of crosslinking reagents and their group specificity (Wong, S. S. Chemistry of Protein Conjugation and Cross-Linking, 1991, CRC Press, Inc., Boca Raton, USA).

TABLE 1

Crosslinking Reagents and group specificity

| Reagent | Group specificity |
|---|---|
| alpha-haloacetyl compounds eg ICH2COOH | SH, S—CH$_3$, NH$_2$, phenolic, imadazole |
| N-maleimides | SH, NH$_2$ |
| mercurials | SH |
| Disulfides | SH |
| Aryl halides | SH, NH$_2$, phenolic, imidazole |
| Acid anhydndes eg. Succinic anhydride | NH$_2$, phenolic |
| Isocyanates eg. HNCO | NH$_2$ |
| Isothiocyanates R-NCS | NH$_2$ |
| Sulfonyl halides | NH$_2$ |
| Imidoesters | NH$_2$ |
| Diazoacetates | COOH, SH |
| Diazonium salts eg benzene-N2 + Cl— | phenolic, imidazole |
| dicarbonyl compound | NH—C(NH)—NH$_2$ |

A bioresistant layer may be placed or superimposed upon the bioadhesive layer either before or after attachment of the capture probe to the bioadhesive layer. The bioresistant layer is any material that does not bind the capture probe. Non-limiting examples include bovine serum albumin, gelatin, lysozyme, octoxynol, polysorbate 20 (polyethenesorbitan monolaurate), and polyethylene oxide containing block copolymers and surfactants (U.S. Pat. No. 5,858,801). Deposition of the bioadhesive and bioresistant layers may be accomplished by conventional means, including spraying, immersion, and evaporative deposition (metals).

In one embodiment, the solid matrix may be housed in a flow chamber having an inlet and outlet to accommodate the multiple solutions and reactants that are allowed to flow past the immobilized capture probes. The flow chamber can be made of plastic or glass and may be either open or transparent in the plane viewed by a microscope or optical reader. Electro-osmotic flow includes a fixed charge on the solid support and a voltage gradient (current) passing between two electrodes placed at opposing ends of the solid support.

Primers

In accordance with the invention, a primer is used to initiate replication by a DNA polymerase of a target site on the target nucleic acid. If the polymerase is a DNA polymerase, the primer may be comprised of ribonucleotides or deoxyribonucleotides. The primers and/or the individual nucleotides or nucleotide analogs that are used to extend the primers may be suitably modified to enable signal generation, detection of the oligonucleotide products, and a determination of the presence or absence of the target sequence.

The primers used in the practice of the invention may be made synthetically, using conventional chemical or enzymatic nucleic acid synthesis technology. In one embodiment, the primers are less than about 25 nucleotides in length, usually from about 1 to about 10 nucleotides in length, and preferably about 2 to 3 nucleotides in length. It may be desirable to modify the nucleotides or phosphodiester linkages in one or more positions of the primer. Examples of such modifications include, but are not limited to, fluorescent molecules and energy transfer dyes (such as, fluorescein, aedans, coumarine, bodipy dyes, and rhodamine based dyes), fluorescent quencher molecules (for example, Dabcyl), proteins, peptides, amino linkers, or amino acid based molecules (for example polyhistidine), modified bases and modified and unmodified base analogs, peptide nucleic acids (PNAs), methylphosphonates, radioactive labels, terminal phosphates, 3' glyceryl, other carbohydrate based molecules, fatty acid derived molecules, carbon spacer molecules, electro-chemiluminescent labels, lanthanide labels, avidin and its derivatives (for example, streptavidin, Neutravidin, etc.), biotin, steroid molecules (such as Digoxygenin), thiol linkages, ferritin labels, and the like.

Target Site Probes

In accordance with the invention, an oligonucleotide target site probe is used to direct a polymerase to a target site on the target nucleic acid by forming a bubble complex in a target region of the target nucleic acid (FIG. 11). The target site probe may vary in the length of nucleotides, including but not limited to, about 20 to about 50 nucleotides, about 51 to about 75 nucleotides, about 76 to about 100 nucleotides, and greater than 100 nucleotides. The bubble complex comprises double-stranded regions on either side of a single-stranded region which includes a target site. In one embodiment, the target site probe includes three regions: a first region on the 5' end of the target site probe is complementary to and hybridizes with the template sequence upstream of a target site on the template sequence; a second region, which is 3' of the first region, is non-complementary to the template sequence and therefore does not hybridize with the template sequence; and a third region, which is on the 3' end of the target site probe, is complementary to and hybridizes with the template sequence downstream of the target site. The target site probe can vary in nucleotide length, including but not limited to, about 5-19; about 20 to about 50 nucleotides, about 51 to about 75 nucleotides, about 76 to about 100 nucleotides and greater than 100 nucleotides.

Use of the target site probe directs the polymerase to a particular enzyme binding site (i.e., the double-stranded segment and bubble formed upstream of the target site by the template sequence and the primer) on the template sequence to facilitate the initiation of transcription at a particular target site. That is, rather than facilitating the random initiation of synthesis reactions by the polymerase along the length of a single-stranded template sequence, as described above, this embodiment provides targeted binding of the polymerase for the detection of a particular target site encompassed by the bubble complex formed by the target site probe.

The target site probes used in the practice of the invention may be made enzymatically or synthetically, using conventional nucleic acid synthesis technology, such as phosphoramidite, H-phosphonate, or phosphotriester chemistry, for example. Alternative chemistries, such as those which result in non-natural backbone groups, such as phosphorothioate, phosphoramidate, and the like, may also be employed. The target site probes may be ordered commercially from a variety of companies which specialize in custom polynucleotides and/or oligonucleotides, such Operon, Inc. (Alameda, Calif.).

The sequence of the target site probe will vary depending upon the target sequence. The overall length of the target site probe is selected to provide for hybridization of the first and third regions with the target sequence and optimization of the length of the second, non-hybridized region. The first and third regions of the target site probe are designed to hybridize to known internal sites on the target nucleic acid template. Depending upon the application, the sequence of the second region on the target site probe can be designed such that the second region may or may not be self-complementary. The overall length of the target site probe ranges from about 20 to about 50 nucleotides, preferably from about 25 to about 35 nucleotides. The first and third regions of the target site probe each range from about 5 to about 20 nucleotides in length, preferably from about 8 to about 10 nucleotides in length. In one embodiment, the first and third regions of the target site probe are each about 10 nucleotides in length. The internal, second region on the target site probe ranges in length from about 8 to about 14 nucleotides, preferably from about 12 to about 14 nucleotides.

In one embodiment, at least one target site probe is used to specifically initiate abortive oligonucleotide synthesis at one or more target sites on the nucleic acid template to produce multiple oligonucleotide products. In another embodiment, the target site probe directs the initiation of abortive transcription on a single-stranded target site in the absence of a template promoter sequence, as is known in the art. (See, U.S. Pat. No. 5,571,669; Daube and von Hippel, Science, 258: 1320-1324 (1992)).

Abortive Promoter Cassette

In accordance with the invention, an abortive promoter cassette (APC) may be used to link a target to a defined sequence to generate multiple detectable oligonucleotide products that indicate the presence of the target in a test sample. The APC is a self-complementary sequence of DNA that may consist of: (1) one contiguous oligonucleotide to which RNA polymerase can bind to form a transcription bubble; (2) two partially complementary upper and lower oligonucleotides that form a single-stranded transcription bubble region comprising a defined site from which an initiator and a suitable RNA polymerase can synthesize an abortive oligonucleotide product; or (3) two complementary oligonucleotides that form a transcription bubble region in the presence of an RNA polymerase, which allows for the synthesis of an abortive oligonucleotide product. The APC may contain an artificial promoter, or it may contain the promoter for a specific RNA polymerase. For example, trinucleotide or tetranucleotide products that could be generated from with a common phage RNA polymerase can be made with a labeled GpA or GpApA initiator and a labeled pppG or pppA terminator.

Figure 1:
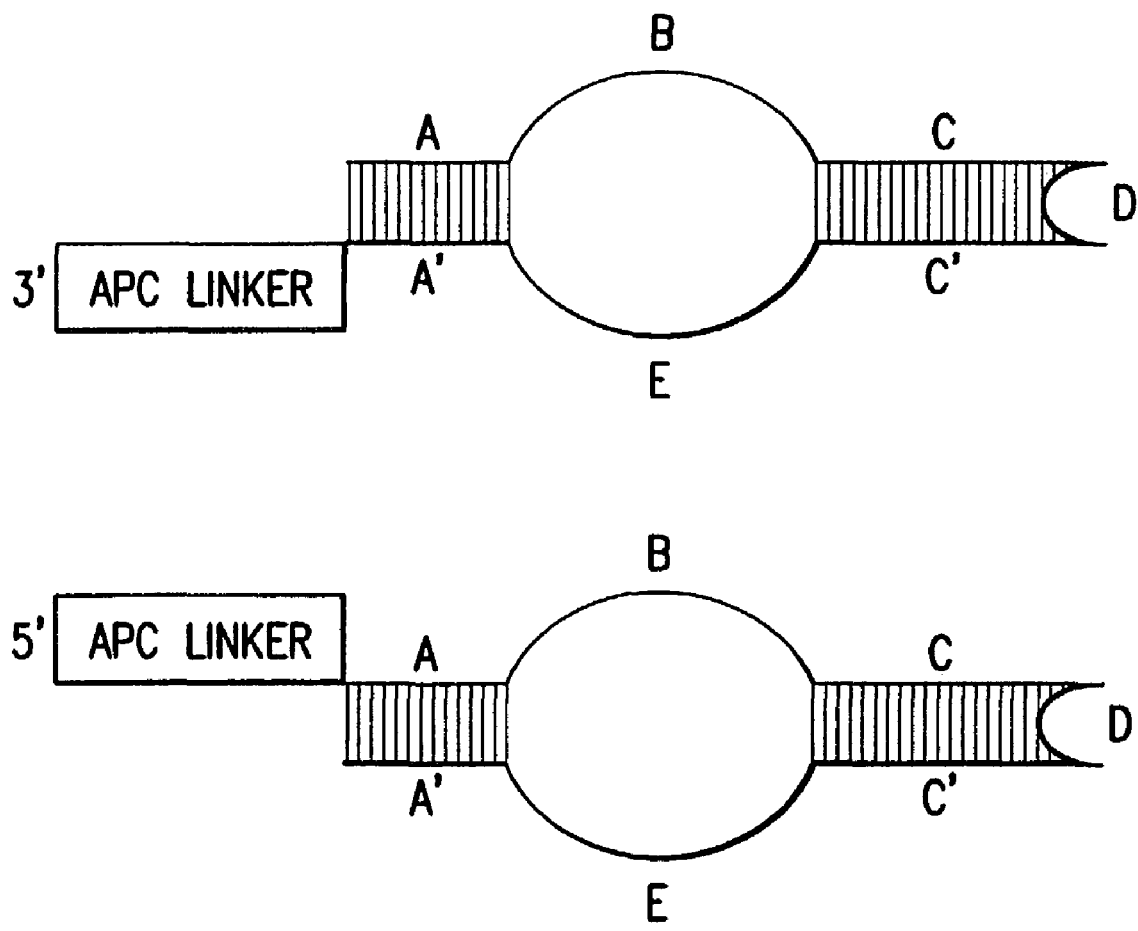

In an exemplary embodiment, as illustrated in FIG. 1, the APC comprises eight regions, including an APC linker sequence which comprises either a 3' or a 5' single-stranded overhang region (i.e., a "sticky end"). A first region (A) on the 5' end of the APC is complementary to a second region (A') near the 3' end of the APC. A third region (B) and a fourth region (E) are separated from each other by regions C, D, and C' and are non-complementary to each other, such that the regions B and E form a single-stranded bubble region on the APC when the self-complementary regions of the APC interact with one another. Regions C and C' are substantially self-complementary, such that the 5' end of region C is complementary to the 3'end of the region C'. Region D may be a short sequence joining C and C' for a contiguous APC or may be a region comprising the free 3' or 5' ends of two separate upper and lower oligonucleotides for a two-part APC. Finally, the APC also includes an APC linker, a single-stranded region on either the 5' end or the 3' end of the APC oligonucleotide, which is formed through the complementary interaction of regions A and A'. The APC linker facilitates attachment of the APC with other target molecules, such as captured target DNA, RNA, or protein, for example.

The APC used in the practice of the invention may be made enzymatically or synthetically, using conventional nucleic acid synthesis; technology, such as phosphoramidite, H-phosphonate, or phosphotriester chemistry, for example. Alternative chemistries, such as those that result in: non-natural backbone groups, such as phosphorothioate, phosphoramidate, and the like, may also be employed. The APC may be ordered commercially from a variety of companies that specialize in custom polynucleotides and/or oligonucleotides, such as Operon, Inc. (Alameda, Calif.).

The length of the APC is selected to optimize the stability of the bubble region and provide for the hybridization of the APC linker sequence with the target sequence. The overall length of the APC may range from about 50 to about 150 nucleotides, preferably from about 55 to about 125 nucleotides. Regions A and A' may each comprise from about 5 to about 25 nucleotides and preferably comprise from about 7 to about 15 nucleotides. Regions B and E may comprise from about 8 to about 16 nucleotides and preferably comprise from about 10 to about 14 nucleotides. Regions C and C' may each comprise from about 5 to about 25 nucleotides and preferably comprise from about 10 to about 20 nucleotides. The single-stranded overhang region may comprise from about 5 to about 40 nucleotides and preferably comprises from about 10 to about 25 nucleotides.

Polymerase

Template-dependent polymerases for use in the methods and compositions of the present invention are known in the art. Either eukaryotic or prokaryotic polymerases may be used. In one embodiment, the template-dependent polymerase is a thermostable polymerase. In another embodiment, the polymerase is able to tolerate label moieties on the phosphate group, the nuclease, and/or on the pentose ring of unincorporated nucleotides. In one embodiment, the polymerase is a DNA-dependent RNA polymerase which is capable of transcribing a single-stranded DNA template without a promoter sequence. In another embodiment, the polymerase is a DNA-dependent RNA polymerase which is capable of transcribing a single-stranded DNA template having a promoter sequence that is capable of binding the particular RNA polymerase being used. In another embodiment, the polymerase is a DNA-dependent DNA polymerase that is capable of replicating a DNA target site to form a DNA oligonucleotide product. In a further embodiment, the polymerase is an RNA-dependent DNA polymerase that is capable of synthesizing a single-stranded complementary DNA transcript from an RNA template. Examples of suitable polymerases include the RNA polymerases encoded by *Escherichia coli*, *Escherichia coli* bacteriophage T7, *Escherichia coli* bacteriophage T3, and *Salmonella typhimurium* bacteriophage SP6; RNA-dependent RNA polymerases, such as poliovirus RNA polymerase; reverse transcriptases, such as HIV reverse transcriptase; and DNA polymerases such as *Escherichia coli*, T7, T4 DNA polymerase, Taq thermostable DNA polymerase, terminal transferase, primase, and telomerase.

In general, the enzymes included in the methods of the present invention preferably do not produce substantial degradation of the nucleic acid components produced by the methods.

Nucleotides

In accordance with the invention, the polymerase catalyzes a reaction in the usual 5'→3' direction on the oligonucleotide product and either transcribes or replicates the target nucleic acid by extending the 3' end of the initiator or primer through the sequential addition of nucleotides (NTPs), which may include nucleotide analogs (NTP analogs) and which may be labeled or unlabeled. To facilitate reiterative, abortive synthesis initiation events, the NTPs and/or NTP analogs that are added to the reaction mixture before and/or during the synthesis reaction include a chain terminator, which is capable of terminating the synthesis event initiated by the polymerase. Use of the chain terminator stalls the polymerase during the synthesis reaction, inhibits formation of a processive elongation complex, and thereby promotes the reiterative synthesis of short abortive oligonucleotides from the target site. (Daube and von Hippel, Science, 258: 1320-1324 (1992)).

In accordance with the invention, a chain terminator may comprise any compound, composition, complex, reactant, reaction condition, or process step (including withholding a compound, reactant, or reaction condition) which is capable of inhibiting the continuation of transcription or replication by the polymerase during the primer extension reaction. In one embodiment, a suitable chain terminator is NTP deprivation, that is, depriving the polymerase of the particular NTP that corresponds to the subsequent complementary nucleotide of the template sequence. In other words, since NTP requirements for chain elongation are governed by the complementary strand sequence, given a defined template sequence and a defined primer length, a selected NTP may be withheld from the reaction mixture such that termination of chain elongation by the polymerase results when the reaction mixture fails to provide the polymerase with the NTP that is required to continue transcription or replication of the template sequence.

Alternatively, in another embodiment, the chain terminator may include nucleotide analogs, which may be labeled or unlabeled and which, upon incorporation into an oligonucleotide product by the polymerase, effect the termination of nucleotide polymerization. Specifically, since chain elongation by a polymerase requires a 3' OH for the addition of a subsequent nucleotide, nucleotide analogs having a suitably modified 3' end will terminate chain elongation upon incorporation into the oligonucleotide product. Nucleotide analogs having chain terminating modifications to the 3' carbon of the pentose sugar are known in the art and include nucleotide analogs such as 3' dideoxyribonucleoside triphosphates (ddNTPs) and 3' O-methylribonucleoside 5' triphosphates, as well as nucleotide analogs having either a —H or a —$OCH_2$ moiety on the 3' carbon of the pentose ring. Alternatively, in a further embodiment, the chain terminator may include nucleotide analogs, either labeled or unlabeled, which have a 3' OH group, but which, upon incorporation into the oligonucleotide product, still effect chain termination at some positions, as described herein (Costas, Hanna, et al., Nucleic Acids Research 28: 1849-58 (2000); Hanna, M., Meth Enzymology 180: 383-409 (1989); Hanna, M., Nucleic Acids Research 21: 2073-79 (1993); Hanna, M. et al., Nucleic Acid Research 27: 1369-76 (1999)).

NTPs and/or NTP analogs that can be employed to synthesize abortive oligonucleotide products in accordance with the methods of the invention may be provided in amounts ranging from about 1 to about 5000 μM, preferably from about 10 to about 2000 μM. In a preferred aspect, nucleotides and/or nucleotide analogs, such as ribonucleoside triphosphates or analogs thereof, that can be employed to synthesize oligonucleotide RNA transcripts by the methods of the invention may be provided in amounts ranging from about 1 to about 6000 μM, preferably from about 10 to about 5000 μM.

Labeling and Detection

In accordance with an aspect of the invention, detectable oligonucleotide products are synthesized from a target nucleic acid template. The detection and identification of the oligonucleotide products are facilitated by label moieties on the initiator and/or on the NTPs or NTP analogs that are incorporated by the polymerase into each oligonucleotide product that is synthesized on the target nucleic acid and/or on other molecules which are part of the synthetic complex or which interact with one or more components of the synthetic complex. The label or reporter moieties may be chemically or enzymatically incorporated into the nucleotides forming the primer and/or into the reactant NTPs or NTP analogs that are utilized by the polymerase during the extension reaction, or other molecules, and may include, for example, fluorescent tags; paramagnetic groups; chemiluminescent groups; metal binding sites; intercalators; photochemical crosslinkers; antibody-specific haptens; metals; small molecules which are members of a specific binding pair (such as biotin and streptavidin for example); and any other reporter moiety or moieties which can produce a detectable and/or quantifiable signal either directly or indirectly. Exemplary nucleotide analogs may include, for example, 8-modified purines (8-APAS-ATP) (Costas, Hanna, et al., Nucleic, Acids Research 28: 1849-58 (2000)); 5-modified pyrimidines (5-APAS-UTP; 5-APAS-CTP) (Hanna, M., Meth Enzymology 180: 383-409 (1989); Hanna, M., Nucleic Acids Research 21: 2073-79 (1993)); fluorescent ribonucleotides (5-SF-UTP) (Hanna, M. et al., Nucleic Acid Research 27: 1369-76 (1999)); and hapten-tagged deoxynucleotide precursors (5-DNP-SdU) (Meyer and Hanna, Bioconjugate Chem 7: 401-412 (1996); U.S. Pat. Nos. 6,008,334 and 6,107,039).

In one embodiment, a fluorophore moiety is attached to the 5' end of the initiator that is used to initiate transcription of the target nucleic acid. In another embodiment, a fluorophore moiety is attached to the 5 or 8 position of the base of an NTP or NTP analog that is used by the polymerase to extend the initiator primer. In a further embodiment, a first fluorophore moiety is attached to the initiator and a second fluorophore is attached to an NTP or NTP analog that is used to extend the initiator. In this latter embodiment, a fluorescent energy transfer mechanism can be used, wherein the first fluorophore (e.g. fluorescein, aedans, coumarin, etc.) is excited and the emission is read from the second fluorophore (e.g. fluorescein, aedans, coumarin, etc.) when the second fluorophore is brought into proximity with the first fluorophore by the polymerase during synthesis of the oligonucleotide product. Alternatively, the first and second fluorophores may function by an electron transfer mechanism, wherein the first fluorophore absorbs energy from the second fluorophore when the polymerase brings the first and second fluorophores into proximity with each other, and the first fluorophore releases the energy in a radiative manner, thereby enabling detection.

In one aspect, a first fluorophore is a fluorescent energy donor, which is attached to a first reactant (i.e., either a nucleotide that is incorporated into the initiator or a nucleotide that is to be incorporated by the polymerase into the oligonucleotide product), and a second fluorophore is a fluorescent energy acceptor, which is attached to a second reactant (either a nucleotide that is incorporated into the initiator nucleotide or a nucleotide that is to be incorporated by the polymerase into the oligonucleotide product) that is different from the first reactant. In one embodiment, each of the four NTPs or NTP analogs that may be used to extend the primer is tagged with a unique fluorescent energy acceptor which is capable of a distinct emission wavelength when brought into proximity with the fluorescent energy donor on the primer. Preferably, the fluorescent energy transfer can be measured in real time, without isolation of the oligonucleotide products, since neither the initiator nor unincorporated NTPs or NTP analogs alone will produce a signal at the wavelength used for detection.

Fluorescent and chromogenic molecules and their relevant optical properties are amply described in the literature. See, for example, Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, ed., Indicators (Pergamon Press, Oxford, 1972); Haugland, Handbook of Fluorescent Probes and Research Chemicals (Molecular Probes, Eugene, 1992); Pringsheim, Fluorescence and Phosphorescence (Interscience Publishers, New York, 1949); and the like. Further, there is extensive guidance in the literature for derivatizing fluorophore and quencher molecules for covalent attachment via common reactive groups that can be added to a nucleotide, as exemplified by the following references: Haugland (supra); Ullman et al., U.S. Pat. No. 3,996,345; Khanna et al., U.S. Pat. No. 4,351,760; Costas, Hanna, et al., Nucleic Acids Research 28: 1849-58 (2000); Hanna, M. et al., Nucleic Acid Research 27: 1369-76 (1999); and Meyer and Hanna, Bioconjugate Chem 7: 401-412 (1996).

In general, nucleotide labeling can be accomplished through any of a large number of known nucleotide labeling techniques using known linkages, linking groups, and associated complementary functionalities. Suitable donor and acceptor moieties that can effect fluorescence resonance energy transfer (FRET) include, but are not limited to, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-amino-1-naphthyl)maleimide; anthranilamide; BODIPY; Brilliant Yellow; coumarin, and derivatives: coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5',5''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate; erythrosin and derivatives: erythrosin B, erythrosin, isothiocyanate; ethidium; fluorescein and derivatives: 5-carboxyfluorescein (FAM),5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl lpyrene; butyrate quantum dots; Reactive Red 4 (Cibacron™ Brilliant Red 3B-A); rhodamine and derivatives: 6-carboxy-X-rhodamine (ROX), 6-carboxyrhodamine (R6G), lissamine rhodamine B, sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid; terbiun chelate derivatives; Cy 3; Cy 5; Cy 5.5; Cy 7; IRD 700; IRD 800; La Jolla Blue; phthalo cyanine; and naphthalo cyanine.

There are many linking moieties and methodologies for attaching fluorophores to nucleotides, as exemplified by the following references: Eckstein, ed., Oligonucleotides and Analogues: A Practical Approach (IRL Press, Oxford, 1991); Zuckerman et al., Nucleic Acids Research 15: 5305-5321 (1987) (3' thiol group on oligonucleotide); Sharma et al., Nucleic Acids Research 19: 3019 (1991) (3' sulfhydryl); Giusti et al., PCR Methods and Applications 2: 223-227 (1993); Fung et al., U.S. Pat. No. 4,757,141 (5' phosphoamino group via Aminolink™ II, available from Applied Biosystems, Foster City, Calif.); Stabinsky, U.S. Pat. No. 4,739,044 (3' aminoalkylphosphoryl group); Agrawal et al., Tetrahedron Letters 31: 1543-1546 (1990) (attachment via phosphoramidate linkages); Sproat et al., Nucleic Acids Research 15: 4837 (1987) (5-mercapto group); Nelson et al., Nucleic Acids Research 17: 7187-7194 (1989) (3' amino group); Hanna, M., Meth Enzymology 180: 383-409 (1989); Hanna, M., Nucleic Acids Research 21: 2073-79 (1993); Hanna, M. et al., Nucleic Acid Research 27: 1369-76 (1999) (5-mercapto group); Costas, Hanna, et al., Nucleic Acids Research 28: 1849-58 (2000) (8-mercapto group); and the like.

In accordance with the invention, detection of the oligonucleotide products is indicative of the presence of the target sequence. Quantitative analysis is also feasible. Direct and indirect detection methods (including quantitation) are well known in the art. For example, by comparing the amount of oligonucleotide products that are generated from a test sample containing an unknown amount of a target nucleic acid to an amount of oligonucleotide products that were generated from a reference sample that has a known quantity of a target nucleic acid, the amount of a target nucleic acid in the test sample can be determined. The reiterative abortive synthesis initiation and detection methods of the present invention can also be extended to the analysis of genetic sequence alterations in the target nucleic acid, as further described below.

Reaction Conditions

Most transcription reaction conditions are designed for the production of full length transcripts, although no conditions have been identified that eliminate abortive transcription. Appropriate reaction media and conditions for carrying out the methods of the present invention include an aqueous buffer medium that is optimized for the particular polymerase. In general, the buffer includes a source of monovalent ions, a source of divalent cations, and a reducing agent, which is added to maintain sulfhydral groups in the polymerase in a reduced form. Any convenient source of monovalent ions, such as KCl, K-acetate, $NH_4$-acetate, K-glutamate, $NH_4Cl$, ammonium sulfate, and the like, may be employed. The divalent cation may be magnesium, managanese, zinc, or the like, though, typically, the cation is magnesium (Mg). Any convenient source of magnesium cations may be employed, including $MgCl_2$, Mg-acetate, and the like. The amount of $Mg^{2+}$ present in the buffer may range from about 0.5 to 20 mM, preferably from about 1 to 12 mM.

Representative buffering agents or salts that may be present in the buffer include Tris Phosphate, Tricine, HEPES, MOPS, and the like, where the amount of buffering agent typically ranges from about 5 to 150 mM, usually from about 10 to 100 mM, and preferably from about 20 to 50 mM. In certain embodiments, the buffering agent is present in an amount sufficient to provide a pH ranging from about 6.0 to 9.5, preferably ranging from about 7.0 to 8.0. Other agents which may be present in the buffer medium include chelating agents, such as EDTA, EGTA, and the like, or other polyanionic or cationic molecules (heparins, spermidine), protein carriers (BSA) or other proteins, including transcription factors (sigma, NusA, Rho, lysozyme, GreA, GreB, NusG, etc.).

Variations in all of the reaction components potentially can alter the ratio of abortive transcripts to full-length transcripts.

Alterations in the concentration of salts (from 10 mM to 100 mM) or the use of alternative monovalent cations (K+ versus Na+ versus Rb+) have been shown to affect the level of transcription (measured as abortive transcription) on linear DNA templates (Wang, J-Y, et al., Gene 196:95-98 (1997)). Alternative sulfhydral reducing reagents are reported to have differential effects on abovtive transcription. 2-mercaptoethanol at 1-2 mM is reported to enhance abortive transcription on a poly[dA-dT] template compared to the alternative reducing agent 5,5'-dithio-bis-(2-nitrobenzoic) acid (Job, D., *Acta Biochem. Pol.* 41:415-419 ((1994)).

A high molar ratio of RNA polymerase to template enhances the frequency of abortive transcription over full length transcription on the lambda PR promoter. This effect apparently arises from collisions between tandem polymerases at the promoter.

Certain RNA polymerase mutants have elevated rates of abortive transcription compared to the wild-type polymerase. For example, a mutation changing an arginine to a cysteine at codon 529 in the RNA polymerase beta subunit gene causes elevated abortive transcriptioin at the *E. coli* pyrB1 promoter (Jin, D. J. and Turnbough, Jr., C. L., *J. Mol. Biol.* 236:72-80 (1994)).

The relative level of abortive transcription is sensitive to the nucleotide sequence of the promoter. A number of promoters have been identified that are unusually susceptible to abortive transcription (e.g., the galP2 promoter). The assay system that relies on recruitment of a defined promoter can be optimized by screening candidate promoters for maximal initiation frequency and maximal proportion of abortive transcripts.

Any aspect of the methods of the present invention can occur at the same or varying temperatures. In one embodiment, the reactions are performed isothermally, which avoids the cumbersome thermocycling process. The synthesis reaction is carried out at a temperature that permits hybridization of the various oligonucleotides, including target site probes, capture probes, and APCs, as well as the primers to the target nucleic acid template and that does not substantially inhibit the activity of the enzymes employed. The temperature can be in the range of about 25° C. to about 85° C., more preferably about 30° C. to about 75° C., and most preferably about 25° C. to about 55° C. In some embodiments, the temperature for the transcription or replication steps may be different than the temperature(s) for the preceding steps. The temperature of the transcription or replication steps can be in the range of about 25° C. to about 85° C., more preferably about 30° C. to about 75° C., and most preferably about 25° C. to about 55° C.

Denaturation of the target nucleic acid in a test sample may be necessary to carry out the assays of the present invention in cases where the target nucleic acid is found in a double-stranded form or has a propensity to maintain a rigid structure. Denaturation is a process that produces a single-stranded nucleic acid and can be accomplished by several methods that are well-known in the art. See, e.g., Sambrook et al., Molecular Cloning: A Laboratory Manual (New York, Cold Spring Harbor Laboratory Press, third edition, 2000). One method for achieving denaturation includes the use of heat, such as exposing the nucleic acid in a test sample to temperatures of about 90-100° C. for about 2-20 minutes. Alternatively, a base may be used as a denaturant when the nucleic acid comprises DNA. Many basic solutions, which are well-known in the art, may be used to denature a DNA sample. An exemplary method incubates the DNA sample with a base, such as NaOH for example, at a concentration of about 0.1 to 2.0 N NaOH at a temperature ranging from about 20° C. to about 100° C. for about 5-120 minutes. Treatment with a base, such as sodium hydroxide, not only reduces the viscosity of the sample, which increases the kinetics of subsequent enzymatic reactions, but also aids in homogenizing the sample and reducing the possibility of background by destroying any existing DNA-RNA or RNA-RNA hybrids that may exist in the sample.

In accordance with various aspects and embodiments of the invention, the target nucleic acid molecules may be hybridized to an oligonucleotide capture probe, a mononucleotide or oligonucleotide initiator which is complementary to a portion of the target nucleic acid, an APC linker sequence that is complementary to a portion of a target nucleic acid, and/or a target site probe that is complementary to regions on either side of the target site. Hybridization is conducted under standard hybridization conditions that are well-known to those skilled in the art. Reaction conditions for hybridization of an oligonucleotide (or polynucleotide) to a target sequence vary from oligonucleotide to oligonucleotide, depending upon factors such as oligonucleotide length, the number of G:C base pairs present in the oligonucleotide, and the composition of the buffer utilized in the hybridization reaction. Moderately stringent hybridization conditions are generally understood by those skilled in the art to be conditions that are approximately 25° C. below the melting temperature of a perfectly base-paired double-stranded DNA. Higher specificity is generally achieved by employing more stringent conditions, such as incubation conditions having higher temperatures. Chapter 11 of the well-known laboratory manual of Sambrook et al., Molecular Cloning: A Laboratory Manual (New York, Cold Spring Harbor Laboratory Press, 1989) describes hybridization conditions for oligonucleotide probes and primers in great detail, including a description of the factors involved and the level of stringency necessary to achieve hybridization with the desired degree of specificity.

The oligonucleotide capture probe, the target site probe, the APC, and/or the initiator may each be incubated with the target nucleic acid for about 5 to 120 minutes at about 20 to 80° C. to permit hybridization. Preferably, the target nucleic acid and the oligonucleotide probes, the APC, and/or the initiator are incubated for about 5 to 60 minutes at about 25 to 70° C. More preferably, the target nucleic acid and the oligonucleotide probes, the APC, and/or primer are incubated for about 5-30 minutes at about 35-50° C.

Hybridization is typically performed in a buffered aqueous solution and temperature conditions, salt concentration, and pH are selected to provide sufficient stringency to enable the oligonucleotide probes, the APC, or the primer to hybridize specifically to the target sequence but not to any other sequence. Generally, the efficiency of hybridization between an oligonucleotide or polynucleotide and a target nucleic acid template will be improved under conditions where the amount of oligonucleotide or polynucleotide added to the reaction mixture is in molar excess to the template, preferably a molar excess that ranges from about $10^3$ to $10^6$. It will be appreciated, however, that the amount of target nucleic acid in the test sample may not be known, so that the amount of an oligonucleotide, such as the amount of an oligonucleotide capture probe, a target site probe, or an APC for example, relative to an amount of a target nucleic acid template cannot be determined with certainty.

Alternatively, if a target DNA sequence has been treated with a base to effect denaturation, the oligonucleotide or polynucleotide is diluted in a probe diluent that also acts as a neutralizing hybridization buffer. In this manner, the pH of the test sample can be kept between about 6 and 9, which will favor the hybridization reaction and will not interfere with subsequent enzymatic reactions. Preferably, the neutralizing buffer is a 2-[bis(2-hydroxyethyl)amino]ethane sulfonic acid ("BES") (Sigma, St. Louis, Mo.) and sodium acetate buffer. More preferably, the neutralizing hybridization buffer is a mixture of 2 M BES, 1 M sodium acetate, 0.05% of an antimicrobial agent, such as $NaN_3$, 5 mM of a chelating agent, such as EDTA, 0.4% of a detergent, such as Tween-20™, and 20% of a hybridization accelerator, such as dextran sulfate. The pH of the neutralizing hybridization buffer is between about 5 to 5.5.

Transcription conditions and reagents are well-known in the art. Examples of typical conditions and reagents for RNA polymerase transcription and DNA polymerase replication are readily found in the literature. See, e.g., Chamberlain et al., The Enzymes, Boyer, ed., New York Acad. Press, 3rd ed., p. 85 (1982); Dunn et al., M. Mol. Biol. 166: 477-535 (1983)); Geider, Proc. Natl. Acad. Sci. USA 75: 645-649 (1978)); Guruvich et al., Analytical Biochem 195: 207-213 (1991); Lewis et al., J. Biol. Chem. 255: 4928-4936 (1980); Martin et al., Biochem. 27: 3966-3974 (1988); and Milligan et al., Methods Enzymol. Vol. 180a, ed., 50-52 (1989)). As described in Lu et al., U.S. Pat. No. 5,571,669, polymerase concentrations for transcription initiated from artificial transcription bubble complexes are generally about one order of magnitude higher than the ideal polymerase concentrations for promoter-initiated, or palindromic sequence-initiated, transcription.

In one embodiment, the foregoing components are added simultaneously at the initiation of the abortive synthesis and detection methods. In another embodiment, components are added in any order prior to or after appropriate timepoints during the method, as required and/or permitted by the various reaction steps. Such timepoints can be readily identified by a person of skill in the art. The enzymes used for nucleic acid detection according to the methods of the present invention can be added to the reaction mixture prior to or following the nucleic acid denaturation step, prior to or following hybridization of the primer to the target nucleic acid, prior to or following the optional hybridization of the target site probe to the target nucleic acid, or prior to or following the optional hybridization of the APC, as determined by the enzymes' thermal stability and/or other considerations known to those skilled in the art.

The various reaction steps in the methods of the invention can be stopped at various timepoints and then resumed at a later time. These timepoints can be readily identified by a person of skill in the art. Methods for stopping the reactions are known in the art, including, for example, cooling the reaction mixture to a temperature that inhibits enzyme activity. Methods for resuming the reactions are also known in the art, including, for example, raising the temperature of the reaction mixture to a temperature that permits enzyme activity. In some embodiments, one or more of the components of the various reactions may be replenished prior to, at the time of, or following the resumption of the reactions. Alternatively, the reaction can be allowed to proceed (i.e., from start to finish) without interruption.

Abortive Synthesis and Detection Methods of the Invention

The following examples of the abortive synthesis and detection methods of the invention are provided to more specifically describe the invention. These exemplary methods are intended to be merely illustrative and are not intended to limit the description provided above. It will be appreciated that various other embodiments may be practiced, given the above general description. For example, reference to the use of a primer means that any of the primers described herein may be used, including RNA initiators.

Figure 2:
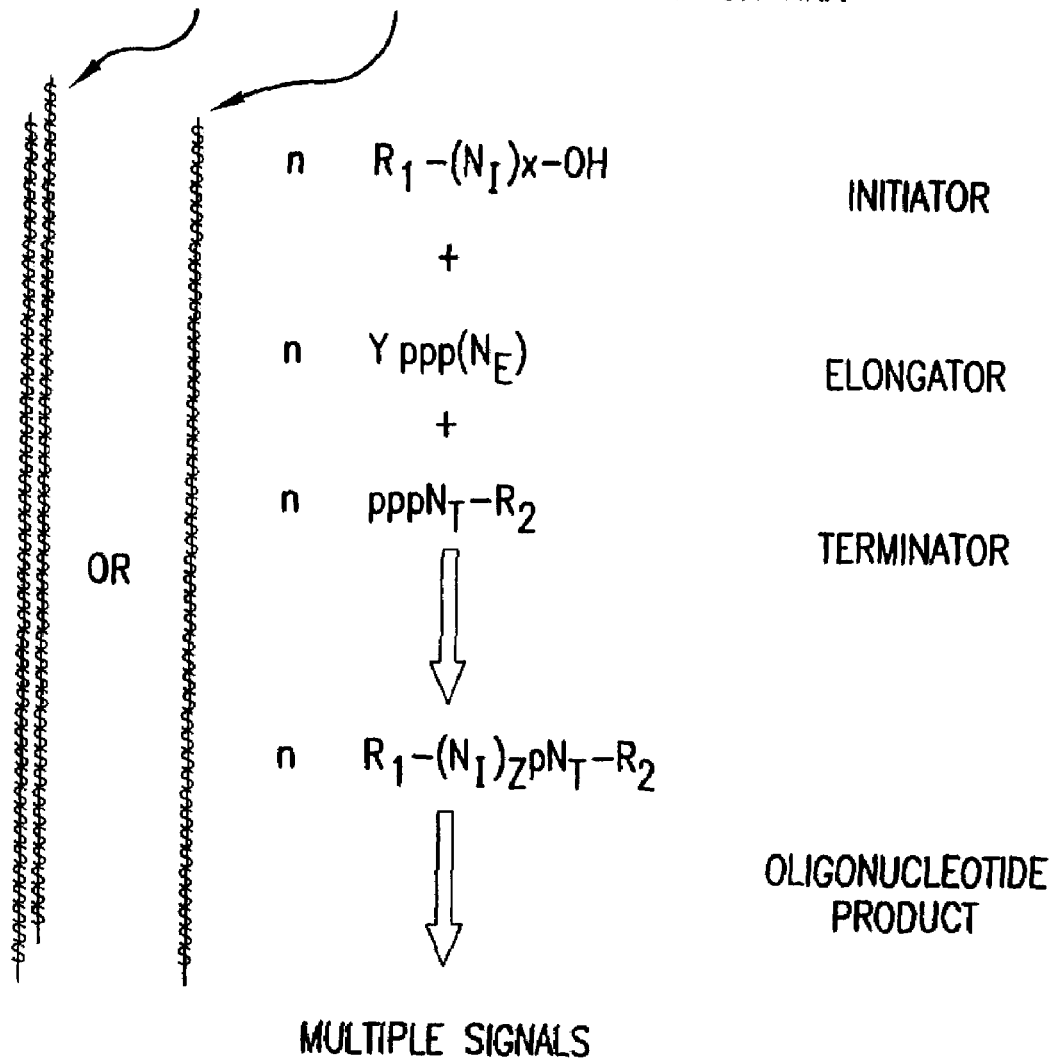
FIG. 2: Signal Generation by Reiterative oligonucleotide synthesis. A signal is generated by the enzymatic incorporation of one or more nucleotide analogs into multiple (n) highly similar or identical oligonucleotide products. Under appropriate conditions, RNA oligonucleotides can be made from nucleic acid templates in the absence of a promoter. An initiator may be comprised of one or more nucleosides, nucleoside analogs, nucleotides, or nucleotide analogs. The initiar may contain one or more covalently joined nucleotides, including but not limited to, 1-25 nucleotides, 26-50 nucleotides, 51-75 nucleotides, 76-100 nucleotides, 101-125 nucleotides, and 126-150 nucleotides, 151-175 nucleotides, 176-200 nucleotides, 201-225 nucleotides, 226-250 nucleotides and more than 250 nucleotides, and may contain a functional R group. The initiator (n copies) can be elongated directly with n copies of a terminator to end chain elongation or n copies of other elongator nucleotides (Y positions) may be incorporated between the initiator and the terminator to form a longer oligonucleotide. The terminator may contain a second functional group. $N_I$=Initiating mononucleotide or oligonucleotide analog, $N_E$=Elongating mononucleotides or analog, $N_T$=Terminating mononucleotide or analog, Z=x+y; $R_1$=H, OH, or reporter group; $R_2$=H, OH, or reporter group; N=deoxy or ribonucleotides; Polymerase =RNA-dependent or DNA-dependent RNA polymerase. DNA or RNA may be attached to other molecules, such as proteins

In accordance with an aspect of the invention, a method for detecting the presence of a target polynucleotide by generating multiple detectable oligonucleotide products through reiterative synthesis initiation events on the target polynucleotide is provided. FIG. 2 diagrammatically illustrates the various reactants that may be combined and reacted in the presence of RNA polymerase to synthesize multiple detectable oligonucleotide products. The methods of the invention may be performed using a test sample that potentially contains a target sequence. The test sequence may be detected directly or the product of primer-extension or reverse transcription of the target may be detected. Sequences or tags may be added to the copy of the target (e.g., biotin, ssDNA regions). The test sample may include double-stranded DNA, single-stranded DNA, or RNA. The DNA or RNA may be isolated and purified by standard techniques for isolating DNA or RNA from cellular, tissue, or other samples. Such standard methods may be found in references such as Sambrook et al., Molecular Cloning: A Laboratory Manual (New York, Cold Spring Harbor Laboratory Press, third edition, 2000). In one embodiment, the target nucleic acid is DNA or RNA that is in a suitable medium, although the target nucleic acid can be in lyophilized form. Suitable media include, but are not limited to, aqueous media (such as pure water or buffers). In another embodiment, the target nucleic acid is immobilized prior to being utilized as a substrate for a synthesis reaction.

In an exemplary embodiment, the target sequence is immobilized by a sequence-specific (e.g., gene-specific) oligonucleotide capture probe that is attached to a solid matrix, such as a microtiter plate. The immobilized capture probe is treated under hybridizing conditions with a test sample that includes single-stranded DNA (i.e., denatured DNA) or RNA. Any target sequence that is present in the test sample hybridizes to the capture probe and is then exposed to additional reagents in accordance with the invention.

In an exemplary embodiment, an initiator (n 5'-$R_1$-$(N_I)_x$-OH 3') hybridizes with the target sequence upstream of a target site in the presence of the target site probe (FIG. 11) and facilitates catalysis of a polymerization reaction at the target site by the polymerase. The initiation primer may be comprised of nucleosides, nucleoside analogs, nucleotides, and nucleotide analogs. The initiaor primer may vary in the number of nucleotides, such as nucleotides from 1-25 nucleotides, 26-50 nucleotides, 51-75 nucleotides, 76-100 nucleotides, 101-125 nucleotides, 126-150 nucleotides, 151-175 nucleotides, 176-200 nucleotides, 201-225 nucleotides, 226-250 nucleotides, and greater than 250 nucleotides, and may include one or more nucleotide analogs. A suitable RNA polymerase is employed to synthesize an oligoribonucleotide product from the target sequence or any portion thereof. The polymerase may be an RNA-dependent or DNA-dependent RNA polymerase. The DNA or RNA target sequence may or may not be attached to other molecules, such as proteins, for example.

During the polymerization reaction, the initiator is extended or elongated by the polymerase through the incorporation of nucleotides which have been added to the reaction mixture. As the polymerase reaction proceeds, the polymerase extends the initiator, as directed by the template sequence, by incorporating corresponding nucleotides that are present in the reaction mixture. In one embodiment, these reactant nucleotides comprise a chain terminator (e.g., n 5' pppN$_T$-$R_2$, a chain terminating nucleotide analog, as described above). When the polymerase incorporates a chain terminator into the nascent oligonucleotide product, chain elongation terminates due to the polymerase's inability to catalyze the addition of a nucleotide at the 3' position on the pentose ring of the chain terminator. Consequently, the polymerase aborts the initiated synthesis event by releasing the oligonucleotide product (i.e., 5' $R_1$-$(N_I)_z$p$N_T$-$R_2$, where z=x+y) and reinitiating the abortive initiation synthesis reaction at the target site.

The abortive initiation reaction may be controlled such that the polymerase aborts synthesis after extending the initiator by a predetermined number of nucleotides. For example, if it is desirable to terminate the synthesis reaction after the initiator has been extended by a single nucleotide, this may be accomplished by, for example, either: (1) adding to the reaction mixture only nucleotides that are chain terminators, thereby inhibiting polymerization after the first nucleotide is incorporated by the polymerase; or (2) if the genetic sequence of the target site is known, adding to the reaction mixture only a preselected chain terminating nucleotide analog (i.e., nucleotide analogs which comprise one of A, G, T, C, or U) that is complementary to the nucleotide at the target site. Alternatively, if it is desirable to terminate the synthesis reaction after the initiator has been elongated by a predetermined number of nucleotides, and if the genetic sequence of the target site is known, this may be accomplished by, for example, adding to the reaction mixture a preselected chain terminating nucleotide analog (i.e., nucleotide analogs which comprise one of A, G, T, C, or U) that is complementary to an Nth nucleotide from the target site, where N is the predetermined number of nucleotides comprised by the oligonucleotide product, exclusive of the initiator. In this manner, multiple abortive oligonucleotide products that comprise the initiator and a chain terminating nucleotide analog are synthesized by the polymerase.

The polymerase releases the oligonucleotide product without translocating from the enzyme binding site or dissociating from the target polynucleotide sequence. Nucleotide deprivation can be used to sequester the polymerase at the polymerase binding site. For example, if only an initiator and a terminator are supplied, elongation by the polymerase will not be possible.

Furthermore, reaction conditions may be optimized for abortive transcription initiation, whereby it is favorable for the polymerase to remain bound to the polymerase binding site even in the presence of elongating nucleotides. The abortive initiation reaction buffer will be optimized to increase the abortive events by adjusting the concentrations of the salts, the divalent cations, the glycerol content, and the amount and type of reducing agent to be used. In addition, "roadblock" proteins may be used to prevent the polymerase from translocating.

Figure 3:
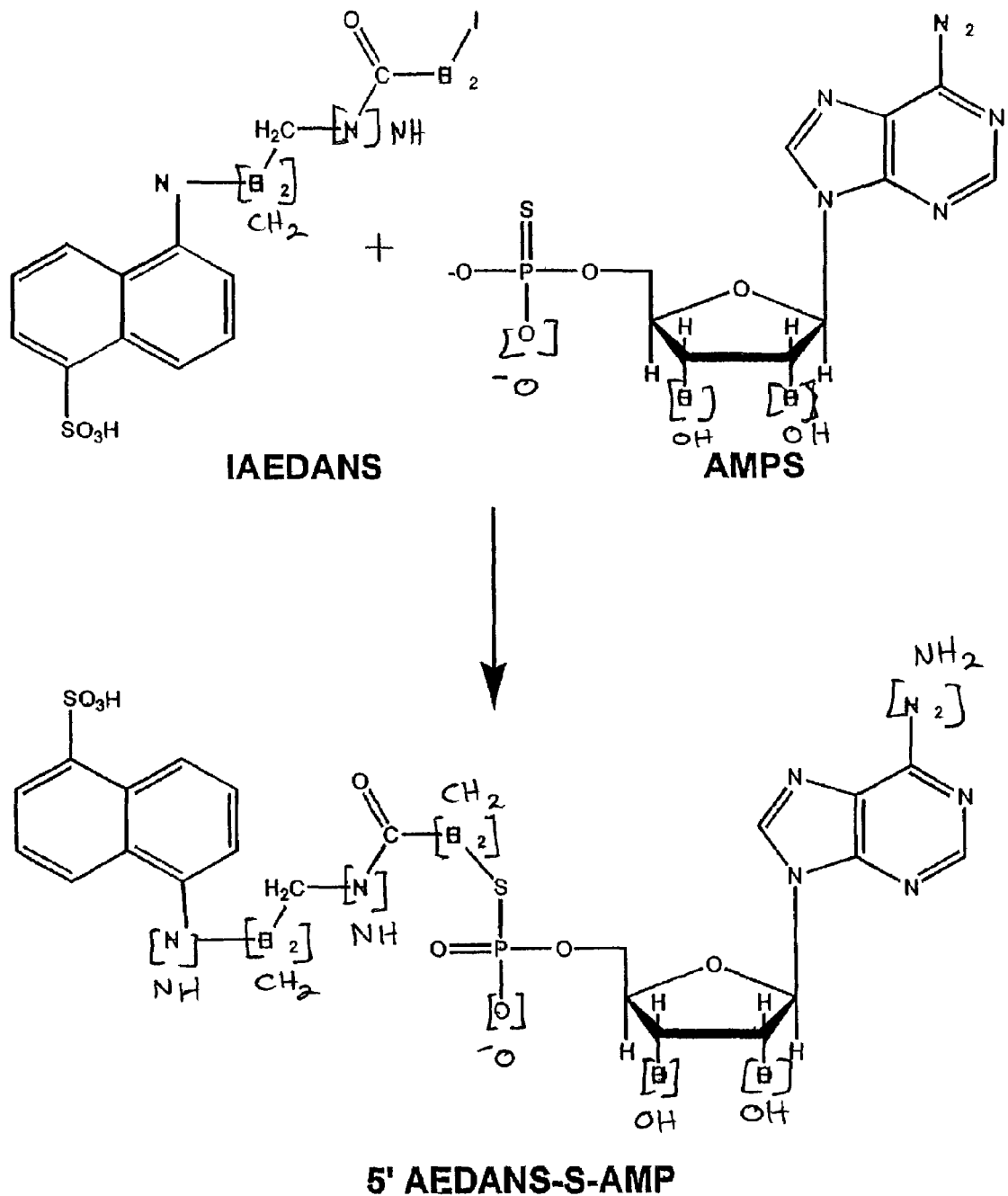
FIG. 3: 5'AEDANS-S-AMP synthesis. Example of a mononucleotide transcription initiator: IAEDANS (5-((2-((iodoacetyl)amino)ethyl)amino-1-Napthalenesulfonic acid alkylates AMPS (5-α-thio-AMP) to form the fluorescent transcription initiator. This analog can only initiate transcription because it lacks a 5' triphosphate group and can therefore not be incorporated internally or terminally.
Figure 4:
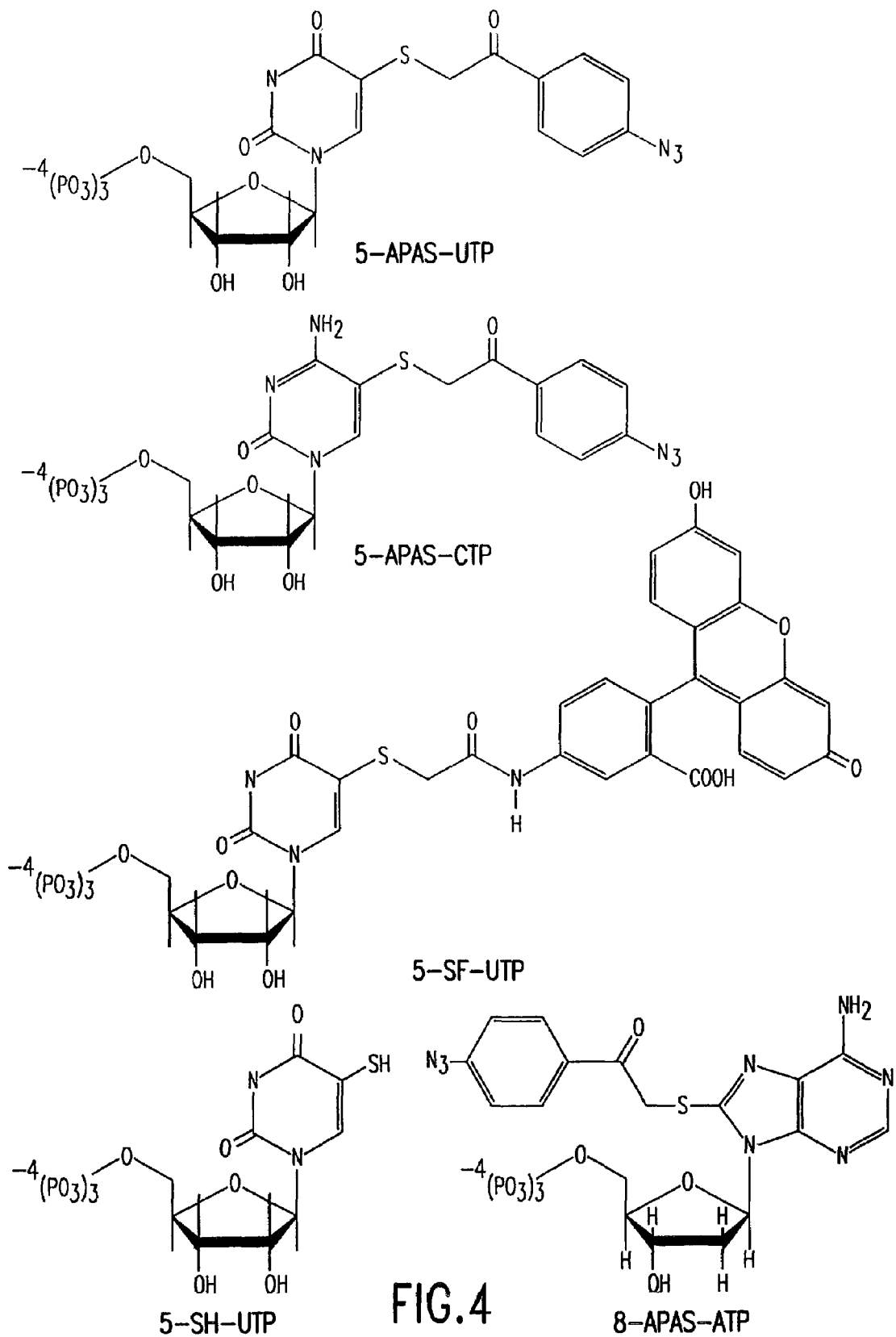
FIG. 4: Nucleotides that can be elongators or terminators. Nucleotide analogs that may be included at internal or 3' terminal positions in oligonucleotides are shown. All of these analogs can be converted to terminators simply by replacement of the 3' OH group.
Figure 5:
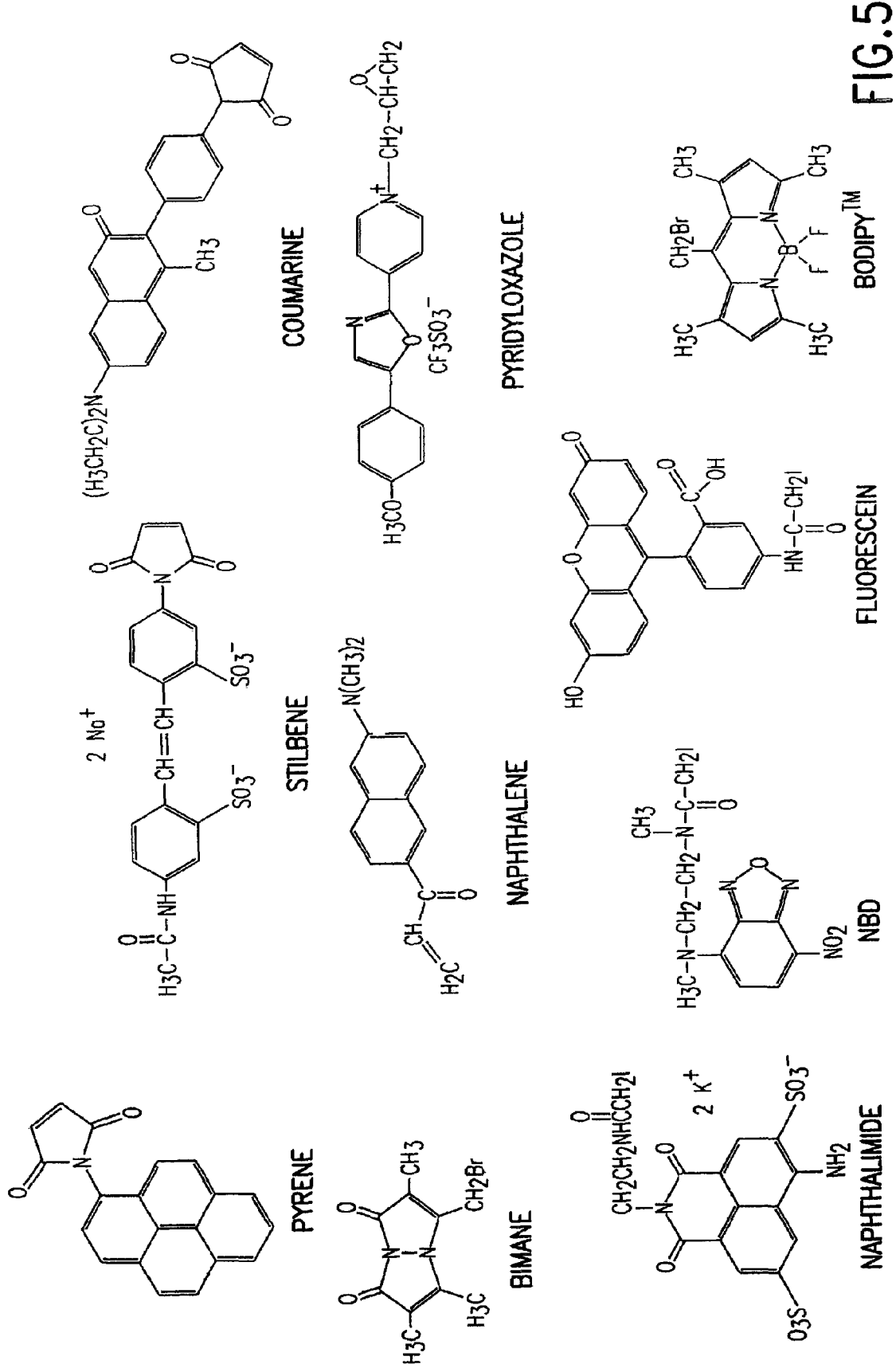
FIG. 5: Other fluorescent groups that may be $R_1$ or $R_2$. The oligonucleotides can be labeled with a variety of functional groups. Several of the preferred fluorescent groups are shown.

In another aspect of the invention, the initiator includes a moiety (e.g., $R_1$, as depicted in FIG. 2) which may be covalently bonded to the 5' phosphate group (as in FIG. 3), the 2' position of the pentose ring, or the purine or pyrimidine base of one of the nucleotides or nucleotide analogs that are incorporated into the initiator. Additionally, the reactant nucleotides and/or nucleotide analogs that are included in the reaction mixture for incorporation into the oligonucleotide product by the polymerase may each also include a moiety (e.g., $R_2$, as depicted in FIG. 2), which is covalently bonded to either the nucleobase (as in FIG. 4) or the 2' position or 3' position of the pentose ring. In an exemplary embodiment, $R_1$ and $R_2$ are label moieties (as in FIG. 5) on the initiator and the chain terminator, respectively, that are incorporated into the oligonucleotide product by the polymerase (as in FIG. 6) and are adapted to interact in a manner that generates a detectable signal (e.g., fluorescence resonance energy transfer (FRET) (FIG. 7), fluorescence or colorimetry (FIG. 8)), thereby permitting the detection and quantitation of the synthesized oligonucleotide products. In one embodiment, as illustrated in FIG. 9, an oligonucleotide product (5' $R_1$-$(N_I)_x$p$N_T$-$R_2$) incorporating an initiator ($N_I$) that has an energy donor group ($R_1$) and a chain terminating nucleotide ($N_T$) that has an energy acceptor group ($R_2$) generates a signal through fluorescence resonance energy transfer from $R_1$ to $R_2$ when the synthesized oligonucleotide products are irradiated with light of a particular wavelength. As shown in FIG. 9, when the energy donor moiety $R_1$ on the initiator is excited by exposure to light of a specified wavelength ($\lambda_{1A}$) (e.g., the absorption maximum of $R_1$) the excited donor moiety $R_1$ emits light of a second wavelength ($\lambda_{1E/2A}$) (e.g., the emission maximum for $R_1$) which is absorbable by $R_2$. If $N_T$ has been suitably incorporated into the oligonucleotide product by the polymerase, the energy acceptor moiety $R_2$ on $N_T$ is positioned sufficiently near $R_1$ on $N_I$ (e.g., within about 80 Å) to facilitate efficient energy transfer between $R_1$ and $R_2$, such that $R_2$ absorbs the wavelength of light ($\lambda_{1E/2A}$) emitted by the excited donor moiety $R_1$. In response to the absorption of $\lambda_{1E/2A}$, the excited $R_2$ acceptor moiety emits light of a third wavelength ($\lambda_{2E}$), which may then be detected and quantified in accordance with methods that are well-known in the art. Exemplary $R_1$ and/or $R_2$ FRET label moieties include aedans and fluorescein (as shown in FIG. 7), or pyrene, stilbene, coumarine, bimane, naphthalene, pyridyloxazole, naphthalimide, NBD, BODIPY™, as well as any of those described in greater detail above.

In an alternate embodiment, as diagrammatically illustrated in FIG. 10, n copies of a dinucleotide initiator (5' $R_1$-$N_1$p$N_2$-$R_2$-OH 3') comprising reporter moieties ($R_1$ and $R_2$) on either of the nucleotides ($N_1$ and $N_2$, respectively) may be extended by a polymerase to incorporate n copies of a chain terminator (5' ppp$N_3R_3$) which includes a third reporter moiety ($R_3$), yielding n copies of a detectable trinucleotide transcript (5' $R_1$-$N_1$p$N_2R_2$p$N_3$-$R_3$-OH 3'). In a manner similar to the one described above with reference to FIG. 10, the trinucleotide transcript may be irradiated with a first wavelength of light ($\lambda_{1A}$) which excites the $R_1$ energy donor group on the first nucleotide ($N_1$) to emit $\lambda_{1E}/\lambda_{3A}$. $\lambda_{3A}$ is then absorbed by the $R_3$ energy acceptor group on the chain terminating nucleotide ($N_3$), and an excited $R_3$ then emits $\lambda_{3E}$, which can then be detected and quantified. Alternatively, the transcript may be irradiated with a second wavelength of light ($\lambda_{2A}$) which excites an $R_2$ energy donor group on a second nucleotide ($N_2$) to emit $\lambda_{2E}/\lambda_{3A}$. $\lambda_{2E}/\lambda_{3A}$ is then absorbed by the $R_3$ energy acceptor group, and an excited $R_3$ then emits $\lambda_{3E}$, which can be detected and quantified. In either case, the detectable wavelength ($\lambda_{3E}$) is not obtained unless the polymerase brings an energy donor reporter moiety on the initiator ($R_1$ or $R_2$) into sufficient proximity with a corresponding energy acceptor reporter moiety ($R_3$) on the incorporated nucleotide to result in the emission of the detectable wavelength of light.

In another aspect of the invention, as diagrammatically illustrated in FIG. 11, a target site probe may be used to form a bubble complex in a target region of the target sequence. As described above, the bubble complex comprises double-stranded regions that flank a single-stranded region that includes a target site. In this embodiment, the target site probe is used to direct the polymerase to the target site by positioning the target site at the junction of the single-stranded bubble region and a downstream duplex region on the target sequence. In an exemplary embodiment, the target site probe comprises from about 18-54 nucleotides: a first region (A) which hybridizes to the target sequence (A') upstream of the target site comprises about 5-20 nucleotides; an internal, second region of non-base-paired nucleotides (B) comprises about 8-14 nucleotides; and a third region (C) which hybridizes to the target sequence downstream of the target site (C') comprises about 5-20 nucleotides. The polymerase associates with an initiator and initiates a synthesis reaction at the target site on the template sequence. The polymerase elongates the initiator to synthesize an abortive oligonucleotide product through the incorporation of nucleotides, which comprise a suitable chain terminator. Both the initiator and the nucleotides, including the chain terminating nucleotide, may be modified with a label moiety to allow signal detection, such as by fluorescence resonance energy transfer for example, as described above.

An illustrative procedure for detecting multiple oligonucleotide products through reiterative synthesis initiation events on a target sequence, therefore, may include the following process steps: (a) optionally immobilizing an oligonucleotide capture probe which is designed to hybridize with a specific or general target sequence; (b) optionally hybridizing the oligonucleotide capture probe with a test sample which potentially contains a target sequence; (c) optionally hybridizing the target sequence with a target site probe; (d) modifying at least one of an initiator and nucleotides comprising a chain terminator to enable detection of the oligonucleotide product synthesized by the polymerase; (e) hybridizing the target sequence with the primer; and (f) extending the initiator with a polymerase such that the polymerase reiteratively synthesizes an oligonucleotide product that is complementary to a target site by incorporating complementary nucleotides comprising a chain terminator and releasing an abortive oligonucleotide product without either translocating from an enzyme binding site or dissociating from the target sequence.

During transcription of the template by the RNA polymerase, the RNA initiator is extended by the RNA polymerase through the incorporation of nucleotides that have been added to the reaction mixture. As the polymerase reaction proceeds, the RNA polymerase extends the RNA initiator, as directed by the template sequence, by incorporating corresponding nucleotides that are present in the reaction mixture. In one embodiment, these reactant nucleotides comprise a chain terminator (e.g., n 5' pppN$_T$-R$_2$, a chain terminating nucleotide analog, as described above). When the RNA polymerase incorporates a chain terminator into the nascent transcript, chain elongation terminates due to the polymerase's inability to catalyze the addition of a nucleotide at the 3' position on the ribose ring of the chain terminator, and the RNA polymerase aborts the initiated transcription event by releasing the transcript and reinitiating transcription at the target site. The abortive transcription initiation reaction may be controlled such that multiple abortive oligonucleotide transcripts of a predetermined length and comprising the RNA primer and a chain terminating nucleotide analog are generated.

In an exemplary embodiment, the RNA initiator may be a mononucleotide and the nucleotides provided in the reaction mixture may comprise solely chain terminators. In this embodiment, transcription is aborted by the RNA polymerase after the RNA initiator has been extended by a single nucleotide and an abortive dinucleotide transcript is generated. In another embodiment, the RNA initiator may comprise a dinucleotide or a trinucleotide, for example, and an abortive transcription initiation event may generate an abortive transcript comprising a trinucleotide or a tetranucleotide, respectively. It will be appreciated that abortive transcripts of any desired length may be obtained, depending upon the length of the RNA initiator and the nature and composition of the reactant nucleotides that are selected for inclusion in the reaction mixture. For example, if the nucleotide sequence of the template is known, the components (e.g., target site, initiator, and reactant nucleotides) of the transcription reaction may be selected such that abortive transcripts of any desired length are generated by the method of the invention.

Figure 6:
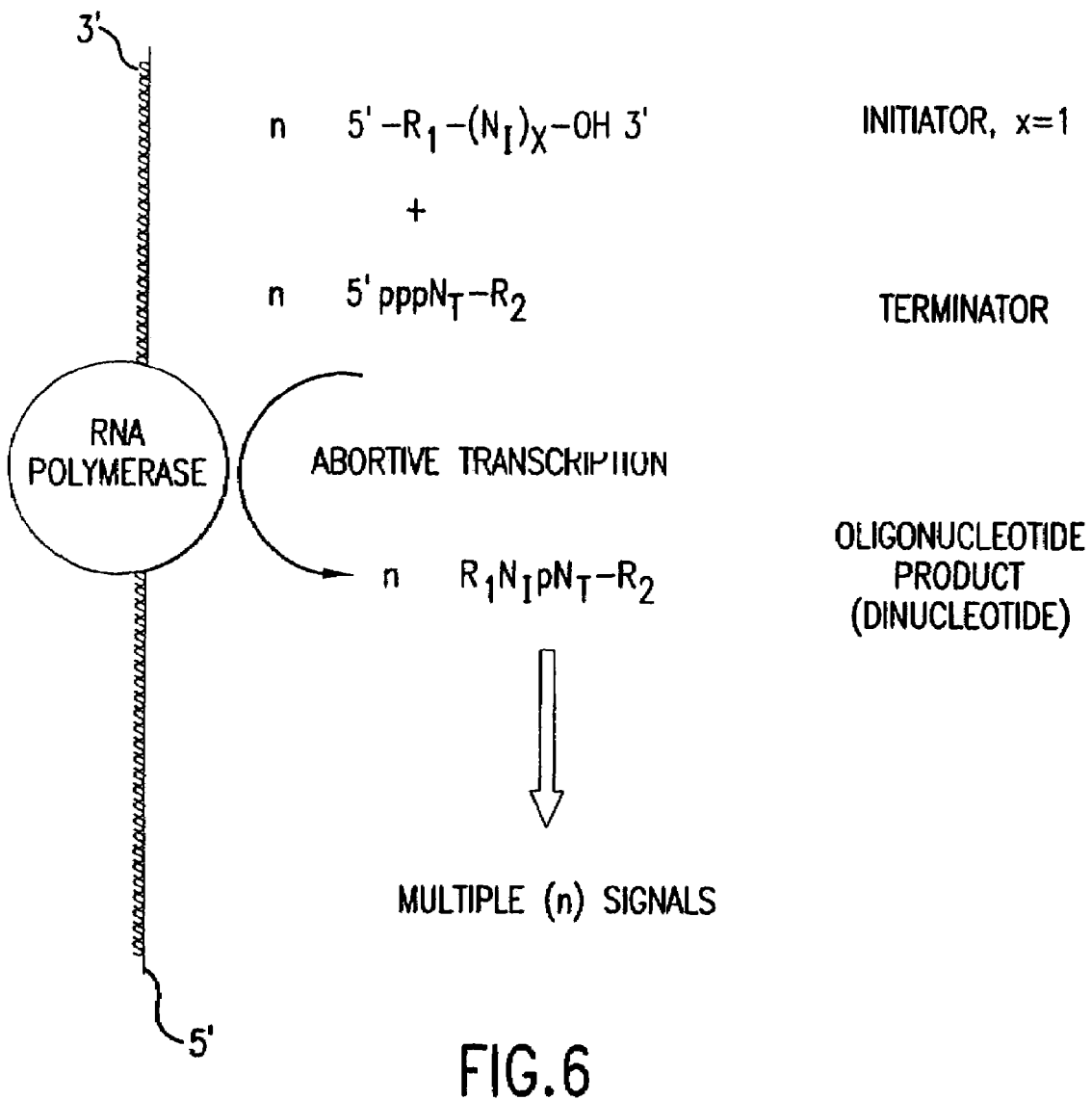
FIG. 6: Dinucleotide synthesis via abortive initiation on single-stranded DNA or RNA. Single stranded (ss) nucleic acid is DNA or RNA. Polymerase is a DNA-dependent or RNA-dependent RNA polymerase. $N_I$=3'-OH nucleoside or nucleotide initiator; $N_T$=5'-triphosphate nucleotide or nucleotide analog terminator. $R_1$ may be on the 5' phosphate group, the 2' position of the sugar, or on the purine or pyrimidine base. $R_2$ may be on the pyrimidine or purine base or 2' or 3' position of the sugar/ribose or deoxyribose. $R_1$=H, OH, and/or any reporter group or reporter group precursor, as described herein. $R_2$=H, OH, and/or any reporter group or reporter group precursor, as described herein. Signal may be any signal that can be detected, and includes but is not limited to fluorescence, fluorescence resonance energy transfer (FRET), or colorimetric. As one example, $R_1$ may be AEDANS, and $R_2$ may be Fluorescein. Signal is generated by FRET from $R_1$ to $R_2$.
Figure 7:
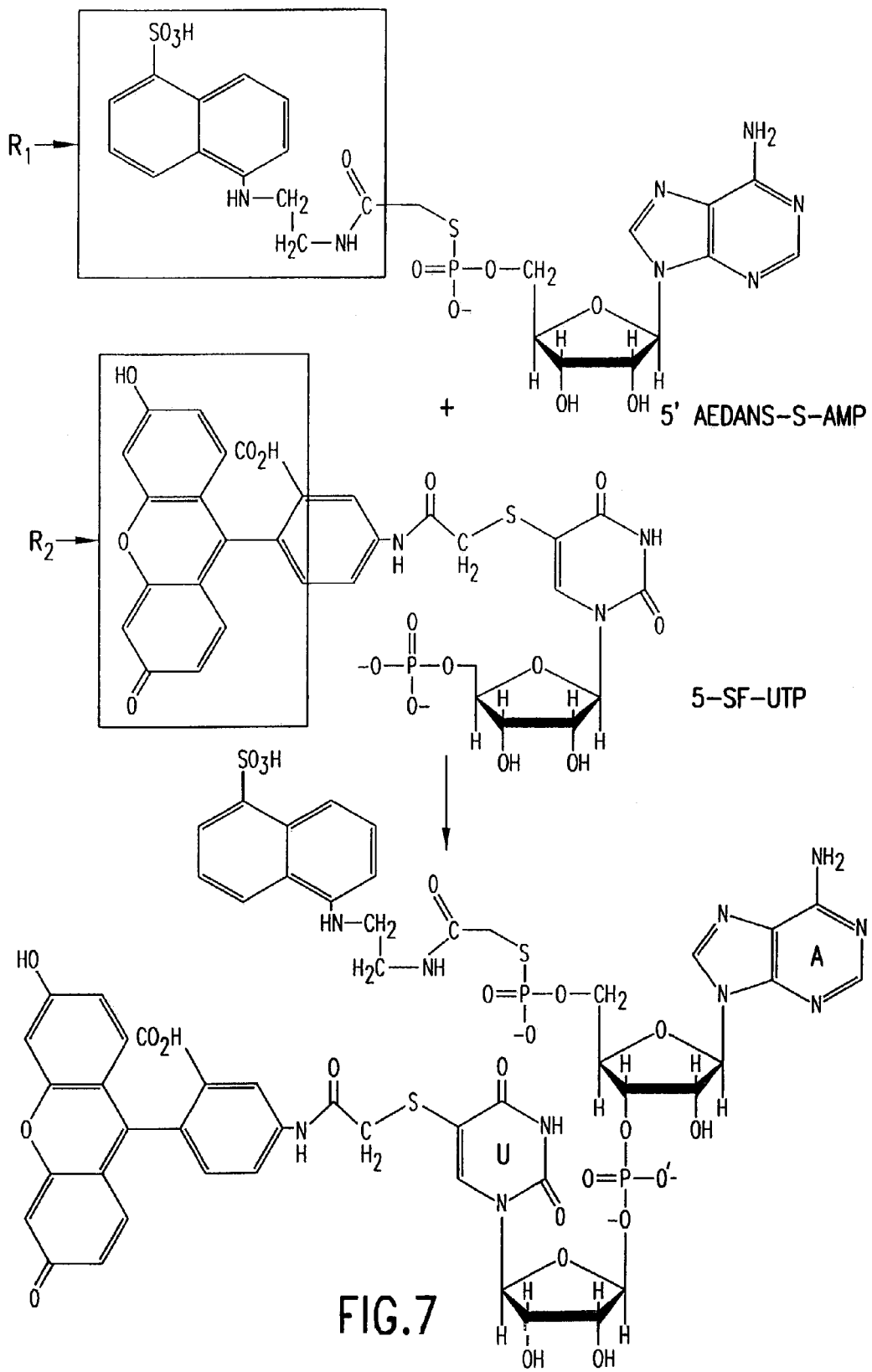
FIG. 7: 5'-AEDANS-$S_pA_p$U-FLUORESCEIN. Dinucleotide generated by abortive initiation for FRET detection. When excited by light of the appropriate wavelength, $R_1$ (AEDANS) donates fluorescent energy to $R_2$ (fluorescein), which then emits fluorescent light of a different wavelength that can be detected and quantified. This fluorescence resonance energy transfer (FRET) only occurs when the two groups are joined together to form AEDANS-SpApU-Fluorescein during transcription, which brings the two groups close enough to each other for efficient energy transfer.

In another aspect of the invention, the RNA initiator includes a moiety (e.g., $R_1$, as depicted in FIG. 6) which may be covalently bonded to the 5' phosphate group, the 2' position of the ribose ring, or the purine or pyrimidine base of one of the nucleotides or nucleotide analogs that are incorporated into the RNA initiator. Additionally, the reactant nucleotides and/or nucleotide analogs that are included in the reaction mixture for incorporation into the oligonucleotide transcript by the RNA polymerase may each also include a moiety (e.g., $R_2$, as depicted in FIG. 6), which is covalently bonded to either the nucleobase or the 2' position or 3' position of the ribose ring. The moieties $R_1$ and $R_2$ may each comprise H, OH, or any suitable label moiety, reporter group, or reporter group precursor, as described in greater detail above.

An illustrative procedure for detecting multiple oligonucleotide transcripts through reiterative transcription initiation events on a target sequence, therefore, may include the following process steps: (a) optionally immobilizing an oligonucleotide capture probe which is designed to hybridize with a specific or general target sequence; (b) optionally hybridizing the oligonucleotide capture probe with a test sample which potentially contains a target sequence; (c) optionally hybridizing the target sequence with a target site probe; (d) modifying at least one of an RNA initiator and nucleotides comprising a chain terminator to enable detection of the oligonucleotide transcript synthesized by the RNA polymerase; (e) hybridizing the target sequence with the RNA initiator; and (f) extending the RNA initiator with an RNA polymerase such that the RNA polymerase reiteratively synthesizes an oligonucleotide transcript that is complementary to a target site by incorporating complementary nucleotides comprising a chain terminator and releasing an abortive oligonucleotide transcript without substantially translocating from the polymerase binding site or dissociating from the target sequence.

Figure 8:
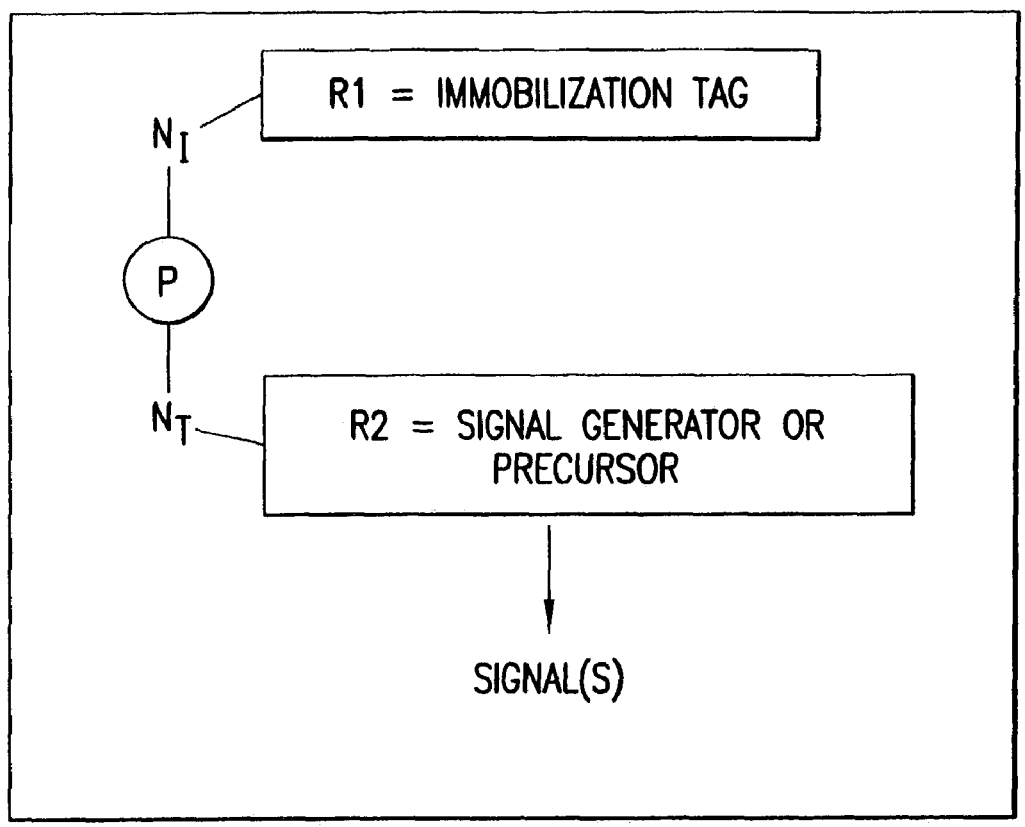
FIG. 8: Signal generation via dinucleotide production. Oligonucleotides can be synthesized that contain one R group on the initiator nucleotide and another on the terminator nucleotide, such that the R groups have different functions. For example, if $R_1$ is biotin, it can be used for oligonucleotide product immobilization and $R_2$ allows for signal production.

In accordance with another aspect of the invention, as diagrammatically illustrated in FIG. 8, the methods of the invention may be utilized to generate an oligonucleotide product (5' $R_1$-$(N_1)_x$pN$_T$-R$_2$) which comprises an initiator ($N_I$) with a moiety ($R_1$), such as an immobilization tag for example; and a chain terminating nucleotide ($N_T$) that includes a label moiety ($R_2$), such as a signal generator or signal generator precursor for example. In this embodiment, the oligonucleotide product(s) may be captured or immobilized, such as on a membrane for example, to facilitate detection of the oligonucleotide products of the abortive synthesis reaction. In an exemplary embodiment, $R_1$ is a bioadhesive tag, such as biotin for example; $R_2$ is a label moiety, such as fluorescein for example; and oligonucleotide products that are attached to the solid matrix by the $R_1$ bioadhesive tag are capable of direct detection through an emission from the $R_2$ label moiety. In another exemplary embodiment, an antibody, such as anti-dinitrophenyl (anti-DNP) for example, is attached to the solid matrix; $R_1$ is an immobilization tag, such as dinitrophenyl (DNP) for example; $R_2$ is a reporter or reporter precursor, such as a reactive thiol for example; and, upon silver/gold development, the oligonucleotide products that are attached to the solid matrix by the $R_1$ tag produce a colored signal that is visible to the naked eye without irradiation.

Applications of the Abortive Synthesis and Detection Methods of the Invention

The methods of the present invention can be used in a variety of diagnostic contexts. For purposes of illustration, methods of assessing the methylation state of specific genes, detecting the presence of known genetic mutations, detecting the presence of pathogenic organisms, detecting mRNA expression levels, and detecting and amplifying proteins are described.

DNA Methylation

The methods of the present invention may be used in diagnostic assays which detect epigenetic changes associated with disease initiation and progression by assessing the methylation state of specific genes and their regulatory regions that are known to be associated with particular disease-states. DNA methylation is a cellular mechanism for altering the properties of DNA without altering the coding function of that sequence. The methylation reaction, which is catalyzed by DNA-(cytosine-5)-methyltransferase, involves the transfer of a methyl group from S-adenosylmethionine to the target cytosine residue to form 5-methylcytosine (5-mCyt) (FIG. 12). See Gonzalgo et al., U.S. Pat. No. 6,251,594. The areas of the genome that contain 5-mCyt at CpG dinucleotides are referred to as "CpG islands." While changes in the methylation status of the cytosine residues in DNA CpG islands commonly occur in aging cells, altered gene methylation (either increased or decreased) is frequently an early and permanent event in many types of disease, including cancer. CpG islands tend to be found in DNA regulatory regions that are near genes and determine whether these genes are either active or inactive. Many genes that regulate cell growth, and therefore prevent or inhibit the development of cancer, such as tumor suppressor genes, must be active (unmethylated) to promote normal cell growth. Other genes, such as oncogenes for example, must be inactive (methylated) so as not to promote abnormal cell growth.

For example, many types of cancer are associated with a distinct combination or pattern of CpG island methylation. FIG. 16 graphically illustrates the manner in which altered gene methylation may be associated with various types of cancer. The graph plots 13 exemplary cancers (prostate, kidney, bladder, esophageal, lung, gastric, colon, blood, breast, skin, brain, liver, and ovarian) against 49 genes which have been shown to have methylation changes that are associated with the initiation and progression of the identified types of cancer. Each oval in the graph (coded by cancer type) indicates an abnormal methylation status for a gene (i.e., methylated when its normal status is unmethylated or unmethylated when its normal status is methylated). Since each type of cancer may be associated with a different pattern of methylation-altered genes, cancer-affected organs may potentially be identified based upon organ-specific combinations of methylated genes. For example, in the case of prostate cancer cells, genes 4, 9, 10, 14, 19, 22, 32, and 33 have been shown to exhibit abnormal methylation states. Thus, if standardized diagnostics could easily evaluate the methylation states of these 8 genes, then the initiation, progression, and recurrence of prostate cancer could be readily monitored and more effective patient treatment strategies could be developed. It will be appreciated that FIG. 16 represents only a subset of the genes for which altered methylation states and patterns are indicative of various types of cancer.

In an exemplary embodiment, the methods of the invention may be utilized to monitor disease initiation, progression, metastasis, recurrence, and any responses to treatment therapies by providing diagnostic techniques, which can detect altered methylation states and patterns. Methylated cytosine residues in a DNA fragment can be detected based upon the resistance of such residues to deamination by a deaminating agent, such as sodium bisulfite for example. When denatured (i.e., single-stranded) DNA is exposed to a deaminating agent, such as sodium bisulfite, unmethylated cytosine (C) residues are converted into uracil residues (U), while methylated cytosine residues (5-mCyt) remain unchanged. That is, as illustrated in FIG. 14, deamination resulting from a treatment with sodium bisulfite causes the originally unmethylated cytosines to change their complementary base-pairing partner from guanine (G) to adenosine (A). However, the methylated cytosines (5-mCyt) retain their base-pairing specificity for G. Thus, after deamination by sodium bisulfite, a target DNA sequence will have only as many complementary CpG islands as there were methylated CpG islands in the original, untreated target DNA sequence. Additionally, as further illustrated in FIG. 14, if an original, untreated target DNA sequence has no methylated CpG islands, then the bisulfite-treated target DNA sequence will no longer contain any CpG islands.

In view of the foregoing, the level of methylation of the CpG islands in a target DNA sequence may be determined by measuring the relative level of unaltered CpG sites. This relative measurement may be accomplished by initiating abortive transcription at the CpG sites that remain after the target DNA sequence has been exposed to a deaminating agent, such as sodium bisulfite. The sodium bisulfite reaction is performed according to standard techniques. See, e.g., Gonzalgo et al., U.S. Pat. No. 6,251,594. In one embodiment, as illustrated in FIG. 15, a sodium bisulfite-treated DNA target sequence can be incubated with an RNA polymerase and an initiator, such as a mononucleotide initiator (5' $R_1$-C-OH 3') for example. The initiator associates with the polymerase and initiates transcription and RNA synthesis at an intact CpG site on the DNA template. Each CpG site can direct the extension of an initiator to synthesize an abortive transcript (e.g., 5' $R_1$-CpG-$R_2$ 3') through the incorporation of a suitable chain terminator (e.g., pppG-$R_2$), as illustrated at Sites 1, 3, and 4 in FIG. 15. Either or both of the initiator and a chain terminating nucleotide may be modified with a label moiety (e.g., $R_1$ and $R_2$, respectively) to allow signal detection. In an exemplary embodiment, the transcripts may be detected through fluorescence resonance energy transfer (FRET) for example, as described in detail above (e.g., the primer contains an energy donor ($R_1$) at its 5'-end, and the NTP contains an energy acceptor ($R_2$) attached to the nucleobase).

In an alternate embodiment, a sodium bisulfite-treated DNA target sequence may be incubated with an RNA polymerase and a dinucleotide initiator (5' $R_1$-CpG-OH 3'). The initiator then associates with the polymerase and initiates transcription and RNA synthesis at an intact CpG site on the DNA template. Each CpG site then directs the extension of the dinucleotide initiator to synthesize an abortive trinucleotide transcript through the incorporation of a suitable chain terminator. The nucleotide analog that comprises the chain terminator will depend upon the DNA template sequence. For example, at Site 1 of FIG. 15, a suitable chain terminator would include 5' pppA-$R_{23}$', and the resultant abortive trinucleotide transcript would be 5' $R_1$-CpGpA-$R_2$ 3'.

In another embodiment, as diagrammatically illustrated in FIG. 15, after the target DNA sequence has been deaminated, such as by treating the target DNA sequence with sodium bisulfite for example, a target site probe may be used to form a bubble complex that comprises a target CpG site on the target DNA sequence. In this embodiment, the target site probe is used to direct the RNA polymerase to the target CpG site by positioning the target CpG site at the junction of a single-stranded bubble region and a downstream duplex region on the target DNA sequence. In the illustrated embodiment, the target site probe comprises about 18-54 nucleotides: a first region which hybridizes to the target DNA sequence upstream of the target site comprises about 5-20 nucleotides; an internal second region of non-base-paired nucleotides comprises about 8-14 nucleotides; and a third region which hybridizes to the target DNA sequence downstream of the target site comprises about 5-20 nucleotides. The target site probe may be hybridized to the target DNA sequence either before or while the DNA target sequence is incubated with an RNA polymerase and a suitable RNA initiator. The polymerase associates with the RNA initiator and initiates transcription and RNA synthesis at the CpG site on the DNA template. The polymerase extends the initiator to synthesize an abortive oligonucleotide transcript through the incorporation of a suitable chain terminator. Either or both of the initiator and a chain terminating nucleotide may be modified with a label moiety to allow signal detection, such as by fluorescence resonance energy transfer for example, as described in detail above.

In another embodiment, capture probes may be designed to capture the genes of interest, and abortive transcription initiation used to determine the methylation status of the desired genes. For example, genes known to be associated with the progression of a particular cancer, such as colon cancer, may be monitored, including but not limited to APC (adenomatous polyposis coli), CALCA (calcitonin), ER (estrogen receptor), GSTP1, HIC1 (hypermethylated in cancer-1), hMLH1, HPP1/TR/TENB2/TMEFF2 (Transmembrane protein with EFG-like and two follistatin-like domains 2), LKB1/STK11. IGF2 IGF2 (Insulin-like growth factor), MGMT ($O^6$ methyl guanine methyl transferase 1), MINT25, p14(ARF), p16 (INK4a)/MTSI/CDKN2A, PAX6 (paired box gene 6), RAR-Beta2, THBS1 (thrombospondin-1), Veriscan, and WT1 (Wilm's tumor suppressor). Each gene of interest could be removed from the sample by hybridization to a capture sequence, which is unique for the gene of interest. The capture sequence may be immobilized on a solid matrix, including but not limited to magnetic beads, microtiter plates, sepharose, agarose, cation exchange resins, lateral flow strips, glass beads, and microarray chips. Once the gene of interest has been removed from the sample, abortive transcription initiation can be used to determine the methylation status for each particular gene.

An illustrative procedure for detecting DNA methylation states and patterns, therefore, may include the following process steps: (a) optionally immobilizing an oligonucleotide capture probe which is specific for a region near a CpG island of a target gene; (b) optionally treating the oligonucleotide capture probe with a denatured DNA sample which potentially contains a target DNA sequence; (c) converting any unmethylated cytosine residues on the target DNA sequence to uracil residues and leaving any methylated cytosine residues unaltered; (d) optionally hybridizing the target DNA sequence with a target site probe; (e) modifying at least one of an RNA initiator and nucleotides comprising a chain terminator to enable detection of the oligonucleotide transcript; (f) hybridizing the target DNA with the RNA initiator; and (g) extending the RNA initiator with an RNA polymerase such that the RNA polymerase reiteratively synthesizes an oligonucleotide transcript that is complementary to a target site by incorporating complementary nucleotides comprising a chain terminator and releasing an abortive oligonucleotide transcript without either translocating from an enzyme binding site or dissociating from the target DNA sequence; and (g) detecting and optionally quantifying the multiple abortive oligonucleotide transcripts.

Genetic Mutations

In another aspect of the invention, the methods disclosed herein may be used in diagnostic assays which detect mutations in the form of gross chromosomal rearrangements or single or multiple nucleotide alterations, substitutions, insertions, or deletions. In an exemplary embodiment, as diagrammatically illustrated in FIG. 17, single nucleotide polymorphisms (SNPs) may be detected through the use of an abortive oligonucleotide synthesis reaction. A known target SNP sequence (e.g., 3' $dN_X$-$pdN_Y$-$pdN_T$, 5', where $dN_T$, is a target SNP site) can be incubated with an RNA polymerase, an RNA initiator, such as a dinucleotide initiator for example, and nucleotides (e.g., a chain terminator such as 5' $pppN_T$-$R_2$). The initiator binds immediately upstream of the target SNP sequence, associates with the polymerase, and initiates transcription and RNA synthesis at the target SNP site. In one embodiment, the polymerase elongates the initiator by incorporating the chain terminator to produce an abortive trinucleotide product. Either or both of the initiator and a chain terminating nucleotide may be modified with a label moiety ($R_1$ and $R_2$, respectively) to allow signal detection. In an exemplary embodiment, the transcripts may be detected through fluorescence resonance energy transfer (FRET) for example, as described in detail above (e.g., the initiator contains an energy donor ($R_1$) at its 5'-end, and the chain terminator contains an energy acceptor ($R_2$) attached to the nucleobase).

An illustrative procedure for detecting mutations in a target DNA sequence (FIG. 18), therefore, may include the following process steps: (a) optionally immobilizing a capture probe designed to hybridize with a target DNA sequence which includes a mutation; (b) optionally hybridizing the capture probe with a DNA sample which potentially contains the target DNA sequence; (c) optionally hybridizing the target DNA sequence with a target site probe; (d) modifying at least one of an RNA initiator ($R_1N_T$-OH) and nucleotides comprising a chain terminator ($pppN_T$-$R_2$) to enable detection of the oligonucleotide transcript synthesized by the RNA polymerase; (e) hybridizing the target DNA sequence with the RNA initiator; (f) extending the RNA initiator with an RNA polymerase such that the RNA polymerase reiteratively synthesizes an oligonucleotide transcript that is complementary to a target mutation site by incorporating complementary nucleotides comprising a chain terminator and releasing an abortive oligonucleotide transcript without either translocating from an enzyme binding site or dissociating from the target DNA sequence; and (g) detecting and optionally quantifying the multiple abortive oligonucleotide transcripts.

Pathogenic Organisms

In another aspect of the invention, the methods disclosed herein may be used in diagnostic assays which detect the presence of a particular nucleic acid (DNA or RNA), thereby serving to indicate the presence of either a particular or a generic organism which contains the gene, or which permit genetic typing of a particular organism without the need for culturing the organism. The test sample may be suspected of containing a target nucleic acid sequence from a particular microorganism, such as bacteria, yeast, viruses, viroids, molds, fungi, and the like. The test sample may collected from a variety of sources including but not limited to, animal, plant or human tissue, blood, saliva, semen, urine, sera, cerebral or spinal fluid, pleural fluid, lymph, sputum, fluid from breast lavage, mucuosal secretions, animal solids, stool, cultures of microorganisms, liquid and solid food and feedproducts, waste, cosmetics, air, and water.

In another aspect of the invention, the methods disclosed herein may be used in diagnostic assays which detect the presence of a particular nucleic acid (DNA or RNA), thereby serving to indicate the presence of either a particular or a generic pathogenic organism which contains the gene, or which permit genetic typing of a particular organism without the need for culturing the organism. In an exemplary embodiment, as diagrammatically illustrated in FIG. 19, an oligonucleotide capture probe that is sequence-specific for a target pathogen polynucleotide is attached to a solid matrix, such as a microtiter plate for example, and the capture probe is treated under hybridizing conditions with a test sample which potentially contains the target pathogen polynucleotide. The test sample may be suspected of containing a target nucleic acid sequence from a particular pathogen, such as, for example, a microorganism, such as bacteria, yeast, viruses, viroids, molds, fungi, and the like. The test sample may collected from a variety of sources including but not limited to, animal, plant or human tissue, blood, saliva, semen, urine, sera, cerebral or spinal fluid, pleural fluid, lymph, sputum, fluid from breast lavage, mucusoal secretions, animal solids, stool, cultures of microorganisms, liquid and solid food and feedproducts, waste, cosmetics, air, and water.

The target pathogen polynucleotide may be either RNA or DNA. A target pathogen polynucleotide that is present in the test sample hybridizes- to the capture probe, and a washing step is then performed to remove any components of the test sample that were not immobilized by the capture probe. Target DNA or RNA may be retrieved by addition of specific sequences via primer extension, for example. In an exemplary embodiment, the captured target pathogen polynucleotide is hybridized with an abortive promoter cassette (APC). The APC linker sequence includes a single-stranded overhang region on either its 3' or 5' end (depending upon the orientation needed to create an antiparallel hybrid with the capture probe). In other words, the APC linker is complementary to the sequence on the free end of the captured target pathogen polynucleotide, thereby permitting the APC linker to hybridize to the target pathogen polynucleotide.

An initiator and a polymerase are added to the reaction mixture. The initiator hybridizes within the bubble region of the APC at a position that facilitates catalysis of a synthesis reaction by a suitable polymerase at the target site. The initiator may be RNA or DNA, may comprise from about 1 to 25 nucleotides, and may include one or more nucleotide analogs as well as nucleotides. The polymerase may be an RNA-dependent or DNA-dependent RNA polymerase. The DNA or RNA APC may or may not be attached to other molecules, such as proteins, for example. In an exemplary embodiment, the APC comprises DNA, the initiator is RNA, and the polymerase is a DNA-dependent RNA polymerase.

During the polymerization reaction, the initiator is extended or elongated by the polymerase through the incorporation of nucleotides that have been added to the reaction mixture. As the polymerase reaction proceeds, the polymerase extends the initiator, as directed by the APC template sequence within the bubble region, by incorporating complementary nucleotides, including a suitable chain terminator, that are present in the reaction mixture. When the polymerase incorporates a chain terminator into the nascent oligonucleotide product, chain elongation terminates due to the polymerase's inability to catalyze the addition of a nucleotide at the 3' position on the pentose ring of the incorporated chain terminator. Consequently, the polymerase aborts the initiated synthesis event by releasing the oligonucleotide product and reinitiating the synthesis reaction at the target site. Either or both of the initiator and a chain terminating nucleotide may be modified with a label moiety to allow signal detection. In an exemplary embodiment, the oligonucleotide products may be detected through fluorescence resonance energy transfer (FRET), as described above (e.g., the initiator contains an energy donor ($R_1$) at its 5'-end, and the chain terminator contains an energy acceptor ($R_2$) attached to the nucleobase).

An illustrative procedure for detecting the presence of pathogens (FIG. 20), therefore, may include the following process steps: (a) optionally immobilizing a capture probe designed to hybridize with a target pathogen polynucleotide; (b) optionally hybridizing the capture probe with a test sample which potentially contains a target pathogen polynucleotide. The target nucleic acid may be copied to DNA via reverse transcription (for RNA pathogens) or primer extension (for DNA pathogens). In both bases, a DNA sequence corresponding to the Abortive Promoter Cassette (APC) linker will be added to the target copy (FIG. 1); (c) optionally washing the captured target pathogen polynucleotide to remove any unhybridized components of the test sample; (d) hybridizing the captured target pathogen polynucleotide with an abortive promoter cassette; (e) modifying at least one of a initiator and nucleotides comprising a chain terminator to enable detection of the oligonucleotide product synthesized by the polymerase; (f) hybridizing the abortive promoter cassette with a initiator; (g) extending the initiator with a polymerase such that the polymerase reiteratively synthesizes an oligonucleotide product that is complementary to a target site by incorporating complementary nucleotides comprising a chain terminator and releasing an abortive oligonucleotide product without either translocating from an enzyme binding site or dissociating from the APC; and (h) detecting and optionally quantifying the multiple abortive oligonucleotide products.

The present invention is useful for detecting pathogens in mammals. Tin particular the invention is useful for the detection of bacteria, viruses, fungus, molds, amoebas, prokaryotes, and eukaryotes. Preferred mammals include monkeys, apes, cats, dogs, cows, pigs, horses, rabbits and humans. Particularly preferred are humans.

The methods of the invention are particularly useful for monitoring the presence or absence of pathogenic nucleic acids and proteins. The invention can be used to detect, diagnose, and monitor diseases, and/or disorders associated with pathogenic polypeptides or polynucleotides. The invention provides for the detection of the aberrant expression of a polypeptide or polynucleotide. The method comprises (a) assaying the expression of the polypeptide or polynucleotide of interest in cells, tissue or body fluid of an individual using the methods of abortive initiation transcription described above, and (b) comparing the level of gene expression, protein expression, or presence of sequences of interest with a standard gene or protein expression level or seqeunce of interest, whereby an increase or decrease in the assayed polypeptide or polynucleotide level compared to the standard level is indicative of aberrant expression indicating presence of a pathogen of interest.

The presence of an abnormal amount of transcript in biopsied tissue or body fluid from an individual may provide a means for detecting the disease prior to the appearance of actual clinical symptoms. A more definitive diagnosis of this type may allow health professionals to employ preventative measures or aggressive treatment earlier thereby preventing the development or further progression of the disease caused by the pathogen.

The invention is particularly useful for monitoring the presence of pathogenic organisms including but not limited to *E. coli*, Steptococcus, *Bacillus, Mycobacterium*, HIV, and Hepatitis.

The methods of the invention may be used to test for pathogenic microorganisms in aqueous fluids, in particular water (such as drinking water or swimming or bathing water), or other aqueous solutions (such as fermentation broths and solutions used in cell culture), or gases and mixtures of gases such as breathable air, and gases used to sparge, purge, or remove particulate matter from surfaces. Breathable air from any source including but not limited to homes, schools, classrooms, workplaces, aircraft, spacecraft, cars, trains, buses, and any other building or structure where people gather, may be tested for the presence of pathogenic microorganisms.

mRNA Expression

In another aspect of the invention, the methods disclosed herein may be used in diagnostic assays which detect messenger RNA (mRNA) expression levels in a quantitative or non-quantitative manner. In an exemplary embodiment, as diagrammatically illustrated in FIG. 21, an oligonucleotide capture probe that is sequence-specific for a target mRNA sequence is attached to a solid matrix, such as a microtiter plate for example, and the capture probe is treated under hybridizing conditions with a test sample which is suspected of containing the target mRNA sequence. A target mRNA sequence that is present in the test sample hybridizes to the capture probe, and a washing step is then performed to remove any components of the test sample that were not immobilized by the capture probe. The captured target mRNA sequence is then hybridized with an abortive promoter cassette (APC). In the illustrated embodiment, the APC has an APC linker sequence which includes a single-stranded poly-T overhang on its 3' end that is complementary to the poly-A tail on the 3' end of the target mRNA sequence, thereby permitting the APC linker to hybridize to the poly-A tail of the target mRNA.

An initiator and a polymerase are added to the reaction mixture. The initiator hybridizes within the bubble region of the APC, upstream of the target site, and facilitates catalysis of a synthesis reaction by a suitable polymerase at the target site. The initiator may comprise from about 1 to 25 nucleotides, and may include one or more nucleotide analogs as well as nucleotides. The polymerase may be an RNA-dependent or DNA-dependent RNA polymerase. The APC may or may not be attached to other molecules, such as proteins, for example. In an exemplary embodiment, the APC comprises DNA, the initiator is RNA, and the polymerase is a DNA-dependent RNA polymerase.

During the polymerization reaction, the initiator is extended or elongated by the polymerase through the incorporation of nucleotides which have been added to the reaction mixture. As the polymerase reaction proceeds, the polymerase extends the initiator, as directed by the APC template sequence within the bubble region, by incorporating complementary nucleotides, including a chain terminator, that are present in the reaction mixture. When the polymerase incorporates a chain terminator into the nascent oligonucleotide product, chain elongation terminates due to the polymerase's inability to catalyze the addition of a nucleotide at the 3' position on the pentose ring of the incorporated chain terminator. Consequently, the polymerase aborts the initiated synthesis event by releasing the oligonucleotide product and reinitiating the synthesis reaction at the target site. Either or both of the initiator and a chain terminating nucleotide may be modified with a label moiety to allow signal detection, such as by fluorescence resonance energy transfer for example, as described in detail above.

An illustrative procedure for detecting mRNA expression levels, therefore, may include the following process steps: (a) optionally immobilizing a capture probe designed to hybridize with a specific or general mRNA sequence; (b) optionally hybridizing the capture probe with a test sample which potentially contains a target mRNA sequence; (c) optionally washing the captured target mRNA sequence to remove any unhybridized components of the test sample; (d) hybridizing the captured target mRNA sequence with an abortive promoter cassette; (e) modifying at least one of a initiator and nucleotides comprising a chain terminator to enable detection of the oligonucleotide product synthesized by the polymerase; (f) hybridizing the abortive promoter cassette with the initiator; (g) extending the initiator with a polymerase such that the polymerase reiteratively synthesizes an oligonucleotide product that is complementary to a target site by incorporating complementary nucleotides comprising a chain terminator and releasing an abortive oligonucleotide product without either translocating from an enzyme binding site or dissociating from the APC; and (h) detecting and optionally quantifying the multiple abortive oligonucleotide products.

Protein Detection

In another aspect of the invention, the methods disclosed herein may be used in diagnostic assays which detect proteins. As shown in FIG. 22, an abortive promoter cassette linker can be made with a protein modifier group attached, such that the linker is complementary to the APC linker attached to the APC.

An illustrative procedure for detecting proteins, therefore, may include the following process steps: (a) attaching a short piece of DNA of a defined sequence (APC linker) to a protein via a primary amine, a secondary amine, or a sulfhydral group; (b) retrieving and immobilizing the modified protein with an antibody or some other affinity agent against the protein; and (c) attaching an abortive promoter cassette to the protein by hybridization of the APC cassette to the APC linker on the labeled protein; (d) detecting the protein by (i) treating the DNA with an initiator nucleotide under hybridizing conditions; and (ii) treating the DNA with an RNA polymerase and nucleotides or nucleotide analogs that permit detection. Process (d) occurs repeatedly for each RNA polymerase bound.

Cancer Detection

The present invention is useful for detecting cancer in mammals. In particular the invention is useful during diagnosis of cancer. Preferred mammals include monkeys, apes, cats, dogs, cows, pigs, horses, rabbits and humans. Particularly preferred are humans.

The methods of the invention are particularly useful for monitoring the status of DNA methylation, genetic mutations, mRNA expression patterns, and protein expression patterns. The invention can be used to detect, diagnose, and monitor diseases, and/or disorders associated with the aberrant expression and/or activity of a polypeptide or polynucleotide. The invention provides for the detection of the aberrant expression of a polypeptide or polynucleotide, the presence of mutations, and changes in methylation status of DNA. The method comprises (a) assaying the expression of the polypeptide or polynucleotide of interest in cells, tissue or body fluid of an individual using the methods of abortive initiaton transcription described above, and (b) comparing the level of gene expression, protein expression, or presence of sequences of interest with a standard gene expression level, whereby an increase or decrease in the assayed polypeptide or polynucleotide level compared to the standard level is indicative of aberrant expression indicating presence of cancer or a pathogen of interest.

The presence of an abnormal amount of transcript in biopsied tissue or body fluid from an individual may indicate a predisposition for the development of cancer or a disease of interest, or may provide a means for detecting the disease prior to the appearance of actual clinical symptoms. A more definitive diagnosis of this type may allow health professionals to employ preventative measures or aggressive treatment earlier thereby preventing the development or further progression of the cancer or disease caused by the pathogen.

The diagnostic assays of the invention can be used for the diagnosis and prognosis of any disease, including but not limited to Alzheimer disease, muscular dystrophy, cancer, breast cancer, colon cancer, cystic fibrosis, fragile X syndrome, hemophilia A and B, Kennedy disease, ovarian cancer, lung cancer, prostate cancer, retinoblastoma, myotonic dystrophy, Tay Sachs disease, Wilson disease, and Williams disease. These assays are believed to be particularly useful for the diagnosis and prognosis of all types of cancer.

Kits of the Invention

The invention also provides kits for carrying out the methods of the invention. Such kits comprise, in one or more containers, usually conveniently packaged to facilitate their use in assays, quantities of various compositions essential for carrying out the assays in accordance with the invention. Thus, the kits comprise one or more initiators according to the invention. The kits may additionally comprise an enzyme with polymerase activity, such as an RNA and/or DNA polymerase for example, to extend the primer of the kit, as well as reagents for processing a target nucleic acid. The kit may also comprise nucleotides and/or nucleotide analogs to enable detection of the oligonucleotide products synthesized by the methods of the invention. The kits may also include oligonucleotide target site probes for forming a bubble complex on the target nucleic acid. The kit may also contain an abortive promoter cassette. The kits may also contain components for the collection and transport of materials, including but not limited to, membranes, affinity materials, test tubes, petri dishes, and dipsticks. The kit may also include microtiter plates, bio-chips, magnetic beads, gel matrices, or other forms of solid matrices to which an oligonucleotide capture probe, which is specific for a particular target sequence, has been bound. The relative amounts of the components in the kits can be varied to provide for reagent concentrations that substantially optimize the reactions involved in the practice of the methods disclosed herein and/or to further optimize the sensitivity of any assay.

The test kits of the invention can also include, as is well-known to those skilled in the art, various controls and standards, such as solutions of known target nucleic acid concentration, including no target sequence (negative control), to ensure the reliability and accuracy of the assays carried out using the kits and to permit quantitative analyses of test samples using the kits. Optionally, the kits may include a set of instructions, which are generally written instructions, though the instructions may be stored on electronic storage media (e.g., magnetic diskette or optical disk), relating to the use of the components of the methods of the invention. The instructions provided with the kit generally also include information regarding reagents (whether included or not in the kit) necessary or preferred for practicing the methods of the invention, instructions on how to use the kit, and/or appropriate reaction conditions.

EXAMPLES

The following examples are provided for purposes of illustration only and not of limitation. Those of skill in the art will readily recognize a variety of non-critical parameters which could be changed or modified to yield essentially similar results.

Example 1

Synthesis of a Dye Labeled Initiator

One of several reactions to chemically modify a nucleotide is described herein. 5' a-S-CTP, which was purchased from TriLink BioTechnologies, was treated following the manufacturer's instructions with calf intestinal phosphatase. The phosphatase treatment is important because it increases the efficiency of the labeling reaction. Following phosphatase treatment, 12.5 mM α-S-CMP was mixed with 5 μl of 0.2 M NaHCO3, 15 μl of DMF, and 15 μl of 90 mM IAEDANS (purchased from Molecular Probes) in DMF, and incubated at room temperature for 1 hour. The reaction was extracted with 5 volumes water saturated ethyl ether. The aqueous phase was removed and the ether eliminated by evaporation. Thin layer chromatography was performed following standard protocols known in the art, and demonstrated that the reaction successfully produced 5'-IEADANS-S-CMP (FIG. 26).

Example 2

RNA Primer-Initiated Abortive Transcription with an RNA Polymerase

Reaction conditions have been optimized for abortive tran-cription initiaton. The components and concentrations of Buffer T favor abortive transcription initiation. Buffer T is comprised of: 20 mM Tris-HCl pH 7.9, 5 mM $MgCl_2$, 5 mM beta-mercaptoethanol, 2.8% (v/v) glycerol. Primers are either ribonucleoside-triphosphates (NTPs) or dinucleotides ranging in concentration from 0.2-1.3 mM. Final NTP concentrations range from 0.2-1.3 mM. The high ends of the concentration ranges are designed for preparative abortive transcription. The template DNA concentration is less than 2 μM in terms of phosphate. *E. coli* RNA polymerase is added to a final concentration of between 15 nM and 400 nM. Either holoenzyme or core can be used with a single-stranded template DNA. Yeast inorganic pyrophosphatase is added to 1 unit/ml in preparative reactions to prevent the accumulation of pyrophosphate. At high concentrations pyrophosphate can reverse the synthesis reaction causing RNA polymerase to regenerate NTPs at the expense of the RNA products. One unit of pyrophosphatase is defined as the amount of enzyme to liberate 1.0 μM of inorganic orthophosphate per min. at 25° C. and pH 7.2. Reactions are incubated at 37° C. for up to 72 hours for preparative reactions. These conditions are representative; for specific templates, optimization of particular components and concentrations may enhance the efficiency of abortive initiation.

Three different initiators were used in this example: (1) TAMARA-ApG; (2) Biotin ApG; and (3) ApG. The target nucleic acid template was denatured by boiling for 5 minutes at 95° C. and immediately placing on ice. Each reaction was prepared as follows:

5.0 µl 1× Buffer T
2.5 µl of a-32P-UTP
14.3 µl ddH20
1 µl of *E. coli* RNA polymerase (1 U/µl)
100 ng (2 µl) of template DNA
10 nmoles (1.2 µl) of initiator
22.8 µl of reaction buffer Incubate at 37° C. for 12-16 hours. Thin layer chromatography was performed using standard methods known in the art to determine the extent of incorporation of UTP in the third position (FIG. 27).

Both TAMARA-ApG and biotin ApG allowed for incorporation of the nucleotide UTP. Biotin ApG incorporated more efficiently than TAMARA-ApG, but not as efficient as ApG.

Example 3

Abortive Initiation Reaction with a Labeled Terminator

Abortive transcription initiation reactions may be performed with a labeled initiator and/or a labeled terminator. The following reaction conditions were used to incorporate a labeled terminator:
5 µl 1× Buffer T
3 µl 100 ng denatured DNA template (pBR322)
13.5 µl dd H$_2$0
1 µl *E. coli* RNA polymerase
1.2 µl dinucleotide initiator ApG
1.5 µl of 7 mM SF-UTP Incubate mixture at 37° C. for 16 hours in temperature controlled microtitre plate reader. Thin layer chromatography was performed using standard methods known in the art, and demonstrated that the labeled trinucleotide ApGpU was generated (FIG. 28).

Example 4

Fluorescent Energy Transfer Between Donors and Acceptors

The above examples have demonstrated that both labeled initiators and terminators can be incorporated into the oligonucleotide products. One efficient method to measure incorporation of the labeled nucleotides is by Fluorescent Resonance Energy Transfer. The following conditions were used to demonstrate FRET between a labeled initiator and a labeled terminator:
5 µl 1× Reaction Buffer (Buffer T)
3 µl denatured DNA template (300 ng pBR322)
13.5 µl dd H$_2$0
1 µl *E. coli* RNA polymerase
1.2 µl Initiator (TAMARA-ApG or ApG or Biotin-ApG)
1.5 µl of of 7 mM SF-UTP The reaction mixture was incubated at 37C for 16 hours in temperature controlled microtitre plate reader, which was set to read at the following parameters: Ex 485, Em 620, Gain 35, 99 reads/well/cycle. Under the reaction conditions described above, the RNA polymerase reiteratively synthesizes an oligonucleotide product composed of the initiator (TAMARA-SpApG) and the terminator (SF-UTP).

Formation of the oligonucleotide product, TAMARA-SpApGpU-SF, places the initiator and the terminator within 80 angstroms of each other, which allows for the transfer of energy between the chemical moieties. Energy is transferred from the donor, which is SF-UTP, to the acceptor, which is TAMARA-ApG. This transfer of energy can be detected and/or quantitated by a change in wavelength emission of TAMARA (TAMARA Abosrbance=540 nm; Emission=565 nm)

As the oligonucleotide product is generated, energy transfer occurs between TAMARA-SpApG and SF-UTP, which changes the wavelength at which TAMARA emits. If RNA polymerase or DNA is omitted from the reaction, there is no transfer of energy between the initiator and the terminator, and no change in the wavelength at which TAMARA emits.

Example 5

Determination of the Methylation Status of Specific Residues of the CDKN2A Gene

The sample to be analyzed is collected from a human stool sample. Methods of DNA extraction from stool samples are well known in the art, and commercial kits are avialalbe for extracting human DNA from stool samples, such as QIAamp DNA Stool Mini Kit from Qiagen (Valencia, Calif.).

After extraction, the sample is applied to the wells of a microtiter plate, which contain a capture probe for the gene of interest, in this particular example, the capture probe is for CDKN2A gene. The nucleotide sequence of a representative capture probe for the CpG islands of the CDKN2A gene is as follows:

```
                                            (SEQ ID NO:16).
ATATACTGGGTCTACAAGGTTTAAGTCAACCAGGGATTGAAATATAACTT

TTAAACAGAGCTGG.
```

The DNA sample is incubated with the capture probe to allow hybridization. A representative hybridization protocol is as follows: (1) prehybridize with 2.5×SSC, 5× Denhardts at room temperature for 30 minutes; (2) hybridize with 2.5× SSC, 5× Denhardts, 30% formamide at room temperature for 2 hours; (3) wash twice with 1×SSC at 42° C. for 10 minutes, maintaining 42° C.; and (4) wash three times with 0.1×SSC at 42° C. for 10 minutes, maintaining 42° C.

The DNA is treated with a deaminating agent, such as sodium bisulfite, which will de-aminate the unmethylated C's in the DNA, while leaving the methylated C's unaltered. The wells are then washed under medium stringency conditions to remove the remaining sodium bisulfite.

A representative transcription reaction is comprised of the following components: *E. coli* holoenzyme RNA polymerase; reaction buffer: 10 nM Tris-HCl, pH 7.0; 10 mM KCl; 0.5 mM Na$_2$EDTA; and 50 mg/ml BSA; an initiator, and nucleotide analogs. The reaction conditions for particular nucleotide sequence may vary. Other polymerases may be used, such as *E. coli* T7, or SP6. The reaction buffer can be optimized to increase abortive initiation events by adjusting the salt concentration, divalent cations and concentrations, the glycerol content, and the amount and type of reducing agent to be used.

The initiator will be a 5'-αSpCpG dimer labeled through the 5'-S with fluorescein, which fucntions as the donor in this reaction. The nucleotide analog(s) will be labeled with TAMARA, which will function as the acceptor in this reaction. The initiator can be labeled with either the donor or the acceptor in the FRET reaction, and dependending upon the fluorescent molecule used to label the initiator, the nucleotide analog(s) will be labeled with either a donor or an acceptor.

Fluorescein is excited using a 360 nm wavelength filter; the resulting emission peak is at about 515 nm. If the TAMARA is in close proximity to the fluorescein, it becomes excited at 542 nm, resulting in an emission peak of 568 nm. The near ultraviolet wavelength excties the fluorescein but not the rhodamine. Therefore signal will only be generated if the fluorescein is in close proximity to the rhodamine. This signal can be generated and monitored in a fluorescent microtitre plate reader that has been fitted with specific excitation and emission filters for this FRET pair. These filters and plate readers are commercially available from a number of sources, although most clinical labs and research facilities already use a fluorescent microtitre plate reader.

In the foregoing specification, the invention has been described with reference to specific embodiments. However, it will be appreciated that various modifications and changes can be made without departing from the scope of the present invention as set forth in the claims below. The specification and figures are to be regarded in an illustrative manner, rather than a restrictive one, and all such modifications are intended to be included within the scope of present invention. Accordingly, the scope of the invention should be determined by the appended claims and their legal equivalents, rather than by the examples given above. For example, the steps recited in any of the method or process claims may be executed in any order and are not limited to the order presented in the claims.

What is claimed is:

1. A method for detecting a target DNA or RNA polynucleotide, said method comprising:
    (a) incubating a single-stranded target polynucleotide with a second polynucleotide comprising a sequence that hybridizes to the single-stranded target polynucleotide forming a bubble complex, wherein said bubble complex comprises a first double-stranded upstream region, a non-complementary single-stranded middle region, and a second double-stranded downstream region, an initiator, an RNA polymerase, and a terminator, wherein said initiator hybridizes with said target polynucleotide;
    (b) extending said initiator until said terminator is incorporated into an oligonucleotide transcript, by the process of abortive transcription;
    (c) repeating steps (a) and (b), thereby synthesizing multiple reiterative oligonucleotide transcripts from said target polynucleotide; and
    (d) detecting or quantifying said reiterative oligonucleotide transcripts, wherein the presence of said reiterative oligonucleotide transcripts is indicative of the presence of said target DNA or RNA polynucleotide.

2. The method of claim 1, further comprising detecting or quantifying said reiterative oligonucleotide transcripts by modifying a nucleoside or nucleotide in at least one of the members selected from the group consisting of said terminator and said initiator.

3. The method of claim 2, wherein said modifying comprises incorporating a label moiety.

4. The method of claim 3, wherein said label moiety comprises a fluorophore moiety.

5. The method of claim 4, wherein said fluorophore moiety comprises a fluorescent energy donor and a fluorescent energy acceptor wherein said moiety is detected or quantified by fluorescence resonance energy transfer.

6. The method of claim 1, wherein said polymerase is selected from the group consisting of: a DNA-dependent RNA polymerase, an RNA-dependent RNA polymerase, a modified RNA polymerase, and an RNA polymerase that is the product of dnaG gene.

7. The method of claim 6, wherein said polymerase comprises an RNA polymerase derived from one of E. coli, E. coli bacteriophage T7, E. coli bacteriophage T3, and S. typhimurium bacteriophage SP6.

8. The method of claim 1, wherein said reiterative oligonucleotide transcripts being synthesized are one of the lengths selected from the group consisting of: about 2 to about 100 nucleotides.

9. The method of claim 1, wherein said chain terminator comprises a nucleotide analog.

10. The method of claim 1, wherein said single-stranded target polynucleotide is DNA.

11. The method of claim 10, further comprising modifying at least one of said initiator or nucleotides used to extend said initiator to enable detection of said reiterative nucleotide transcripts.

12. The method of claim 11, wherein modifying comprises incorporating an independently selected label moiety into at least one of said initiator and said nucleotides.

13. The method of claim 12, wherein said label moiety comprises a fluorophore moiety.

14. The method of claim 13, wherein detecting comprises detecting by fluorescence resonance energy transfer and said fluorophore moiety comprises one of a fluorescent energy donor and a fluorescent energy acceptor.

15. The method of claim 10, wherein said reiterative oligonucleotide transcripts comprises from about 2 to about 26 nucleotides.

16. The method of claim 10, wherein said detecting comprises hybridizing a complementary sequence to the synthesized reiterative oligonucleotide transcript.

17. The method of claim 16, wherein said complementary sequence is modified to comprise an independently selected label moiety.

18. The method of claim 17, wherein said label moiety comprises a fluorophore moiety.

19. The method of any one of claims 4, 13, or 18 wherein said fluorophore moiety is selected from the group consisting of: 4-acetamido-4'-isothiocyanatostilbene-2,2'disulfonic acid; acridine and derivatives: acridine, acridine isothiocyanate; 5-(2'-aminoethyl)anminonaphthalene-1-sulfonic acid (EDANS); 4-amino-N-[3-vinylsulfonyl)phenyl]naphthalimide-3 ,5 disulfonate; N-(4-amino-1-naphthyl) maleimide; anthranilamide; BODIPY; Brilliant Yellow; coumarin, and derivatives: coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5', 5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2-disulfonic acid; 5-[dimethylamino]naphthalene-1-sulfonyl chloride (DNS, dansylchloride); 4-dimethylaminophenylazophenyl-4'isothiocyanate (DABITC); eosin and derivatives: eosin, eosin isothiocyanate; erythrosin and derivatives: erythrosin B, erythrosin, isothiocyanate; ethidium; fluorescein and derivatives: 5-carboxyfluorescein (FAM),5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate, QFITC, (XRJTC); fluorescamine; IR144; IR 1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl ipyrene; butyrate quantum dots; Reactive Red 4; rhodamine and derivatives: 6-carboxy-X-rhodamine (ROX), 6-carboxyrhodamine (R6G), lissamine rhodamine B, sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRJTC); riboflavin; rosolic acid; terbiun chelate derivatives; Cy 3; Cy 5; Cy 5.5; Cy 7; IRD 700; IRD 800; La Jolla Blue; phthalo cyanine; and naphthalo cyanine.

20. The method of claim 10, further comprising immobilizing said target sequence.

21. The method of claim 20, wherein immobilizing comprises hybridizing a capture probe to a portion of said single-stranded target polynucleotide sequence.

22. The method of claim 1, wherein said single-stranded target polynucleotide is RNA.

23. The method of claim 22, further comprising synthesizing multiple reiterative oligonucleotide transcripts by modifying a nucleotide in at least one of the members selected from the group consisting of said terminator, and said initiator.

24. The method of claim 23, wherein said modifying comprises incorporating a label moiety.

25. The method of claim 24, wherein said label moiety comprises a fluorophore moiety.

26. The method of claim 25, wherein said fluorophore moiety comprises a fluorescent energy donor and a fluorescent energy acceptor.

27. The method of claim 22, wherein said polymerase is selected from the group consisting of: an RNA-dependent RNA polymerase and a modified RNA-polymerase.

28. The method of claim 27, wherein said polymerase comprises an RNA polymerase derived from one of *E. coli*, *E. coli* bacteriophage T7, *E. coli* bacteriophage T3, and *S. typhimurium* bacteriophage SP6.

29. The method of claim 22, wherein said reiterative oligonucleotide transcripts being synthesized are of a length of about 2 to about 100 nucleotides.

30. The method of claim 22, wherein said terminator comprises a nucleotide analog.

31. The method of any one of claims 1 and 22, wherein said incubating further comprises in the presence of ribonucleotides.

32. The method of claim 31, wherein said ribonucleotides are modified.

33. The method of claim 32, wherein said modifying further comprises incorporating an independently selected label moiety.

34. The method of claim 33, wherein said label moiety comprises a fluorophore moiety.

35. The method of any one of claims 1, 10 and 22, wherein said initiator is selected from the group consisting of: nucleosides, nucleoside analogs, nucleotides, and nucleotide analogs.

36. The method of any one of claims 1 and 22, wherein said single-stranded target polynucleotide is RNA.

37. The method of claim 36, wherein the RNA is mRNA.

38. The method of claim 36, wherein the RNA polymerase is an RNA-dependent RNA polymerase.

39. The method of claim 38, wherein the RNA-dependent RNA-polymerase is poliovirus RNA polymerase.

40. The method of claim 36, further comprising (a) incubating said single-stranded target RNA with a reverse transcriptase.

41. The method of any one of claims 1 and 22, comprising incubating said single-stranded target polynucleotide with additional ribonucleotides.

42. The method of claim 41, wherein said ribonucleotides are modified.

43. The method of claim 42, wherein said modification comprises the incorporation of a labeling moiety.

44. The method of any claims 1 and 22, wherein said single-stranded target polynucleotide is from a virus.

45. The method of claim 44, wherein said single-stranded polynucleotide is RNA.

46. The method of any one of claims 1 and 22, wherein said single-stranded target polynucleotide is from a bacterium.

47. The method of claim 1, wherein the initiator is 1-3 bases in length.

48. The method of claim 47, wherein the initiator is one base in length.

49. The method of claim 47, wherein the initiator is two bases in length.

50. The method of claim 47, wherein the initiator is three bases in length.

51. A method for detecting multiple abortive reiterated oligonucleotides from a target DNA or RNA polynucleotide, said method comprising:
   (a) incubating a single-stranded target polynucleotide with a second polynucleotide comprising a sequence that hybridizes to the single-stranded target polynucleotide forming a bubble complex, wherein said bubble complex comprises a first double-stranded up stream region, a non-complementary single-stranded middle region, and a second double-stranded downstream region, an initiator, an RNA polymerase, wherein said initiator hybridizes with said target polynucleotide;
   (b) synthesizing multiple oligonucleotides from said single-stranded target polynucleotide, wherein said initiator is extended until terminated due to nucleotide deprivation, thereby synthesizing multiple abortive reiterative oligonucleotide transcripts; and
   (c) detecting or quantifying said abortive reiterative oligonucleotide transcripts.

52. A method for detecting a target DNA or RNA polynucleotide, said method comprising:
   (a) incubating a single-stranded target polynucleotide with a second polynucleotide with a sequence that hybridizes to the single-stranded target polynucleotide forming a bubble complex, wherein said bubble complex comprises a first double-stranded up stream region, a non-complementary single- stranded middle region, and a second double-stranded downstream region, an RNA polymerase, an initiator wherein said initiator is a tetranucleotide, pentanucleotide, hexanucleotide or analog thereof, and a terminator, wherein said initiator hybridizes with said target polynucleotide;
   (b) extending said initiator until said terminator is incorporated into an oligonucleotide transcript, by the process of abortive transcription;
   (c) repeating steps (a) and (b), thereby synthesizing multiple reiterative oligonucleotide transcripts from said target polynucleotide; and
   (d) detecting or quantifying said reiterative oligonucleotide transcripts, wherein the presence of said reiterative oligonucleotide transcripts is indicative of the presence of said target DNA or RNA polynucleotide.

* * * * *